(12) United States Patent
Lipscomb et al.

(10) Patent No.: US 8,927,254 B2
(45) Date of Patent: Jan. 6, 2015

(54) PYROCOCCUS FURIOSUS STRAINS AND METHODS OF USING SAME

(75) Inventors: Gina L. Lipscomb, Athens, GA (US); Joel Andrew Farkas, Athens, GA (US); Michael W. W. Adams, Athens, GA (US); Janet Westpheling, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 353 days.

(21) Appl. No.: 13/248,377

(22) Filed: Sep. 29, 2011

(65) Prior Publication Data
US 2012/0135411 A1 May 31, 2012

Related U.S. Application Data

(60) Provisional application No. 61/387,656, filed on Sep. 29, 2010.

(51) Int. Cl.
*C12N 1/15* (2006.01)
*C12N 1/00* (2006.01)
*C12N 15/74* (2006.01)

(52) U.S. Cl.
CPC ..................................... *C12N 15/74* (2013.01)
USPC ................................... 435/254.1; 435/254.11

(58) Field of Classification Search
CPC ................................ C12N 1/20; C12N 15/74
See application file for complete search history.

(56) References Cited

U.S. PATENT DOCUMENTS

| | | | |
|---|---|---|---|
| 5,872,238 | A | 2/1999 | Weber et al. |
| 8,278,087 | B2 | 10/2012 | Remmereit et al. |
| 8,420,358 | B2 | 4/2013 | Claassen et al. |
| 8,420,375 | B2 | 4/2013 | Osterhout et al. |
| 8,435,770 | B2 | 5/2013 | Hogsett et al. |
| 8,470,566 | B2 | 6/2013 | Trawick et al. |
| 8,486,687 | B2 | 7/2013 | Atkinson et al. |
| 8,497,128 | B2 | 7/2013 | Van Kranenburg et al. |

OTHER PUBLICATIONS

Adams et al. "Key Role for Sulfur in Peptide Metabolism and in Regulation of Three Hydrogenases in the Hyperthermophilic Archaeon *Pyrococcus furiosus*" 2001. *J. Bacteriol.* 183(2):716-724.
Allers et al. "Development of Additional Selectable Markers for the Halophilic Archaeon *Haloferax volcanii* Based on the *leuB* and *trpA* Genes" 2004. *Appl. Environ. Microbiol.* 70(2):943-953.
Allers et al. "Archaeal genetics—the third way". 2005. *Nat. Rev. Genet.* 6:58-73.
Altschul et al., "Gapped BLAST and PSI-BLAST: a new generation of protein database search programs" 1997. *Nucleic Acids Res.* 25(17):3389-3402.
Atomi. "Recent progress towards the application of hyperthermophiles and their enzymes" 2005. *Curr. Opin. Chem. Biol.* 9:166-173.
Atomi et al. "Targeted Gene Disruption as a Tool for Establishing Gene Function in Hyperthermophilic Archaea" . 2008. *CRC Press* 2008. pp. 213-223.
Averhoff. "Shuffling genes around in hot environments: the unique DNAS transporter of *Thermus thermophilus*" 2009. *FEMS Microbiol. Rev.* 33:611-626.
Berkner et al. "Genetic tools for *Sulfolobus* spp.: vectors and first applications" 2008. *Arch Microbiol.* 190:217-230.
Berquist et al. "An Archaeal Chromosomal Autonomously Replicating Sequence Element from an Extreme Halophile, *Halobacterium* sp. Strain NRC-1" 2003. *J. Bacteriol.* 185(20):5959-5966.
Bertani et al. "Genetic transformation in the methanogen *Methanococcus voltae* PS" 1987. *J. Bacteriol.* 169(6):2730-2738.
Boeke et al. "A Positive selection for mutants lacking orotidine-5'-phosphate decarboxylase activity in yeast: 5-fluoro-orotic acid resistance". 1984. *Mol. Gen. Genet.* 197:345-346.
Cammarano et al. "Insensitivity of archaebacterial ribosomes to protein synthesis inhibitors. Evolutionary implications" 1985. *EMBO J.* 4(3):811-816.
Claverys et al. "The genetic transformation machinery: composition, localization, and mechanism" 2009. *FEMS Microbiol. Rev.* 33:643-656.
Contursi et al. "Identification and autonomous replication capability of a chromosomal replication origin from the archaeon *Sulfolobus solfataricus*" 2004. *Extremophiles.* 8:385-391.
Deng et al. "Unmarked gene deletion and host-vector system for the hyperthermophilic crenarchaeon *Sulfolobus islandicus*" 2009. *Extremophiles.* 13:735-746.
Dodsworth et al. "Inter-domain conjugal transfer of DNA from Bacteria to Archaea". 2010. *Appl. Environ. Microbiol.* 76(16):5644-5647.
DiRuggiero et al. "Repair of Extensive Ionizing-Radiation DNA Damage at 95° C. in the Hyperthermophilic Archaeon *Pyrococcus furiosus*" 1997. *J. Bacteriol.* 179(14):4643-4645.
Egorova et al. "Industrial relevance of thermophilic Archaea" 2005. *Curr. Opin. Microbiol.* 8:649-655.
Erauso et al. "Caracterisation preliminaire d'une archaebacterie hyperthermophile possedant un plasmide,isolee d'une source hydrothermale du bassin Nord Fidjien" 1992. *C.R. Acad. Sci.* 314(11):387-393.
Erauso et al. "*Pyrococcus abyssi* sp. nov., a new hyperthermophilic archaeon isolated from a deep-sea hydrothermal vent" 1993. *Arch. Microbiol.* 160:338-349.
Erauso et al. "Sequence of Plasmid pGT5 from the Archaeon *Pyrococcus abyssi*: Evidence for Rolling-Circle Replication in a Hyperthermophile" 1996. *J. Bacteriol.* 178(11):3232-3237.

(Continued)

*Primary Examiner* — Michele K Joike
(74) *Attorney, Agent, or Firm* — Mueting, Raasch & Gebhardt, P.A.

(57) ABSTRACT

Provided herein are methods for transforming a *Pyrococcus furiosus* with a polynucleotide. In one embodiment, the method includes contacting a *P. furiosus* with a polynucleotide under conditions suitable for uptake of the polynucleotide by the *P. furiosus*, and identifying transformants at a frequency of, for instance, at least $10^5$ transformants per microgram DNA. Also provided are isolated *Pyrococcus furiosus* having the characteristics of *Pyrococcus furiosus* COM1, and plasmids that include an origin of replication that functions in a *Pyrococcus furiosus*. The plasmid is stable in a recipient *P. furiosus* without selection for more than 100 generations and is structurally unchanged after replication in *P. furiosus* for more than 100 generations.

19 Claims, 17 Drawing Sheets

(56) References Cited

OTHER PUBLICATIONS

Farkas et al. "Defining Components of the Chromosomal Origin of replication of the Hyperthermophilic Archaeon *Pyrococcus furiosus* Needed for Construction of a Stable Replicating Shuttle Vector" 2011. *Appl. Environ. Microbiol.* 77(18):6343-6349.

Fiala et al. "*Pyrococcus-furiosus* Sp-Nov Represents a Novel Genus of Marine Heterotrophic Archaebacteria Growing Optimally at 100-Degrees C." 1986. *Archives of Microbiology*. 145:56-61.

Fujii et al. "Molecular Cloning and Expression of Penicillinase Genes from *Bacillus licheniformis* in the Thermophile *Bacillus stearothermophilus*" 1982. *Journ. of Gen. Microbilogy.* 128:2997-3000.

Genbank Accession Number: National Center for Biotechnology Information, National Library of Medicine, National Institutes of Health, GenBank Locus NC_003413, Accession No. NC_003413, "*Pyrococcus furiosus* DSM 3638 chromosome, complete genome," Retrieved on 2013/20/24. Retrieved from the Internet:<URL:http://www.ncbi.nlm.nih.gov/nuccore/NC_003413. 1 page.

Grogan et al. "Recombination of Synthetic Oligonucleotides with Prokaryotic chromosomes: substrate requirements of the *Escherichia coli*/λRed and *Sulfolobus acidocaldarius* recombination systems" 2008. *Mol. Microbiol*. 69(5):1255-1265.

Grogan, D.W. "Homologous recombination in *Sulfolobus acidocaldarius*: genetic assays and functional properties" 2009. *Biochemical Society Transactions*. 37:88-91.

Hoekstra et al. "Role of *rec*BC Nuclease in *Escherichia coli* Transformation" 1980. *J. Bacteriol.* 143(2):1031-1032.

Imanaka. "Host-vector systems in thermophilic *Bacilli* and their applications". 1983. Trends in Biotechnology. 1(5):139-144.

Jenney et al. "Hydrogenases of the model hyperthermophiles". 2008. *Ann N Y Acad Sci*. 1125:252-266.

Johnsborg et al. "Natural genetic transformation: prevalence, mechanisms and function". 2007. *Res. Microbiol.* 158:767-778.

Koyama et al. "Genetic Transformation of the Extreme Thermophile *Thermus thermophilus* and of Other *Thermus* spp." 1986. *J. Bacteriol.* 166(1):338-340.

Kurosawa et al. "Homologous recombination of exogenous DNA with the *Sulfolobus acidocaldarius* genome: Properties and uses" 2005. *FEMS Microbiol. Lett*. 253:141-149.

Lam et al. "Shuttle vectors for the archaebacterium *Halobacterium volcanii*" 1989. *Proc. Natl Acad Sci USA* 86:5478-5482.

Lipscomb et al. "Natural Competence in the Hyperthermophilic Archaeon *Pyrococcus furiosus* Facilitates Genetic Manipulation: Construction of Markerless Deletions of Genes Encoding the Two Cytoplasmic Hydrogenases" 2011. *Appl. Environ. Microbiol.* 77(7):2232-2238.

Lorenz et al. "Bacterial Gene Transfer by Natural Genetic Transformation in the Environment" 1994. *Microbiol. Rev.* 58(3):563-602.

Lucas et al. "Construction of a Shuttle Vector for, and Spheroplast Transformation of, the Hyperthermophilic Archaeon *Pyrococcus abyssi*" 2002. *Appl. Environ. Microbiol.* 68(11):5528-5536.

Ma et al. "Hydrogenase of the hyperthermophile *Pyrococcus furiosus* is an elemental sulfur reductase or sulfhydrogenase: evidence for a sulfur-reducing hydrogenase ancestor". 1993. *Proc. Natl. Acad. Sci. USA*. 90:5341-5344.

Ma et al. "Characterization of Hydrogenase II from the Hyperthermophilic Archaeon *Pyrococcus furiosus* and Assessment of its Role in Sulfur Reduction" 2000. *J. Bacteriol.* 182(7):1864-1871.

Marsin et al. "A rolling circle replication initiator protein with a nucleotidyl-transferase activity encoded by the plasmid pGT5 from the hyperthermophilic archaeon *Pyrococcus abyssi*" 1998. *Mol. Microbiol*. 27(6):1183-1192.

Matsumi et al. "Disruption of a sugar transporter gene cluster in a hyperthermophilic archaeon using a host-marker system based on antibiotic resistance". 2007. *J. Bacteriol.* 189(7):2683-2691.

Matsumi, Rie. Thesis. "Studies on membrane-bound peptidases and a sugar transporter in the hyperthermophilic archaeon *Thermococcus kodakaraensis*" Kyoto University. Issue Date Mar. 24, 2008. 32 total pages.

Matsunaga et al. "In vivo interactions of archael Cdc6/Orc1 and minichromosome maintenance proteins with the replication origin" 2001. *Proc Natl. Acad Sci USA*. 98(20):11152-11157.

Matsunaga et al., "Genomewide and biochemical analyses of DNA-binding activity of Cdc6/Orc1 and Mcm proteins in *Pyrococcus* sp." 2007. *Nucl. Acids Res*. 35(10):3214-3222.

Noll et al. "Recent advances in genetic analyses of hyperthermophilic Archaea and Bacteria" 1997. *Arch. Microbio.* 168:73-80.

Oka et al. "Replication origin of the Escherichia coli K-12 chromosome: the size and structure of the minimum DNA segment carrying the information for autonomous replication" 1980. *Mol Gen Genet*. 178(1):9-20.

Ortenberg et al. "The extremely halophilic archaeon *Haloferax volcanii* has two very different dihydrofolate reductases" 2000. *Mol. Microbiol*. 35(6):1493-1505.

Patel et al. "Natural and Electroporation-Mediated Transformation of *Methanococcus voltae* Protoplasts". 1994. *Appl Environ Microbiol.* 60(3):903-907.

Peck et al. Homologous gene knockout in the archaeon *Halobacterium salinarum* with ura3 as a counterselectable marker. 2000. *Mol Microbiol*. 35(3):667-676.

Possot et al. "Analysis of Drug Resistance in the Archaebacterium *Methanococcus voltae* with Respect to Potential Use in Genetic Engineering" 1988. *Appl. Environ. Microbiol*. 54(3):734-740.

Robinson et al. "Identification of Two Origins of Replication in the Single Chromosome of the Archaeon *Sulfolobus solfataricus*" 2004. *Cell*. 116:25-38.

Rother et al. "Genetic technologies for Archaea" 2005. *Curr. Opin. Microbiol*. 8:745-751.

Sambrook et al. Molecular Cloning: A Laboratory Manual, Cold Spring Harbor Laboratory Press. 1989, or Ausubel, R.M., ed. Current Protocols in Molecular Biology. 1994. Title Page, Copyright Page, Table of Contents. 31 pages total.

Sambrook et al. Molecular cloning: a laboratory manual, 3$^{rd}$ ed. Cold Spring Harbor Laboratory Press, Cold Spring Harbor: NY, NY 2001. 18 pgs.

Santangelo et al. "Polarity in archael operon transcription in *Thermococcus kodakaraensis*" 2008. *J. Bacteriol*. 190(6):2244-2248.

Santangelo et al. "Shuttle vector expression in *Thermococcus kodakaraensis*: contributions of cis elements to protein synthesis in a hyperthermophilic archaeon" 2008. *Appl Environ Microbiol.* 74(10):3099-3104.

Santangelo et al. "*Thermococcus kodakarensis* genetics: TK1827-encoded beta-glycosidase, new positive-selection protocol, and targeted and repetitive deletion technology" 2010. *Appl Environ Microbiol.* 76(4):1044-1052.

Santangelo et al. 2011. In: Extremophiles Handbook, Horikoshi (ed.); Springer, Chapter 4.8. pp. 567-582.

Sato et al. "Improved and versatile transformation system allowing multiple genetic manipulations of the hyperthermophilic archaeon *Thermococcus kodakaraensis*" 2005. *Appl Environ Microbiol*. 71(7):3889-3899.

Sato et al. "Targeted gene disruption by homologous recombination in the hyperthermophilic archaeon *Thermococcus kodakaraensis* KOD1". 2003. *J. Bacteriol*. 185(1):210-220.

Sato et al. "Genetic evidence identifying the true gluconeogenic fructose-1,6-bisphosphatase in *Thermococcus kodakaensis* and other hyperthermophiles". 2004. *J. Bacteriol*. 186(17):5799-5807.

Schut et al. "Insights into the metabolism of elemental sulfur by the hyperthermophilic archaeon *Pyrococcus furiosus*: characterization of a coenzyme A-dependent NAD(P)H sulfur oxidoreductase". 2007. *J. Bacteriol*. 189(12):4431-4441.

Schut et al. "DNA microarray analysis of the hyperthermophilic archaeon *Pyrococcus furiosus*: evidence for anNew type of sulfur-reducing enzyme complex". 2001. *J. Bacteriol.* 183(24):7027-7036.

Soppa, J. "From genomes to function: haloarchaea as model organisms". 2006. *Microbiology*. 152(24):584-590.

(56) References Cited

OTHER PUBLICATIONS

Spitalny et al. "A polymerase III-like reinitiation mechanism is operating in regulation of histone expression in archaea". 2008. *Mol Microbiol.* 67(5):958-970.

Sugimoto et al. "Nucleotide sequence of *Escherichia coli* K-12 replication origin" 1978 *Proc Natl Acad Sci USA.* 76(2):575-579.

Sun et al. "Heterologous Expression and Maturation of an NADP-Dependent [NiFe]-Hydrogenase: A Key Enzyme in Biofuel Production" 2010. *PLoS One* 5(5):e10526. 11 pages.

Tamakoshi et al. 2011. In: Extremophiles Handbook, Horikoshi (ed.), Springer, Chapter 4.7, pp. 547-566.

Toyn et al. "A counterselection for the tryptophan pathway in yeast: 5-fluoroanthranilic acid resistance" 2000. *Yeast.* 16:553-560.

Tumbula et al. "Genetics of *Methanococcus*: possibilities for functional genomics in Archaea" 1999. *Mol. Microbiol.* 33(1):1-7.

Verhaart et al. "Hydrogen production by hyperthermophilic and extremely thermophilic bacteria and archaea: mechanisms for reductant disposal" 2010. *Environ. Technol.* 31(8-9):993-1003.

Vinopal. 1987. In: *Escherichia coli* and *Salmonella typhimurium*: cellular and molecular biology, Neidhardt et al., eds., ASM Press, Washington, DC, 990-1015. Title Page, Copyright Page, and Table of Contents. 28 pgs. total.

Waege et al. "Shuttle vector-based transformation system for *Pyrococcus furiosus*". 2010. *Appl. Environ Microbiol.* 76(10):3308-3313.

Wagner et al. "Expanding and understanding the genetic toolbox of the hyperthermophilic genus *Sulfolobus*" 2009. *Biochem. Soc. Trans.* 37(1):97-101.

Worrell et al. "Genetic transformation system in the archaebacterium *Methanobacterium thermoautotrophicum* Marburg". 1988. *J. Bacteriol.* 170(2):653-656.

Worthington et al. "Targeted Disruption of the α-Amylase Gene in the Hyperthermophilic Archaeon *Sulfolobus solfataricus*" 2003. *J. Bacteriol.* 185(2):482-488.

Zhang et al. "Useful Host-Vector Systems in *Bacillus stearothermophilus*" 1988. Applied and Environmental Microbiology. 54(12):3162-3164.

*Figure 14*
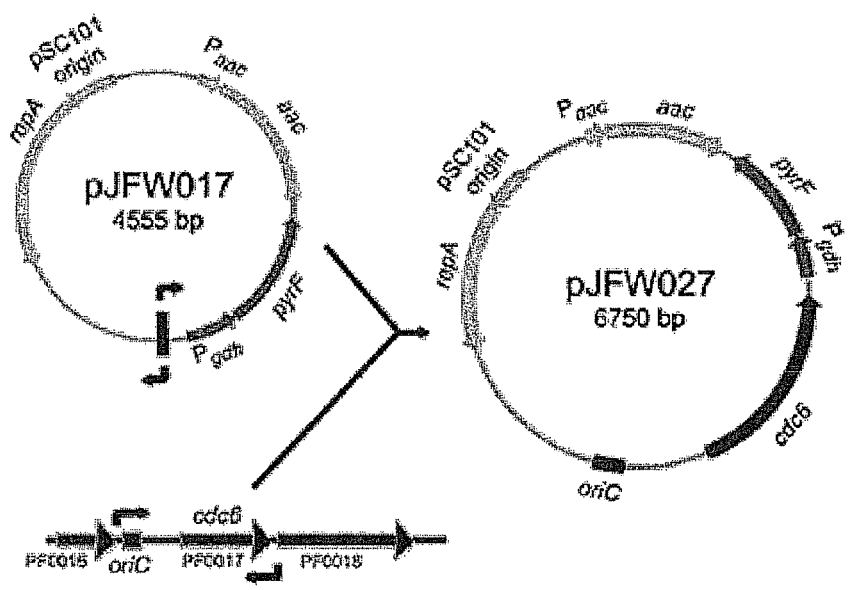
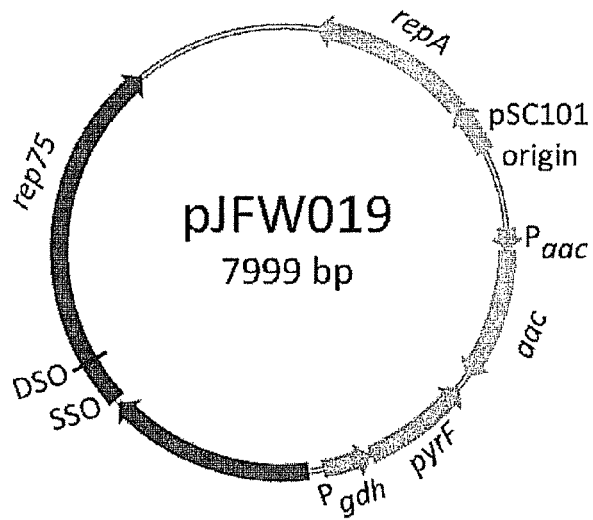
*Figure 15*

```
                              SEQUENCE LISTING

<160> NUMBER OF SEQ ID NOS: 141

<210> SEQ ID NO 1
<211> LENGTH: 39
<212> TYPE: DNA
<213> ORGANISM: Artificial
<220> FEATURE:
<223> OTHER INFORMATION: primer

<400> SEQUENCE: 1
agagagaggc atgccaccta cctcctatat tgttccatg                              39

<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2
ttgagctcca ttcagccacc tccaatattt cc                                     32

<210> SEQ ID NO 3
<211> LENGTH: 32
<212> TYPE: DNA
<213> ORGANISM: Artificial
<220> FEATURE:
<223> OTHER INFORMATION: primer

<400> SEQUENCE: 3
aggtggctga atggagctca agataaagca cc                                     32

<210> SEQ ID NO 4
<211> LENGTH: 40
<212> TYPE: DNA
<213> ORGANISM: Artificial
<220> FEATURE:
<223> OTHER INFORMATION: primer

<400> SEQUENCE: 4
agagagaggg cgcgccgtca agaggatgat taggtagagc                             40

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
ctcaactgtg atgtttgtct tgc                                               23

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cgttggcaaa caacttcctg                                                   20
```

```
<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
gaaataactc caagaccact tcc                                              23

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
gaaagctgga gcagattaca tc                                               22

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
ccaaggaaag tctacacgaa cc                                               22

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
ctgagacaac ttgttacagc ttc                                              23

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
cattccatct ccaatgaact ttgc                                             24

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
tgctcaacaa ggttagagaa gc                                               22

<210> SEQ ID NO 13
<211> LENGTH: 22
<212> TYPE: DNA
<213> ORGANISM: Artificial
<220> FEATURE:
<223> OTHER INFORMATION: primer
```

```
<400> SEQUENCE: 13
gaacaaatgg aacgtcttca cc                                            22

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
gacgtgttgg aggatctcaa g                                             21

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
gattgaaaat ggagtgagct gag                                           23

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
gttcatccct ccaaattagg tg                                            22

<210> SEQ ID NO 17
<211> LENGTH: 47
<212> TYPE: DNA
<213> ORGANISM: Artificial
<220> FEATURE:
<223> OTHER INFORMATION: primer

<400> SEQUENCE: 17
aatcacctaa tttggaggga tgaacatgat tgtactagcg ttggacg                 47

<210> SEQ ID NO 18
<211> LENGTH: 37
<212> TYPE: DNA
<213> ORGANISM: Artificial
<220> FEATURE:
<223> OTHER INFORMATION: primer

<400> SEQUENCE: 18
ctaaaaaaga ttttatcttg agctccattc tttcacc                            37

<210> SEQ ID NO 19
<211> LENGTH: 38
<212> TYPE: DNA
<213> ORGANISM: Artificial
<220> FEATURE:
<223> OTHER INFORMATION: primer

<400> SEQUENCE: 19
agagagaggg cgcgcctgag tatgaagcta gggagaac                           38

<210> SEQ ID NO 20
```

```
<211> LENGTH: 46
<212> TYPE: DNA
<213> ORGANISM: Artificial
<220> FEATURE:
<223> OTHER INFORMATION: primer

<400> SEQUENCE: 20
caacaaaaat agataaaaag gattaaacaa accacctccc aatgag        46

<210> SEQ ID NO 21
<211> LENGTH: 28
<212> TYPE: DNA
<213> ORGANISM: Artificial
<220> FEATURE:
<223> OTHER INFORMATION: primer

<400> SEQUENCE: 21
ttaatccttt ttatctattt ttgttgag                            28

<210> SEQ ID NO 22
<211> LENGTH: 40
<212> TYPE: DNA
<213> ORGANISM: Artificial
<220> FEATURE:
<223> OTHER INFORMATION: primer

<400> SEQUENCE: 22
agagagaggc ggccgctagg atttcttgta gctctagtac               40

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
cagtgaatgg ctttggaacc                                     20

<210> SEQ ID NO 24
<211> LENGTH: 22
<212> TYPE: DNA
<213> ORGANISM: Artificial
<220> FEATURE:
<223> OTHER INFORMATION: primer

<400> SEQUENCE: 24
gaaagggagt atttagggac ac                                  22

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
agaagaggga cttcaaggcg                                     20

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
```

```
taaggcgcgc catttagacc atcctccttt                                    30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
acgaagtgca caactttct cacctccttt                                     30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
agaaaagttg tgcacttcgt caagctttaa                                    30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
tccttagagc ggccgcggta gatgctttaa                                    30

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
cattatgcac atcaccctac aaga                                          24

<210> SEQ ID NO 31
<211> LENGTH: 24
<212> TYPE: DNA
<213> ORGANISM: Artificial
<220> FEATURE:
<223> OTHER INFORMATION: primer

<400> SEQUENCE: 31
agaaatccaa gggaagtcct tgaa                                          24

<210> SEQ ID NO 32
<211> LENGTH: 24
<212> TYPE: DNA
<213> ORGANISM: Artificial
<220> FEATURE:
<223> OTHER INFORMATION: primer

<400> SEQUENCE: 32
ctccctcaca gccttactag gatt                                          24

<210> SEQ ID NO 33
<211> LENGTH: 24
<212> TYPE: DNA
```

```
<213> ORGANISM: Artificial
<220> FEATURE:
<223> OTHER INFORMATION: primer

<400> SEQUENCE: 33
aagcagttac ggcaatccac gata                                              24

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
cgttgttgtt gtgctagatc c                                                 21

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
gatggcttcc tctatgctct c                                                 21

<210> SEQ ID NO 36
<211> LENGTH: 22
<212> TYPE: DNA
<213> ORGANISM: Artificial
<220> FEATURE:
<223> OTHER INFORMATION: primer

<400> SEQUENCE: 36
tcaaaaccag aatacaggga gg                                                22

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
ccttctctct cctcaccttg                                                   20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
cagtttgtcc agctgacgat                                                   20

<210> SEQ ID NO 39
<211> LENGTH: 22
<212> TYPE: DNA
<213> ORGANISM: Artificial
<220> FEATURE:
<223> OTHER INFORMATION: primer

<400> SEQUENCE: 39
caggctttag tctatggaca ac                                                22
```

```
<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
ggaagcgttt caactgagga                                                    20

<210> SEQ ID NO 41
<211> LENGTH: 22
<212> TYPE: DNA
<213> ORGANISM: Artificial
<220> FEATURE:
<223> OTHER INFORMATION: primer

<400> SEQUENCE: 41
cttccagagc tcttctaatg gc                                                 22

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
tgagcagtac agcgaagttg                                                    20

<210> SEQ ID NO 43
<211> LENGTH: 21
<212> TYPE: DNA
<213> ORGANISM: Artificial
<220> FEATURE:
<223> OTHER INFORMATION: primer

<400> SEQUENCE: 43
ccgtatagga ggtcagcatt g                                                  21

<210> SEQ ID NO 44
<211> LENGTH: 22
<212> TYPE: DNA
<213> ORGANISM: Artificial
<220> FEATURE:
<223> OTHER INFORMATION: primer

<400> SEQUENCE: 44
cataaggcca agggatgcta tg                                                 22

<210> SEQ ID NO 45
<211> LENGTH: 23
<212> TYPE: DNA
<213> ORGANISM: Artificial
<220> FEATURE:
<223> OTHER INFORMATION: primer

<400> SEQUENCE: 45
ctccttcttt cgtagtatgg gtc                                                23

<210> SEQ ID NO 46
<211> LENGTH: 23
<212> TYPE: DNA
<213> ORGANISM: Artificial
<220> FEATURE:
```

<223> OTHER INFORMATION: primer

<400> SEQUENCE: 46
ccaatacagc tttgcatcag aag                                          23

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
taacggagcc attccaagtc                                              20

<210> SEQ ID NO 48
<211> LENGTH: 22
<212> TYPE: DNA
<213> ORGANISM: Artificial
<220> FEATURE:
<223> OTHER INFORMATION: primer

<400> SEQUENCE: 48
ctggaactgt atcgacacag ag                                           22

<210> SEQ ID NO 49
<211> LENGTH: 23
<212> TYPE: DNA
<213> ORGANISM: Artificial
<220> FEATURE:
<223> OTHER INFORMATION: primer

<400> SEQUENCE: 49
ctcttctgta agcctctttc gag                                          23

<210> SEQ ID NO 50
<211> LENGTH: 22
<212> TYPE: DNA
<213> ORGANISM: Artificial
<220> FEATURE:
<223> OTHER INFORMATION: primer

<400> SEQUENCE: 50
acggtgaggt taaggatgct ag                                           22

<210> SEQ ID NO 51
<211> LENGTH: 21
<212> TYPE: DNA
<213> ORGANISM: Artificial
<220> FEATURE:
<223> OTHER INFORMATION: primer

<400> SEQUENCE: 51
caaggaggta gaggtggagt g                                            21

<210> SEQ ID NO 52
<211> LENGTH: 22
<212> TYPE: DNA
<213> ORGANISM: Artificial
<220> FEATURE:
<223> OTHER INFORMATION: primer

<400> SEQUENCE: 52
gaaatactcg agcttggaga gg                                           22

```
<210> SEQ ID NO 53
<211> LENGTH: 23
<212> TYPE: DNA
<213> ORGANISM: Artificial
<220> FEATURE:
<223> OTHER INFORMATION: primer

<400> SEQUENCE: 53
caacggtaac ctcaataggt tcc                                              23

<210> SEQ ID NO 54
<211> LENGTH: 21
<212> TYPE: DNA
<213> ORGANISM: Artificial
<220> FEATURE:
<223> OTHER INFORMATION: primer

<400> SEQUENCE: 54
gatctaaagc tggcagacat c                                                21

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
ccaggatggc tcatctcaac                                                  20

<210> SEQ ID NO 56
<211> LENGTH: 21
<212> TYPE: DNA
<213> ORGANISM: Artificial
<220> FEATURE:
<223> OTHER INFORMATION: primer

<400> SEQUENCE: 56
gttgcggagt tcgataagac c                                                21

<210> SEQ ID NO 57
<211> LENGTH: 23
<212> TYPE: DNA
<213> ORGANISM: Artificial
<220> FEATURE:
<223> OTHER INFORMATION: primer

<400> SEQUENCE: 57
cctcatccac aactactctc ttg                                              23

<210> SEQ ID NO 58
<211> LENGTH: 22
<212> TYPE: DNA
<213> ORGANISM: Artificial
<220> FEATURE:
<223> OTHER INFORMATION: primer

<400> SEQUENCE: 58
ttgaagatgg ctaaggagtt gg                                               22

<210> SEQ ID NO 59
<211> LENGTH: 21
<212> TYPE: DNA
<213> ORGANISM: Artificial
<220> FEATURE:
<223> OTHER INFORMATION: primer
```

```
<400> SEQUENCE: 59
cggttctcca atcacaacat c                                       21

<210> SEQ ID NO 60
<211> LENGTH: 24
<212> TYPE: DNA
<213> ORGANISM: Artificial
<220> FEATURE:
<223> OTHER INFORMATION: primer

<400> SEQUENCE: 60
aaaacagata tccgaaatac tcga                                    24

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
ggttatctcc caatcttatc cct                                     23

<210> SEQ ID NO 62
<211> LENGTH: 24
<212> TYPE: DNA
<213> ORGANISM: Artificial
<220> FEATURE:
<223> OTHER INFORMATION: primer

<400> SEQUENCE: 62
acgaggcaat aaagttcgac gcaa                                    24

<210> SEQ ID NO 63
<211> LENGTH: 24
<212> TYPE: DNA
<213> ORGANISM: Artificial
<220> FEATURE:
<223> OTHER INFORMATION: primer

<400> SEQUENCE: 63
taagatcttc cttatcagag agct                                    24

<210> SEQ ID NO 64
<211> LENGTH: 24
<212> TYPE: DNA
<213> ORGANISM: Artificial
<220> FEATURE:
<223> OTHER INFORMATION: primer

<400> SEQUENCE: 64
gagattgtca agagactcta tgat                                    24

<210> SEQ ID NO 65
<211> LENGTH: 24
<212> TYPE: DNA
<213> ORGANISM: Artificial
<220> FEATURE:
<223> OTHER INFORMATION: primer

<400> SEQUENCE: 65
tctgtggtct tatcgaactc cgca                                    24

<210> SEQ ID NO 66
<211> LENGTH: 24
```

```
<212> TYPE: DNA
<213> ORGANISM: Artificial
<220> FEATURE:
<223> OTHER INFORMATION: primer

<400> SEQUENCE: 66
tacttgggca gataaaattg gaag                                          24

<210> SEQ ID NO 67
<211> LENGTH: 24
<212> TYPE: DNA
<213> ORGANISM: Artificial
<220> FEATURE:
<223> OTHER INFORMATION: primer

<400> SEQUENCE: 67
agcatcttgc ttgcaatttc ctct                                          24

<210> SEQ ID NO 68
<211> LENGTH: 24
<212> TYPE: DNA
<213> ORGANISM: Artificial
<220> FEATURE:
<223> OTHER INFORMATION: primer

<400> SEQUENCE: 68
agtcgtctta aagggagacc aact                                          24

<210> SEQ ID NO 69
<211> LENGTH: 24
<212> TYPE: DNA
<213> ORGANISM: Artificial
<220> FEATURE:
<223> OTHER INFORMATION: primer

<400> SEQUENCE: 69
atctctttaa catccttctt gctt                                          24

<210> SEQ ID NO 70
<211> LENGTH: 28
<212> TYPE: DNA
<213> ORGANISM: Artificial
<220> FEATURE:
<223> OTHER INFORMATION: primer

<400> SEQUENCE: 70
agggagacca actccccagg gaaatatt                                      28

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
ttgattatct ctttaacatc cttcttgctt                                    30

<210> SEQ ID NO 72
<211> LENGTH: 24
<212> TYPE: DNA
<213> ORGANISM: Artificial
<220> FEATURE:
<223> OTHER INFORMATION: primer

<400> SEQUENCE: 72
```
actccccagg gaaatattgg aggt                                          24

<210> SEQ ID NO 73
<211> LENGTH: 24
<212> TYPE: DNA
<213> ORGANISM: Artificial
<220> FEATURE:
<223> OTHER INFORMATION: primer

<400> SEQUENCE: 73
ctttaacatc cttcttgctt aggg                                          24

<210> SEQ ID NO 74
<211> LENGTH: 29
<212> TYPE: DNA
<213> ORGANISM: Artificial
<220> FEATURE:
<223> OTHER INFORMATION: primer

<400> SEQUENCE: 74
gaaatatgga ggtggctgaa tgattgtac                                     29

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
cttcttgctt aggggggtgct ttatcttgag                                   30

<210> SEQ ID NO 76
<211> LENGTH: 30
<212> TYPE: DNA
<213> ORGANISM: Artificial
<220> FEATURE:
<223> OTHER INFORMATION: primer

<400> SEQUENCE: 76
aggtggctga atgattgtac tagcgttgga                                    30

<210> SEQ ID NO 77
<211> LENGTH: 30
<212> TYPE: DNA
<213> ORGANISM: Artificial
<220> FEATURE:
<223> OTHER INFORMATION: primer

<400> SEQUENCE: 77 aggggggtgct ttatcttgag ctccattctt                                   30

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
atgattgtac tagcgttgga cgtgtatgag                                    30

<210> SEQ ID NO 79
<211> LENGTH: 30
<212> TYPE: DNA
<213> ORGANISM: Artificial

```
<220> FEATURE:
<223> OTHER INFORMATION: primer

<400> SEQUENCE: 79
ttatcttgag ctccattctt tcacctcctc                                        30

<210> SEQ ID NO 80
<211> LENGTH: 39
<212> TYPE: DNA
<213> ORGANISM: Artificial
<220> FEATURE:
<223> OTHER INFORMATION: primer

<400> SEQUENCE: 80
agagagaggc atgccaccta cctcctatat tgttccatg                              39

<210> SEQ ID NO 81
<211> LENGTH: 39
<212> TYPE: DNA
<213> ORGANISM: Artificial
<220> FEATURE:
<223> OTHER INFORMATION: primer

<400> SEQUENCE: 81
gagagagggc gcgccgtcaa gaggatgatt aggtagagc                              39

<210> SEQ ID NO 82
<211> LENGTH: 26
<212> TYPE: DNA
<213> ORGANISM: Artificial
<220> FEATURE:
<223> OTHER INFORMATION: primer

<400> SEQUENCE: 82
tcaaatgctc atcatttagt tttatg                                            26

<210> SEQ ID NO 83
<211> LENGTH: 28
<212> TYPE: DNA
<213> ORGANISM: Artificial
<220> FEATURE:
<223> OTHER INFORMATION: primer

<400> SEQUENCE: 83
aatgagcatg cgttataaac acattctc                                          28

<210> SEQ ID NO 84
<211> LENGTH: 28
<212> TYPE: DNA
<213> ORGANISM: Artificial
<220> FEATURE:
<223> OTHER INFORMATION: primer

<400> SEQUENCE: 84
aagctctaga aaagatattg gaggttcc                                          28

<210> SEQ ID NO 85
<211> LENGTH: 53
<212> TYPE: DNA
<213> ORGANISM: Artificial
<220> FEATURE:
<223> OTHER INFORMATION: primer

<400> SEQUENCE: 85
ttaatatgcc caggcctact cctttgccgt catcacccat atgatcgtga gtc              53
```

<210> SEQ ID NO 86
<211> LENGTH: 60
<212> TYPE: DNA
<213> ORGANISM: Artificial
<220> FEATURE:
<223> OTHER INFORMATION: primer

<400> SEQUENCE: 86
aggagtaggc ctgggcatat taacgtgctg actgatagag gattagctaa gcttgaactc    60

<210> SEQ ID NO 87
<211> LENGTH: 56
<212> TYPE: DNA
<213> ORGANISM: Artificial
<220> FEATURE:
<223> OTHER INFORMATION: primer

<400> SEQUENCE: 87
aggagtaggc ctgggcatat taacgtgctg actgattgaa aatggagtga gctgag    56

<210> SEQ ID NO 88
<211> LENGTH: 58
<212> TYPE: DNA
<213> ORGANISM: Artificial
<220> FEATURE:
<223> OTHER INFORMATION: primer

<400> SEQUENCE: 88
ttaatatgcc caggcctact cctttgccgt gattttatct tgagctccat tctttcac    58

<210> SEQ ID NO 89
<211> LENGTH: 19
<212> TYPE: DNA
<213> ORGANISM: Artificial
<220> FEATURE:
<223> OTHER INFORMATION: primer

<400> SEQUENCE: 89
actgccagca tgctcgtag    19

<210> SEQ ID NO 90
<211> LENGTH: 26
<212> TYPE: DNA
<213> ORGANISM: Artificial
<220> FEATURE:
<223> OTHER INFORMATION: primer

<400> SEQUENCE: 90
agatgctagc gaagggatg aagttg    26

<210> SEQ ID NO 91
<211> LENGTH: 59
<212> TYPE: DNA
<213> ORGANISM: Artificial
<220> FEATURE:
<223> OTHER INFORMATION: primer

<400> SEQUENCE: 91
ttcgtgttat gatgcccact aagcgtctgc tcgaccttca gatttcaaaa ccctcatag    59

<210> SEQ ID NO 92
<211> LENGTH: 50
<212> TYPE: DNA
<213> ORGANISM: Artificial
<220> FEATURE:
<223> OTHER INFORMATION: primer -continued

<400> SEQUENCE: 92
ttagtgggca tcataacacg aaagagagtg attagagcct gtcgtagacc           50

<210> SEQ ID NO 93
<211> LENGTH: 56
<212> TYPE: DNA
<213> ORGANISM: Artificial
<220> FEATURE:
<223> OTHER INFORMATION: primer

<400> SEQUENCE: 93
acgcttagtg ggcatcataa cacgaaagag agtgattgaa aatggagtga gctgag    56

<210> SEQ ID NO 94
<211> LENGTH: 58
<212> TYPE: DNA
<213> ORGANISM: Artificial
<220> FEATURE:
<223> OTHER INFORMATION: primer

<400> SEQUENCE: 94
tgttatgatg cccactaagc gtctgctcgg attttatctt gagctccatt ctttcacc  58

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
aagagaagtc ggcaattcac                                            20

<210> SEQ ID NO 96
<211> LENGTH: 53
<212> TYPE: DNA
<213> ORGANISM: Artificial
<220> FEATURE:
<223> OTHER INFORMATION: primer

<400> SEQUENCE: 96
acgaaaccgg gtctcggcgt aacacgctca cttcaccaaa ccacattttt ggc       53

<210> SEQ ID NO 97
<211> LENGTH: 56
<212> TYPE: DNA
<213> ORGANISM: Artificial
<220> FEATURE:
<223> OTHER INFORMATION: primer

<400> SEQUENCE: 97
tgttacgccg agacccggtt tcgtctctca tttagggatc taaaattttg taaaac    56

<210> SEQ ID NO 98
<211> LENGTH: 21
<212> TYPE: DNA
<213> ORGANISM: Artificial
<220> FEATURE:
<223> OTHER INFORMATION: primer

<400> SEQUENCE: 98
tagggagtat aagagaagag c                                          21

<210> SEQ ID NO 99

```
<211> LENGTH: 54
<212> TYPE: DNA
<213> ORGANISM: Artificial
<220> FEATURE:
<223> OTHER INFORMATION: primer

<400> SEQUENCE: 99
tgttacgccg agacccggtt tcgtctctca tgattgaaaa tggagtgagc tgag          54

<210> SEQ ID NO 100
<211> LENGTH: 59
<212> TYPE: DNA
<213> ORGANISM: Artificial
<220> FEATURE:
<223> OTHER INFORMATION: primer

<400> SEQUENCE: 100
aaaccgggtc tcggcgtaac acgctcactt gattttatct tgagctccat tctttcacc    59

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101
ccaaaccaca tttcagttca cctccgcctt                                    30

<210> SEQ ID NO 102
<211> LENGTH: 30
<212> TYPE: DNA
<213> ORGANISM: Artificial
<220> FEATURE:
<223> OTHER INFORMATION: primer

<400> SEQUENCE: 102
gtgaactgaa atgtggtttg gtgagtttgg                                    30

<210> SEQ ID NO 103
<211> LENGTH: 35
<212> TYPE: DNA
<213> ORGANISM: Artificial
<220> FEATURE:
<223> OTHER INFORMATION: primer

<400> SEQUENCE: 103 ctaaaaaga ttttagatcc ctaaaagttc ctcta                               35

<210> SEQ ID NO 104
<211> LENGTH: 40
<212> TYPE: DNA
<213> ORGANISM: Artificial
<220> FEATURE:
<223> OTHER INFORMATION: primer

<400> SEQUENCE: 104
aagtgagcgt gttacgccga gacccggttt cgtctctcat                         40

<210> SEQ ID NO 105

<400> SEQUENCE: 105

000

<210> SEQ ID NO 106
```

<400> SEQUENCE: 106

000

<210> SEQ ID NO 107
<211> LENGTH: 26
<212> TYPE: DNA
<213> ORGANISM: Artificial
<220> FEATURE:
<223> OTHER INFORMATION: primer

<400> SEQUENCE: 107
agagaggatt cacggtacca tctttt                                        26

<210> SEQ ID NO 108
<211> LENGTH: 28
<212> TYPE: DNA
<213> ORGANISM: Artificial
<220> FEATURE:
<223> OTHER INFORMATION: primer

<400> SEQUENCE: 108
acgtttccat cttttataa ctctcgtg                                       28

<210> SEQ ID NO 109
<211> LENGTH: 27
<212> TYPE: DNA
<213> ORGANISM: Artificial
<220> FEATURE:
<223> OTHER INFORMATION: primer

<400> SEQUENCE: 109
aggtaccggt tcatgtgcag ctccatc                                       27

<210> SEQ ID NO 110
<211> LENGTH: 21
<212> TYPE: DNA
<213> ORGANISM: Artificial
<220> FEATURE:
<223> OTHER INFORMATION: primer

<400> SEQUENCE: 110
ctccaacgtc atctcgttct c                                             21

<210> SEQ ID NO 111
<211> LENGTH: 17
<212> TYPE: DNA
<213> ORGANISM: Artificial
<220> FEATURE:
<223> OTHER INFORMATION: primer

<400> SEQUENCE: 111
tcaccagctc cgcgaag                                                  17

<210> SEQ ID NO 112
<211> LENGTH: 26
<212> TYPE: DNA
<213> ORGANISM: Artificial
<220> FEATURE:
<223> OTHER INFORMATION: primer

<400> SEQUENCE: 112
tctctctatc gattcaccag ctccgc                                        26

<210> SEQ ID NO 113

```
<211> LENGTH: 21
<212> TYPE: DNA
<213> ORGANISM: Artificial
<220> FEATURE:
<223> OTHER INFORMATION: primer

<400> SEQUENCE: 113
agtacatcac cgacgagcaa g                                          21

<210> SEQ ID NO 114
<211> LENGTH: 31
<212> TYPE: DNA
<213> ORGANISM: Artificial
<220> FEATURE:
<223> OTHER INFORMATION: primer

<400> SEQUENCE: 114
aaaaggatcc agtacatcac cgacgagcaa g                               31

<210> SEQ ID NO 115
<211> LENGTH: 21
<212> TYPE: DNA
<213> ORGANISM: Artificial
<220> FEATURE:
<223> OTHER INFORMATION: primer

<400> SEQUENCE: 115
actttgtagc tgcaaaccac c                                          21

<210> SEQ ID NO 116
<211> LENGTH: 31
<212> TYPE: DNA
<213> ORGANISM: Artificial
<220> FEATURE:
<223> OTHER INFORMATION: primer

<400> SEQUENCE: 116
aaaaatcgat actttgtagc tgcaaaccac c                               31

<210> SEQ ID NO 117
<211> LENGTH: 23
<212> TYPE: DNA
<213> ORGANISM: Artificial
<220> FEATURE:
<223> OTHER INFORMATION: primer

<400> SEQUENCE: 117
tccattggaa attgtgctcc tag                                        23

<210> SEQ ID NO 118
<211> LENGTH: 33
<212> TYPE: DNA
<213> ORGANISM: Artificial
<220> FEATURE:
<223> OTHER INFORMATION: primer

<400> SEQUENCE: 118
aaaaggatcc tccattggaa attgtgctcc tag                             33

<210> SEQ ID NO 119
<211> LENGTH: 18
<212> TYPE: DNA
<213> ORGANISM: Artificial
<220> FEATURE:
<223> OTHER INFORMATION: primer

<400> SEQUENCE: 119
```
agggtagtgg caccaagg                                                    18

<210> SEQ ID NO 120
<211> LENGTH: 27
<212> TYPE: DNA
<213> ORGANISM: Artificial
<220> FEATURE:
<223> OTHER INFORMATION: primer

<400> SEQUENCE: 120
agtattctct caagagatag taggcag                                          27

<210> SEQ ID NO 121
<211> LENGTH: 31
<212> TYPE: DNA
<213> ORGANISM: Artificial
<220> FEATURE:
<223> OTHER INFORMATION: primer

<400> SEQUENCE: 121
aaaaggatcc gacaaacact ctcccatatt a                                     31

<210> SEQ ID NO 122
<211> LENGTH: 33
<212> TYPE: DNA
<213> ORGANISM: Artificial
<220> FEATURE:
<223> OTHER INFORMATION: primer

<400> SEQUENCE: 122
aaaaggatcc taaacagaag tgaagtcccc cag                                   33

<210> SEQ ID NO 123
<211> LENGTH: 32
<212> TYPE: DNA
<213> ORGANISM: Artificial
<220> FEATURE:
<223> OTHER INFORMATION: primer

<400> SEQUENCE: 123
aaaaggatcc ttcctgtgga gacaaaatga ac                                    32

<210> SEQ ID NO 124
<211> LENGTH: 38
<212> TYPE: DNA
<213> ORGANISM: Artificial
<220> FEATURE:
<223> OTHER INFORMATION: primer

<400> SEQUENCE: 124
aaaaggatcc tttttatcct ttgcttgaca aaaacatg                              38

<210> SEQ ID NO 125
<211> LENGTH: 31
<212> TYPE: DNA
<213> ORGANISM: Artificial
<220> FEATURE:
<223> OTHER INFORMATION: primer

<400> SEQUENCE: 125
aaaaggatcc tttccagagg aaacataaca c                                     31

<210> SEQ ID NO 126
<211> LENGTH: 35
<212> TYPE: DNA

```
<213> ORGANISM: Artificial
<220> FEATURE:
<223> OTHER INFORMATION: primer

<400> SEQUENCE: 126
aaaaatcgat ttgaaaggta agcaattttc acgag                              35

<210> SEQ ID NO 127
<211> LENGTH: 38
<212> TYPE: DNA
<213> ORGANISM: Artificial
<220> FEATURE:
<223> OTHER INFORMATION: primer

<400> SEQUENCE: 127
aaaaatcgat ctaatgaaca tttattcagt aattagcc                           38

<210> SEQ ID NO 128
<211> LENGTH: 32
<212> TYPE: DNA
<213> ORGANISM: Artificial
<220> FEATURE:
<223> OTHER INFORMATION: primer

<400> SEQUENCE: 128
aaaaatcgat ggttccagtg gaaatgaaac tc                                 32

<210> SEQ ID NO 129
<211> LENGTH: 33
<212> TYPE: DNA
<213> ORGANISM: Artificial
<220> FEATURE:
<223> OTHER INFORMATION: primer

<400> SEQUENCE: 129
aaaaatcgat taatctaatg aactaaaagg tgc                                33

<210> SEQ ID NO 130
<211> LENGTH: 34
<212> TYPE: DNA
<213> ORGANISM: Artificial
<220> FEATURE:
<223> OTHER INFORMATION: primer

<400> SEQUENCE: 130
atatatcgat cattttgtct ccacaggaaa tctg                               34

<210> SEQ ID NO 131
<211> LENGTH: 23
<212> TYPE: DNA
<213> ORGANISM: Artificial
<220> FEATURE:
<223> OTHER INFORMATION: primer

<400> SEQUENCE: 131
gattgaaaat ggagtgagct gag                                           23

<210> SEQ ID NO 132
<211> LENGTH: 22
<212> TYPE: DNA
<213> ORGANISM: Artificial
<220> FEATURE:
<223> OTHER INFORMATION: primer

<400> SEQUENCE: 132
gttcatccct ccaaattagg tg                                            22
```

```
<210> SEQ ID NO 133
<211> LENGTH: 12
<212> TYPE: DNA
<213> ORGANISM: pyrococcus furiosus

<400> SEQUENCE: 133
atatttaaat at                                                        12

<210> SEQ ID NO 134
<211> LENGTH: 10
<212> TYPE: DNA
<213> ORGANISM: pyrococcus furiosus

<400> SEQUENCE: 134
tatttaaata                                                           10

<210> SEQ ID NO 135
<211> LENGTH: 10
<212> TYPE: DNA
<213> ORGANISM: pyrococcus furiosus

<400> SEQUENCE: 135
tatttaaata                                                           10

<210> SEQ ID NO 136
<211> LENGTH: 16
<212> TYPE: DNA
<213> ORGANISM: pyrococcus furiosus

<400> SEQUENCE: 136
attagattaa tctaat                                                    16

<210> SEQ ID NO 137
<211> LENGTH: 16
<212> TYPE: DNA
<213> ORGANISM: pyrococcus furiosus

<400> SEQUENCE: 137
attaagttaa cctaat                                                    16

<210> SEQ ID NO 138
<211> LENGTH: 16
<212> TYPE: DNA
<213> ORGANISM: pyrococcus furiosus

<400> SEQUENCE: 138
attaagttaa cttaat                                                    16

<210> SEQ ID NO 139
<211> LENGTH: 33
<212> TYPE: DNA
<213> ORGANISM: Artificial
<220> FEATURE:
<223> OTHER INFORMATION: primer

<400> SEQUENCE: 139
cccccagagt ttcatttcca ctggaaccag gtt                                 33

<210> SEQ ID NO 140
<211> LENGTH: 33
<212> TYPE: DNA
<213> ORGANISM: Artificial
<220> FEATURE:
```

```
-continued

<223> OTHER INFORMATION: primer

<400> SEQUENCE: 140
cccccagagt tcatttcca ctggagccag gtt                              33

<210> SEQ ID NO 141
<211> LENGTH: 23
<212> TYPE: DNA
<213> ORGANISM: Artificial
<220> FEATURE:
<223> OTHER INFORMATION: primer

<400> SEQUENCE: 141
agagagtttt atttccactg gaa                                        23
```

PYROCOCCUS FURIOSUS STRAINS AND METHODS OF USING SAME

CROSS-REFERENCE TO RELATED APPLICATIONS

This application claims the benefit of U.S. Provisional Application Ser. No. 61/387,656, filed Sep. 29, 2010, which is incorporated by reference herein.

GOVERNMENT FUNDING

The present invention was made with government support under Grant No. DE-FG05-95ER20175 and Grant No. DE-FG-02-08ER64690, both awarded by the Department of Energy. The Government has certain rights in this invention.

BACKGROUND

It would be difficult to overestimate the contribution of genetic manipulation to the study of any biological system, and it is an essential tool for the metabolic engineering of biosynthetic and substrate utilization pathways. This is particularly true for the archaea since, in spite of their environmental and industrial importance, coupled with their unique molecular features, much remains to be learned about their biology (Allers and Mevarech, 2005 Nat. Rev. Genet. 6:58-73). The marine hyperthermophilic anaerobe *Pyrococcus furiosus* is of special interest not only for its ability to grow optimally at 100° C. and the implications of this trait for its biology but also for industrial applications of its enzymes, as well as its capacity to produce hydrogen efficiently (Atomi, 2005 Curr. Opin. Chem. Biol. 9:166-173; Egorova and Antranikian, 2005 Curr. Opin. Microbiol. 8:649-655; Verhaart et al., 2010 Environ. Technol. 31:993-1003).

The development of genetic systems in the archaea, in general, presents many unique challenges given the extreme growth requirements of many of these organisms. To date, genetic systems of various levels of sophistication have been developed for representatives of all major groups of archaea, including halophiles, methanogens, thermoacidophiles, and hyperthermophiles (Allers and Mevarech, 2005 Nat. Rev. Genet. 6:58-73; Berkner and Lipps, 2008 Arch. Microbiol. 190:217-230; Rother and Metcalf, 2005 Curr. Opin. Microbiol. 8:745-751; Soppa, 2006 Microbiology 152:585-590; Tumbula and Whitman, 1999 Mol. Microbiol. 33:1-7; Wagner et al., 2009 Biochem. Soc. Trans. 37:97-101). A variety of transormation methods are being used, including electroporation, heat shock with or without $CaCl_2$ treatment, phage-mediated transduction, spheroplast transformation, liposomes, and, very recently, even conjugation with *Escherichia coli* (Allers and Mevarech, 2005 Nat. Rev. Genet. 6:58-73; Dodsworth et al., 2010 Appl. Environ. Microbiol. 76:5644-5647). Transformation via natural competence has been reported in three archaeal species, in comparison to over 60 bacterial species that are known to exhibit this trait (Johnsborg et al., 2007 Res. Microbiol. 158:767-778; Sato et al., 2003 J. Bacteriol. 185:210-220). Two of them are the methanogens *Methanococcus voltae* PS (Bertani and Baresi, 1987 J. Bacteriol. 169:2730-2738; Patel et al., 1994 Appl. Environ. Microbiol. 60:903-907) and *Methanobacterium thermoautotrophicum* Marburg (Worrell et al., 1988 J. Bacteriol. 170:653-656); however, transformation frequencies were low, and there have been no follow-up studies regarding natural competence. The other is the hyperthermophile *Thermococcus kodakarensis*, which has an optimal growth temperature of 85° C. Its natural competence has enabled the development of genetic tools for targeted gene deletions, the use of shuttle vectors, and a reporter gene system (Santangelo et al., 2008 J. Bacteriol. 190:2244-2248; Santangelo et al., 2008 Appl. Environ. Microbiol. 74:3099-3104; Santangelo et al., 2010 Appl. Environ. Microbiol. 76:1044-1052; Sato et al., 2005 Appl. Environ. Microbiol. 71:3889-3899; Sato et al., 2003 J. Bacteriol. 185:210-220; Sato et al., 2004 J. Bacteriol. 186:5799-5807). In fact, *T. kodakarensis* was one of the first archaeal hyperthermophiles for which chromosomal manipulations were reported (Sato et al., 2003 J. Bacteriol. 185:210-220), along with *Sulfolobus solfataricus*, for which a transformation system with accompanying shuttle vectors had previously been established (Berkner and Lipps, 2008 Arch. Microbiol. 190:217-230; Worthington et al., 2003 J. Bacteriol. 185:482-488). *Sulfolobus* sp., *Thermococcus kodakaraensis*, and *Pyrococcus furiosus* are all transformed by linear DNA fragments (Deng et al., 2009 Extremophiles 13:735-46; Grogan and Stengel, 2008 Mol. Microbiol. 69:1255-1265; Kurosawa and Grogan, 2005 FEMS Microbiol. Lett. 253:141-9; Sato et al., 2003 J. Bacteriol. 185:210-220; Sato et al., 2005 Appl. Environ. Microbiol. 71:3889-3899; Lipscomb et al., 2011 Appl. Environ. Microbiol. 77:2232-8 (Example I)) and the limits of homology needed for marker replacement by linear DNA varies. In *T. kodakaraensis* more than 100 bp of homologous flanking region is required for homologous recombination (Sato et al., 2005 Appl. Environ. Microbiol. 71:3889-3899), and *S. acidocaldarius* 10-30 bp of homology is sufficient (Kurosawa and Grogan, 2005 FEMS Microbiol. Lett. 253:141-9).

One of the most significant barriers to genetic manipulation of archaea, in general, and hyperthermophiles, in particular, is the lack of selectable markers. Antibiotic selection strategies used in mesophilic bacteria are typically ineffective because the molecular machineries of archaea are not affected by the antibiotic (Cammarano et al., 1985 EMBO J. 4:811-816; Possot et al., 1988 Appl. Environ. Microbiol. 54:734-740) or, in the case of hyperthermophiles, because of the instability of either the drug or the heterologously expressed resistance protein at high temperatures (Allers and Mevarech, 2005 Nat. Rev. Genet. 6:58-73; Noll and Vargas, 1997 Arch. Microbiol. 168:73-80). One exception is the drug simvastatin (or mevinolin), first used in the haloarchaea (Lam and Doolittle, 1989 Proc. Natl. Acad. Sci. U.S.A. 86:5478-5482; Peck et al., 2000 Mol. Microbiol. 35:667-676), which is sufficiently thermostable to inhibit growth of both *T. kodakarensis* (85° C.) (Matsumi et al., 2007 J. Bacteriol. 189:2683-2691) and *P. furiosus* (Waege et al., 2010 Appl. Environ. Microbiol. 76:3308-3313). Simvastatin competitively inhibits 3-hydroxy-3-methylglutaryl coenzyme A (HMG-CoA) reductase, which converts HMG-CoA to mevalonate, the rate-limiting step in the biosynthesis of isoprenoids, the major component of archaeal membrane lipids. Simvastatin at sufficiently high concentrations leads to cessation of cell growth, while overexpression of HMG-CoA reductase confers resistance (Lam and Doolittle, 1989 Proc. Natl. Acad. Sci. U.S.A. 86:5478-5482; Matsumi et al., 2007 J. Bacteriol. 189:2683-2691).

Nutritional markers are especially useful for genetic selection if an organism is able to grow on a defined medium, and a number of such nutritional selections have been used in archaea, including auxotrophies for amino acids (e.g., leucine and tryptophan) (Allers et al., 2004 Appl. Environ. Microbiol. 70:943-953; Sato et al., 2003 J. Bacteriol. 185:210-220), thymidine (Allers et al., 2004 Appl. Environ. Microbiol. 70:943-953; Ortenberg et al., 2000 Mol. Microbiol. 35:1493-1505), and agmatine (Santangelo et al., 2010 Appl. Environ. Microbiol. 76:1044-1052; Santangelo and Reeve, 2011, In:

Extremophiles Handbook, Horikoshi (ed.), Springer, Chapter 4.8, pages 567-582). A counterselectable marker based on loss of the uracil biosynthetic enzyme orotidine-5'-monophosphate (OMP) decarboxylase, first described in yeast (*Saccharomyces cerevisiae*) (Boeke et al., 1984 Mol. Gen. Genet. 197:345-346), has been used successfully in archaeal organisms, including *T. kodakarensis* (Lucas et al., 2002 Appl. Environ. Microbiol. 68:5528-5536; Peck et al., 2000 Mol. Microbiol. 35:667-676; Sato et al., 2005 Appl. Environ. Microbiol. 71:3889-3899; Sato et al., 2003 J. Bacteriol. 185: 210-220). OMP decarboxylase (pyrF in archaea and bacteria) converts the pyrimidine analog 5-fluoroorotic acid (5-FOA) to fluorodeoxyuridine, a toxic product that kills growing cells (Boeke et al., 1984 Mol. Gen. Genet. 197:345-346). Mutations in pyrF result in uracil auxotrophs that are resistant to 5-FOA.

SUMMARY OF THE INVENTION

Provided herein are methods for transforming a *Pyrococcus furiosus* with a polynucleotide. In one embodiment, the method includes contacting a *P. furiosus* with a polynucleotide under conditions suitable for uptake of the polynucleotide by the *P. furiosus*, and identifying transformants. The number of transformants may be, for instance, at least $10^3$ transformants are obtained per microgram DNA, at least $10^4$ transformants are obtained per microgram DNA, or at least $10^5$ transformants are obtained per microgram DNA. The polynucleotide may be linear or circular. In one embodiment, the polynucleotide is DNA. The introduced polynucleotide may or may not be integrated into the recipient's genomic DNA.

In one embodiment, the polynucleotide includes one or more homology regions to facilitate homologous recombination between the introduced polynucleotide and the recipient's genomic DNA. In one embodiment, the polynucleotide does not include any homology regions, and such a polynucleotide will not undergo homologous recombination with the recipient's genomic DNA.

In one embodiment, the polynucleotide is linear and includes an intervening region flanked by a first homology region and a second homology region. The first homology region and the second homology region each include nucleotide sequences that are homologous to nucleotide sequences present in the *P. furiosus* chromosome. The first homology region and the second homology region may be at least 20 nucleotides in length.

In one embodiment, the polynucleotide is a circular polynucleotide and includes a homology region that includes a nucleotide sequence that is homologous to a nucleotide sequence present in the *P. furiosus* genome. The homology region may be at least 20 nucleotides in length. In another embodiment, the polynucleotide is circular and includes a first homology region and a second homology region, wherein each nucleotide sequence is homologous to a nucleotide sequence present in the *P. furiosus* chromosome. The first homology region and the second homology region may be at least 20 nucleotides in length.

In one embodiment, the method does not include exposing the recipient to conditions that include heat shock, $CaCl_2$, an applied electrical field, a liposome, a phage, or conditions resulting in spheroplast formation.

In one embodiment, the method includes contacting a *P. furiosus* with a polynucleotide under conditions suitable for uptake of the polynucleotide by the *P. furiosus*, and identifying transformants, wherein the polynucleotide includes at least one homology region, wherein the homology region includes a nucleotide sequence that is homologous to a nucleotide sequence present in the *P. furiosus* chromosome, and wherein the homology region is at least 20 nucleotides in length.

Provided herein is an isolated *Pyrococcus furiosus* having the characteristics of *Pyrococcus furiosus* COM1 deposited with the American Type Culture Collection in accordance with the provisions of the Budapest Treaty, wherein the isolated *Pyrococcus furiosus* transforms at a frequency of at least of $10^3$ transformants per microgram DNA. Also provided herein is an isolated *Pyrococcus furiosus* COM1 deposited with the American Type Culture Collection in accordance with the provisions of the Budapest Treaty. An isolated *Pyrococcus furiosus* provided herein may include a heterologous polynucleotide. In one embodiment, the heterologous polynucleotide may be integrated into the *P. furiosus* genomic DNA. In one embodiment, the heterologous polynucleotide is not integrated into the *P. furiosus* genomic DNA.

Also provided herein is a plasmid that includes an origin of replication that functions in a *Pyrococcus furiosus*, wherein the plasmid is stable in a recipient *P. furiosus* without selection for more than 100 generations and is structurally unchanged after replication in *P. furiosus* for more than 100 generations.

Competence is the ability of a recipient strain to transport DNA from outside the cell into the cell. As used herein, a "highly competent" *P. furiosus* is a *P. furiosus* that can take up DNA, and optionally integrate DNA, at a frequency that is higher than wild type *P. furiosus* strains, such as DSM3638. In one embodiment, a "highly competent" *P. furiosus* take up DNA, and optionally integrate DNA, at a frequency of at least $10^3$ transformants per microgram of DNA, at least $10^4$ transformants per microgram of DNA, at least $10^5$ transformants per microgram of DNA, or at least $10^6$ transformants per microgram of DNA. A "highly competent" *P. furiosus* is transformed at a frequency that is higher than wild type *P. furiosus* strains, such as DSM3638.

As used herein, "transformation" refers to a polynucleotide transfer process in which a polynucleotide is taken up by a recipient cell. A recipient cell that contains the polynucleotide, or a portion thereof, is referred to as a transformant. The polynucleotide taken up by the recipient may or may not be integrated into the recipient's genome, such as its chromosome.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology.

As used herein, a "heterologous polynucleotide" refers to a polynucleotide that is not normally or naturally found in a microbe. A "heterologous polynucleotide" also includes a polynucleotide that is present in a *P. furiosus* by introduction into the *P. furiosis* as described herein. An "endogenous polypeptide" is also referred to as a "native polynucleotide."

A "coding region" is a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end As used herein, "homologous region" and "homology region" are used interchangeably and refer to a polynucleotide that may be present as part of a polynucleotide that is introduced into a recipient. A homologous region has a nucleotide sequence that is substantially similar or identical to a nucleotide sequence present in the genome, e.g., a chromosome, of the recipient, and permits homologous recombination to occur between the introduced polynucleotide and the recipient's genome.

Conditions that are "suitable" for an event to occur, such as transfer of a polynucleotide into a cell, or "suitable" conditions are conditions that do not prevent such events from occurring. Thus, these conditions permit, enhance, facilitate, and/or are conducive to the event.

As used herein, the term "polypeptide" refers broadly to a polymer of two or more amino acids joined together by peptide bonds. The term "polypeptide" also includes molecules which contain more than one polypeptide joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, an "exogenous polypeptide" refers to a polypeptide that is not normally or naturally found in a microbe. An exogenous polypeptide is encoded by a coding region that is not normally found in a microbe. An "endogenous polypeptide" is also referred to as a "native polynucleotide."

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 2A shows a diagram of the pyrF genome region is shown with the pyrF deletion plasmid having 1-kb regions from up- and downstream of pyrF for homologous recombination and also containing the $P_{gdh}$-hmg cassette for selection of simvastatin resistance. Homologous recombination can occur at the upstream or downstream pyrF flanking regions, integrating the plasmid into the genome and generating a strain that is simvastatin resistant. Selection on 5-FOA selects for loss of the plasmid along with deletion of the pyrF gene. Bent arrows depict primers used for verification of pyrF deletion. FIG. 2B shows a gel depicting PCR products of the pyrF genome region in the COM1 strain compared to the wild type, amplified by primers outside the up- and downstream regions used for homologous recombination (see bent arrows in panel A).

FIG. 3A shows diagrams of plasmid integration at homologous region upstream of pyrF, (top) downstream of pyrF (middle), and at hmg (bottom). The PCR products used to verify integration events are shown with a bold red line. FIG. 3B shows a gel showing PCR products indicated in A for simvastatin isolates 1 and 2 compared to wild type, demonstrating plasmid integration upstream of pyrF, downstream of pyrF, and at hmg. A PCR product can only be obtained in the event of an integration since primer pairs used contain one primer inside the plasmid and one primer within the genome and not in the plasmid.

FIG. 6A shows the SHI operon genome region with the SHI operon deletion plasmid with 1-kb regions from up- and downstream of the operon for homologous recombination and also containing the $P_{gdh}$-pyrF cassette for selection of uracil prototrophy. Homologous recombination can occur at either the upstream or downstream SHI operon flanking regions, integrating the plasmid into the genome and generating a strain that is a uracil prototroph. PF0891, PF0892, PF0893, and PF0894 represent the genes coding for the SHI beta, gamma, delta, and alpha subunits, respectively. FIG. 6B shows a gel depicting PCR products of the SHI and SHII operon genome regions in the ΔSHI, ΔSHII, and ΔSHI ΔSHII strains compared to the COM1 strain, amplified by primers with at least one primer outside the homologous recombination regions.

FIG. 11A shows 1 kb flanking regions are amplified from gDNA and $P_{gdh}$pyrF is amplified from pJFW017. Overlap tails for SOE PCR introduce the 'pop-out scar' sequence and are indicated in red. FIG. 11B shows SOE PCR generates two overlap products. FIG. 11C shows a second SOE PCR generates the final pop-out construct. FIG. 11D shows transformation into *P. furiosus* allows for selection of the marker replacement event. FIG. 11E shows 5-FOA selection of the pop-out cassette generates a markerless deletion.

FIG. 14 shows construction of pJFW027. A linear DNA fragment containing the entire sequence of pJFW017 was generated by PCR amplification using primers JF266 and JF267 and ligated into the origin fragment indicated in FIG. 13, also generated by PCR amplification using primers JF268 and JF282. Plasmids containing the various origin fragments described in the legend of FIG. 13 were cloned into pJFW017 for testing.

FIG. 15 shows that pJFW019 contains the pSC101 replication origin and aac gene cassette for replication and selection in *E. coli*. The pyrF gene, under control of the gdh promoter provides for uracil prototrophic selection in *P. furiosus*. The entire pGT5 sequence was used to promote plasmid replication in *P. furiosus*.

FIG. 18A shows a diagram of the chromosomal region, including the gdh open reading frame. HpaI sites are indicated, as are the locations of primers used to generate the gdh hybridization probe. FIG. 18 B shows a Southern blot of pJFW027 transformants. Lanes 1 to 10, DNA isolated from transformants and digested with HpaI; lanes 11 and 12, DNAs from *P. furiosus* wild-type and COM1 ΔpyrF strains, respectively; lane 13, pJFW027 plasmid DNA purified from *E. coli*.

DETAILED DESCRIPTION OF ILLUSTRATIVE EMBODIMENTS

Figure 1:
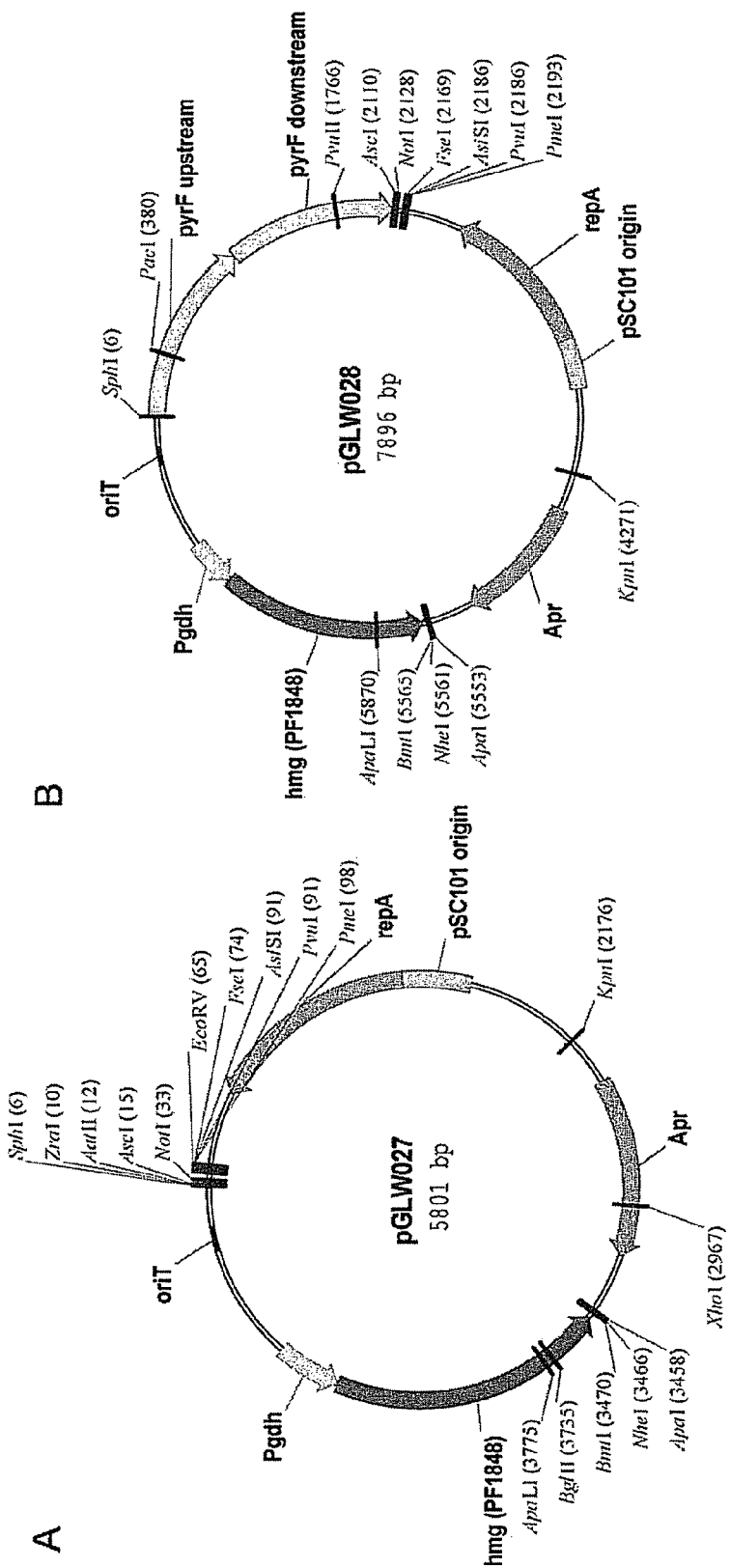
FIG. 1 shows plasmid constructs pGLW027 with $P_{gdh}$hmg cassette (A), pGLW028 for deletion of pyrF (B), pGLW015 with $P_{gdh}$pyrF cassette (C), pGLW021 for deletion of the SHI operon (D), pKSW001 for deletion of the SHII operon (E). Plasmid diagrams were constructed using Vector NTI software (Invitrogen). All plasmids contain the apramycin resistance gene (Apr) and the pSC101 replication origin.
Figure 1:
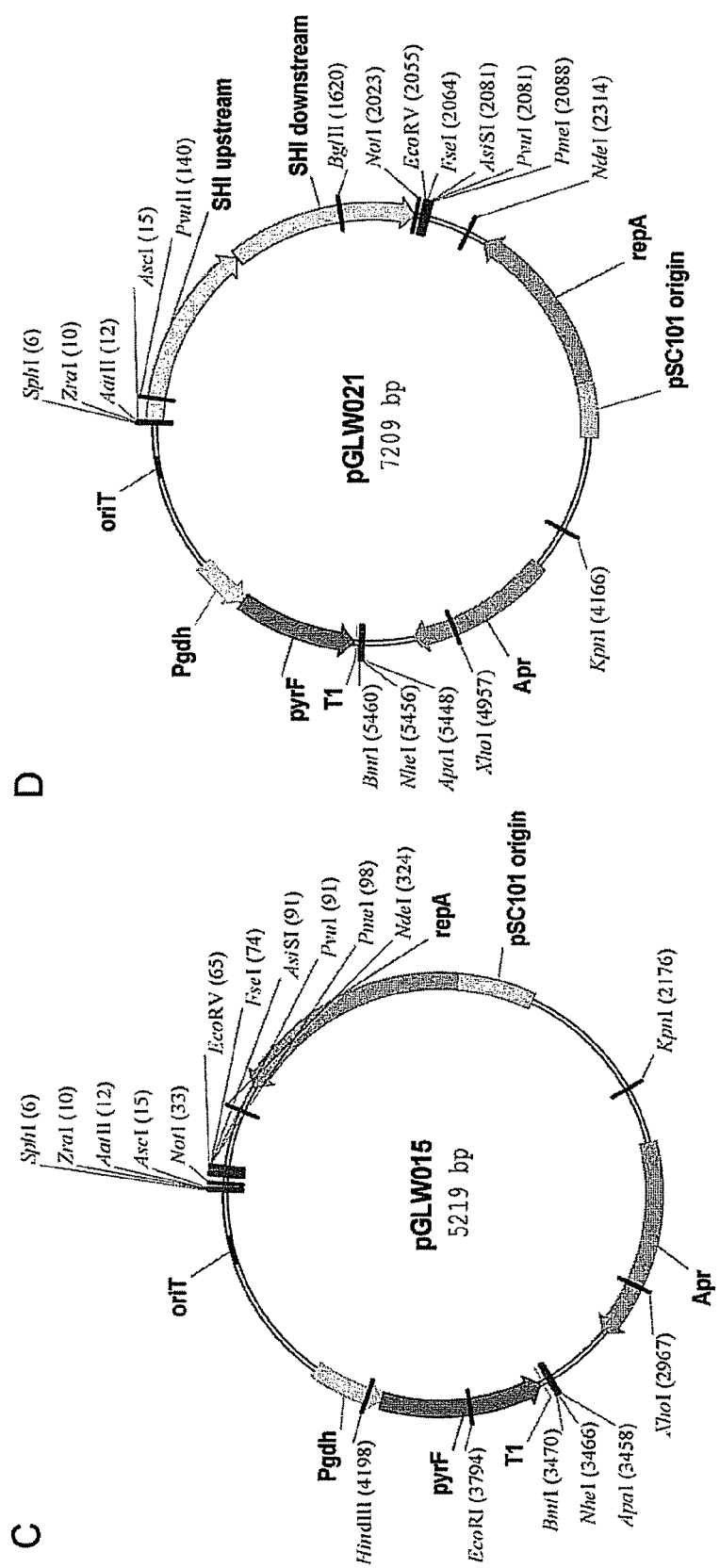
Figure 1:
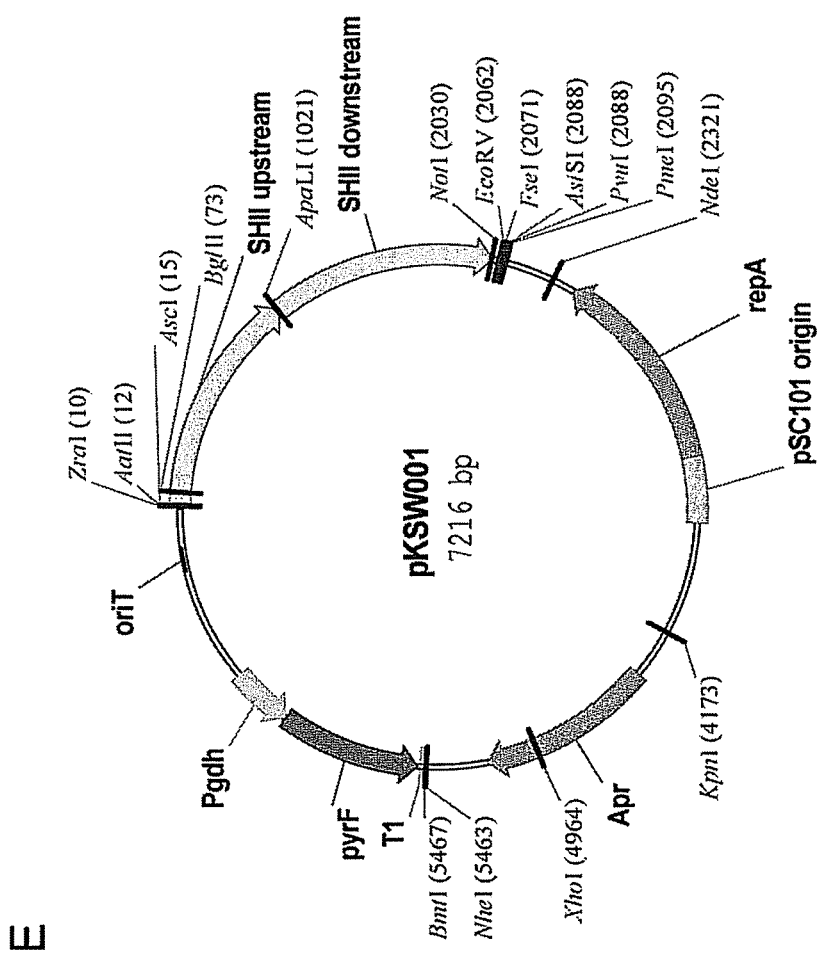

Provided herein are *Pyrococcus furiosus* strains that are highly competent for the uptake and/or integration of extracellular polynucleotides with no sequence specificity. Wild type strains of *P. furiosus* have transformation frequencies that range from undetectable (see Example 1) to $5 \times 10^2$ transformants per microgram DNA (see Waege et al., 2010, Appl. Environ. Microbiol., 76:3308-3133). The highly competent *P. furiosus* strains disclosed herein have transformation frequencies of at least $10^4$ transformants per microgram of DNA. In fact, in one embodiment, highly competent *P. furiosus* can be transformed directly on selective plates by spotting the lawn with DNA containing an appropriate marker. An example of a highly competent *Pyrococcus furiosus* strain is COM1. COM1 was deposited with American Type Culture Collection (ATCC), American Type Culture Collection (ATCC), 10801 University Boulevard, Manassas, Va., 20110-2209, USA, on Sep. 14, 2010. This deposit, designated PTA-11303, will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The high rate of transformation displayed by strains disclosed herein do not require the types of laboratory manipulation often required to observe transformation of a bacterial or archaeal strain. Transformation of a *P. furiosus* strain disclosed herein does not require exposure to conditions that modify the cell membrane. Such conditions include, for instance, an electrical field (e.g., electroporation), removal of the cell wall (e.g., spheroplast formation), modification of the cell membrane charge (e.g., $CaCl_2$), and heat shock. Transformation of a *P. furiosus* strain disclosed herein does not require exposure to an agent that transports a polynucleotide across the cell membrane. Such agents include, for instance, liposomes, phage, and DNA condensing reagents.

In some embodiments a highly competent *P. furiosus* strain disclosed herein includes one or more mutations to help with identification and/or selection of transformants. An example of one type of such a mutation results in a nutritional marker. A nutritional marker is typically a coding region that, when mutated in a cell, confers on that cell a requirement for a particular compound. Cells containing such a mutation will not grow on medium that does not include the appropriate compound, and cells receiving a coding region that complements the mutation can grow on certain types of medium in the absence of the compound. Examples of nutritional markers include, but are not limited to, coding regions encoding polypeptides in biosynthetic pathways, such as nucleic acid biosynthesis (e.g., biosynthesis of uracil), amino acid biosynthesis (e.g., biosynthesis of histidine, leucine, or tryptophan), vitamin biosynthesis (e.g., biosynthesis of thiamine), carbohydrate metabolism (e.g., metabolism of cellobiose), polyamine biosynthesis, and the like.

In one embodiment a nutritional marker can be a mutation in a coding region encoding an enzyme required for uracil biosynthesis, such as a pyrF coding region. An example of a pyrF coding region from *P. furiosus* is depicted at Genbank Accession No. NC_003413 (nucleotides 1062504-1063139 of Genbank Accession No. NC_003413, locus PF1114). Thus, in one embodiment a highly competent *P. furiosus* strain disclosed herein includes a nutritional marker making it a uracil auxotroph, and an example of such a marker results from a mutation in a pyrF coding region.

In another embodiment a nutritional marker can be a mutation in a coding region encoding an enzyme required for histidine biosynthesis, such as a his4 coding region. An example of a his4 coding region from *P. furiosus* is depicted at Genbank Accession No. NC_003413 (nucleotides 1544485-1545612 of Genbank Accession No. NC_003413, locus PF1659). Thus, in one embodiment a highly competent *P. furiosus* strain disclosed herein includes a nutritional marker making it a histidine auxotroph, and an example of such a marker results from a mutation in a his4 coding region.

In another embodiment a nutritional marker can be a mutation in a coding region encoding an enzyme required for agmatine, a precursor for polyamine synthesis, such as apdaD coding region. An example of a pdaD coding region from *P. furiosus* is depicted at Genbank Accession No. NC_003413 (nucleotides 1514933-1515409 of Genbank Accession No. NC_003413, locus PF1623). Thus, in one embodiment a highly competent *P. furiosus* strain disclosed herein includes a nutritional marker making it an agmatine auxotroph, and an example of such a marker results from a mutation in apdaD coding region.

A nutritional marker may have a selectable phenotype. For instance, the inability of a cell to synthesize uracil results in the requirement of uracil (uracil auxotrophy) and resistance to 5-fluoroorotic acid (5-FOA). Many selectable phenotypes for different mutations are known and characterized in *E. coli* and *S. typhimurium* (Vinopal, 1987, In: *Escherichia coli* and *Salmonella typhimurium*: cellular and molecular biology, Neidhardt et al., eds., ASM Press, Washington, D.C., 990-1015). It is expected that such mutations will function similarly in *P. furiosus*.

Also disclosed herein are methods for transforming *P. furiosus*. In one embodiment a method includes contacting a highly competent *P. furiosus* with a polynucleotide, such as DNA, under conditions suitable for uptake of the polynucleotide by the cell, and identifying at least one transformant, wherein the frequency of transformation is at least $10^3$ transformants per microgram DNA per $10^8$ *P. furiosus* cells. The recipient cells may be in liquid medium or solid medium, and the medium may be complex or defined. Complex and defined media useful in the culture of *P. furiosus* are known to the person skilled in the art. The medium may include those components known to the person skilled in the art as helpful in culturing *P. furiosus*, such as, but not limited to, salts, trace minerals, sodium tungstate, resazurin, cysteine, sodium sulfide, and/or sodium bicarbonate (Adams et al., 2001 J. Bacteriol. 183:716-724). In one example of a complex medium additional combinations of, for instance, yeast extract, cellobiose, maltose, and/or casein hydrolysate (enzymatic) may be used. In one example of a defined medium additional combinations of, for instance, vitamins, amino acids, and/or cellobiose may be used. The medium may be buffered at a pH of between 5.8 and 7.5, such as pH 6.8. An example of a suitable buffer is sodium phosphate buffer.

The contacting may occur at any temperature suitable for maintaining the integrity of the polynucleotide to be introduced and suitable for maintaining the recipient cell. Temperatures may range from, for instance, at least 20° C., at least 30° C., at least 40° C., at least 50° C., at least 60° C., at least 70° C., at least 80° C., at least 90° C., to 100° C. In one embodiment, the contacting occurs at a temperature of 98° C.

The cells contacted with the polynucleotide may then be plated onto solid medium or transferred to liquid medium and incubated. The incubation conditions may be aerobic or anaerobic. The medium may include a selection agent to select for cells containing the transforming polynucleotide; however, if the selection agent is bacteriocidal it should not be added until the coding region encoding the marker is allowed to be expressed. The incubation may be for at least 20 hours, at least 40 hours, or at least 60 hours. Individual colonies appearing on the plates are putative transformants, and can be checked for the presence of the transforming polynucleotide. Individual colonies may be replated on selective medium by streaking on fresh plates. The presence of the transforming polynucleotide in the recipient cell, either as a replicating plasmid or integrated into the genomic DNA, can be tested using methods that are known to the skilled person and used routinely, including, for instance, southern hybridization, polymerase chain reaction-based methods, restriction analysis, and the like.

The polynucleotide that is to be introduced into a highly competent *P. furiosus* may be circular (e.g., a plasmid) or linear. The use of plasmids and linear polynucleotides in the transformation of microbes for genetic analysis and genetic engineering is known to the skilled person. In the contacting the amount of polynucleotide used, the number of cells used, and the volume used may vary considerably. In one embodiment, between 2 nanograms and 10 nanograms of DNA per microliter of culture are used, where the culture is at 1 to $2\times10^8$ cells/ml. In one embodiment, 200 nanograms of DNA are added to $1\times106$ cell in a volume of 100 microliters.

In one embodiment, for instance, when a polynucleotide is to be integrated into the genome of a recipient *P. furiosus*, the introduced polynucleotide may include one or more homology regions. A homology region may be long enough to permit homologous recombination between the homology region and a nucleotide sequence present in the genome of the recipient. In general, the longer the homology region, the more likely homologous recombination will occur between the introduced polynucleotide and the recipient's genomic DNA. A homology region may be at least 20 bases (see Example 2), at least 50 bases, at least 100 bases, at least 500 bases, at least 1000 bases, at least 1500 bases, at least 2000 bases, at least 2500 bases, etc. In one embodiment, a polynucleotide includes two homology regions, and the two regions may lack the ability to recombine with each other. The identification of nucleotide sequences for use as a homology region is easily accomplished by the skilled person. For instance, if the genomic DNA sequence of a recipient has been determined, the genomic sequence can be used. Alternatively, polynucleotides can be obtained from a recipient by cloning and used.

In one embodiment, when integration of an introduced polynucleotide is desired by a single crossover event, the introduced polynucleotide may include one homology region. In one embodiment, when integration of an introduced polynucleotide is desired by two crossover events, the introduced polynucleotide may include two homology regions. In one embodiment, a linear polynucleotide for use in transforming a highly competent *P. furiosus* may have two homology regions. In one embodiment, a plasmid for use in transforming a highly competent *P. furiosus* may have one or two homology regions, depending on whether the entire plasmid is to remain in the recipient's genome where it can replicate or a portion of the plasmid is to be removed after integration.

A polynucleotide that is to be introduced may include an intervening region that is to be integrated into the recipient's genome. The use of two homology regions flanking an intervening region can result in replacement of endogenous nucleotides by two crossover events. Any polynucleotide sequence may be present in an intervening region, and an example includes one or more coding regions that encode an exogenous or an endogenous polypeptide. Such a polypeptide may be a marker. Another example includes a nucleotide sequence that results in an alteration of endogenous nucleotides. For instance, an endogenous coding region may be deleted or mutagenized. Such mutations may result in a polypeptide having a different amino acid sequence than was encoded by the endogenous polynucleotide, or may result in altering a regulatory sequence, such as a promoter, to result in increased or decreased expression of an operably linked endogenous coding region. An example of altering endogenous nucleotides is described in Example 1, in which single- and double-deletion mutants of the two gene clusters that encode the two cytoplasmic hydrogenases were generated, and Example 2, in which a deletion of the trpAB locus was generated.

A polynucleotide that is to be introduced may include a coding region that encodes a marker that functions in the recipient. A marker is a molecule that is easily detected by various methods, and permits the selection, and/or screening for cells containing the marker. In some embodiments a marker also permits counter-selection. A marker may render a cell resistant to a selective agent such as an antibiotic including, but not limited to, neomycin, puromycin, hygromycin, streptomycin, and bleomycin. The ability of a marker to confer resistance to a selective agent may vary, as some selective agents may not function at certain extreme conditions (Noll and Vargas, 1997, Arch. Microbiol., 168:73-80). Nevertheless, some antibiotics, such as hygomycin, are able to function at temperatures used to grow thermophiles and hyperthermophiles. Thermostabilized antibiotic resistance markers may be used (Tamakoshi and Oshima, 2011, In: Extremophiles Handbook, Horikoshi (ed.), Springer, Chapter 4.7, pages 547-566).

Another example of a marker that renders a cell resistant to a selective agent is 3-hydroxy-3-methylglutaryl coenzyme A reductase (HMG-CoA), an enzyme used for archaeal membrane lipid biosynthesis (Matsumi et al., J. Bacteriol., 2007, 189:2683-2691). Certain statins, such as mevinolin and its analog simvastatin, inhibit HMG-CoA reductase activity, and overexpression of HMG-CoA reductase can confer resistance to mevinolin and/or simvastatin.

Other markers that permit the selection and/or screening for cells include those coding regions that complement the nutritional markers described herein. Examples include a coding region from a pyr operon, such as pyrF, a coding region from a trp operon, such as trpA or trp B, a coding region from a his operon, such as his4, and apdaD coding region.

A plasmid that is to be introduced may include an origin of replication that functions in the recipient. An example of such an origin of replication is described in in greater detail herein.

In one embodiment, a plasmid used in the methods described herein may be able to replicate in a recipient *P. furiosus*, and in another embodiment a plasmid used in the methods described herein cannot replicate in a recipient *P. furiosus*. An example of a plasmid that replicates in a *P. furiosus* is one that replicates in *P. furiosus* at a one copy per chromosome equivalents. In one embodiment such a plasmid is also stable in a recipient *P. furiosus* without selection for more than 100 generations. In one embodiment such a plasmid is structurally unchanged after replication in *P. furiosus* for more than 100 generations. Such plasmids include an oriC, which may include at least two regions referred to as origin recognition boxes (ORB), and at least two palindromes. Examples of nucleotide sequence of ORBs include, for instance, cccccagagtttcatttccactggaaccaggtt (SEQ ID NO:139), cccccagagtttcatttccactggagccaggtt (SEQ ID NO:140), and agagagttttatttccactggaa (SEQ ID NO:141) (see Matsunaga et al., 2007, Nucl. Acids Res., 35:3214-3222, and other *Pyrococcus* sp. ORB sequences disclosed therein). Examples of two conserved palindromes that may be present in a replicating plasmid include ATATTTAAATAT (SEQ ID NO:133) and ATTAgaTTAAtcTAAT (SEQ ID NO:136). The base differences in the second palindrome are indicated by lowercase type. In one embodiment, such plasmids do not require a cdc6/orc1 coding region located in cis to the oriC for replication. In one embodiment, such plasmids do not require a DNA unwinding site for replication. An example of an oriC region that is sufficient for allowing a plasmid to stably replicate in a *P. furiosus* in single copy is depicted at Genbank Accession No. NC_003413 (nucleotides 15382-16034 of Genbank Accession No. NC_003413). The nucleotides corresponding to the ORB sequences and the palindromes are typically conserved; however, it is expected that other nucleotides within the oriC region can be changed with limited impact on the function of the oriC region.

Methods for modifying the nucleotide sequence of SEQ ID NO:139, as well as methods for adding SEQ ID NO:139 to a polynucleotide (or portions of SEQ ID NO:139) to result in a plasmid that replicates *P. furiosus* are routine and employ standard techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994).

Optionally, a plasmid that is to be introduced may include an origin that functions in a routinely used laboratory microbe, such as *E. coli*. An origin of replication that functions in *E. coli* permits propagation (amplification) of the plasmid for in vitro or in vitro manipulation before introduction into a highly competent *P. furiosus*. If a plasmid includes an origin for replication in *P. furiosus* and an *E. coli* origin, the plasmid may be referred to as a shuttle plasmid.

Using the methods described herein *P. furiosus* can be genetically manipulated. The methods described herein allow the skilled worker access to the types of genetic manipulations that are routinely practiced with microbes that have genetic systems, such as *E. coli* and *Streptomyces* spp., and facilitates the genetic dissection of the nucleotide sequences that determine the physiology and biochemistry of *P. furiosus*. Any sequence, including coding regions and regulatory regions, can be easily modified in the recipient genome, allowing analysis of pathway manipulation, over-expression of polypeptides in their native environment, targeted mutation of polypeptides to modify activity, substrate specificity, etc., and heterologous expression of enzymes from other sources. The methods described herein also permit the modification of endogenous coding regions to encode polypeptides with additional domains. For instance, a polypeptide may be modified to include an affinity tag, such as, but not limited to, a polyhistidine-tag (His-tag). Addition of a His-tag can be achieved by the in-frame addition of a nucleotide sequence encoding the His-tag directly to either the 5' or 3' end of a coding region that encodes a polypeptide. Incorporation of a His-tag into a polypeptide permits the easy isolation of the polypeptide by use of a nickel or cobalt affinity column. Optionally, the His-tag can then be cleaved. Other suitable affinity tags (e.g., maltose-binding protein) and methods of purification of polypeptides with those tags are known in the art. The methods described herein can also be used to transfer recombinant libraries from a donor to a recipient.

Also provided herein are methods for making a highly competent *P. furiosus* strain, and strains made by the process. In one embodiment, a strain made by this process includes an polynucleotide sequence that has been integrated into the recipient's genomic DNA, such as chromosomal DNA, to result in a strain that is different from a wild type *P. furiosus*. The methods include contacting a *P. furiosus* strain that is not highly competent with a polynucleotide under suitable conditions for uptake of the polynucleotide. Such conditions are described herein. The polynucleotide may be circular or linear. In one embodiment, the polynucleotide may include a marker to permit selection and/or identification of transformants. In one embodiment, the polynucleotide may include nucleotide sequences (such as an intervening region) that, upon integration into the recipient *P. furiosus* genome, will cause a mutation that results in nutritional marker. In one embodiment, suitable nucleotide sequences are those that will result in apyrF mutation when integrated into a recipient's genomic DNA by homologous recombination. Such a marker is useful in making and identify a highly competent *P. furiosus* strain since the pyrF results resistance to 5-FOA. In one embodiment, cells contacted with a transforming polynucleotide that produce a pyrF mutation are exposed to the selective agent 5-FOA. The 5-FOA may increase the production of highly competent *P. furiosus*.

The present invention is illustrated by the following examples. It is to be understood that the particular examples, materials, amounts, and procedures are to be interpreted broadly in accordance with the scope and spirit of the invention as set forth herein.

EXAMPLES

Example I

Natural Competence in the Hyperthermophilic Archaeon *Pyrococcus furiosus* Facilitates Genetic Manipulation: Construction of Markerless Deletions of Genes Encoding the Two Cytoplasmic Hydrogenases In attempts to develop a method of introducing DNA into *Pyrococcus furiosus*, a variant was discovered within the wild-type population that is naturally and efficiently competent for DNA uptake. A pyrF gene deletion mutant was constructed in the genome, and the combined transformation and recombination frequencies of this strain allowed marker replacement by direct selection using linear DNA. In this example, the use of this strain, designated COM1, is demonstrated for genetic manipulation. Using genetic selections and counterselections based on uracil biosynthesis, single- and double-deletion mutants of the two gene clusters that encode the two cytoplasmic hydrogenases were generated. The COM1 strain will provide the basis for the development of more sophisticated genetic tools allowing the study and metabolic engineering of this important hyperthermophile. This data is also published in Lipscomb et al., 2011 *Appl. Environ. Microbiol.* 77(7):2232-2238.

Materials and Methods

Strains and growth conditions. *E. coli* strain ET12567 (dam dcm mutant) containing the nontransmissible helper plasmid pUZ8002 was used for initial attempts at conjugation. *E. coli* strain DH5α was used for plasmid DNA preparation and as a control for conjugation experiments. General techniques for *E. coli* were performed as described previously (Sambrook and Russell, *Molecular cloning: a laboratory manual*, 3rd ed. Cold Spring Harbor Laboratory Press, Cold Spring Harbor: New York, N.Y.; 2001).

The *P. furiosus* strains used and constructed in this study are listed in Table 1. The medium for *P. furiosus* growth was composed of 1× base salts, 1× trace minerals, 10 µM sodium tungstate, and 0.25 mg/ml resazurin, with added cysteine at 0.5 g/liter, sodium sulfide at 0.5 g/liter, sodium bicarbonate at 1 g/liter, and 1 mM sodium phosphate buffer (pH 6.8), and for complex medium, containing combinations of 0.05% (wt/vol) yeast extract, 0.35% (wt/vol) cellobiose, 0.5% (wt/vol) maltose, and 0.5% (wt/vol) casein hydrolysate (enzymatic), or, for defined medium, containing 1× vitamin solution, 2×19-amino-acid solution, and 0.35% (wt/vol) cellobiose. The complex medium variations used are as follows: yeast extract, cellobiose, and peptides (YECP); yeast extract and peptides with sulfur (YEP-S0); and yeast extract and maltose (YEM). Stock solutions of individual components were prepared as described previously (Adams et al., 2001 *J. Bacteriol.* 183:716-724). The 200× vitamin stock solution contained (per liter) 10 mg each of niacin, pantothenate, lipoic acid, p-aminobenzoic acid, thiamine ($B_1$), riboflavin ($B_2$), pyridoxine ($B_6$), and cobalamin ($B_{12}$) and 4 mg each of biotin and folic acid. The 25×19-amino-acid stock solution contained (per liter) 3.125 g each of arginine and proline; 1.25 g each of aspartic acid, glutamine, and valine; 5.0 g each of glutamic acid and glycine; 2.5 g each of asparagine, histidine, isoleucine, leucine, lysine, and threonine; 1.875 g each of alanine, methionine, phenylalanine, serine, and tryptophan; and 0.3 g tyrosine. An additional 0.5 g/liter cysteine was added to the defined medium since the amino acid stock solution lacked cysteine. When used, elemental sulfur was added to liquid cultures at a concentration of 2 g/liter. Liquid cultures were inoculated with a 1 to 2% inoculum or with a single colony and then incubated at 90° C. in anaerobic culture bottles or Hungate tubes degassed with three cycles of vacuum and argon.

TABLE 1

*P. furiosus strains used and constructed in this study*

| Strain designation/ phenotype | Genotype | Parent strain/ phenotype | Genome region(s) deleted from parent strain[a] |
|---|---|---|---|
| DSM 3638 | Wild type | | |
| COM1 | ΔpyrF | DSM 3638 | PF1114 (nt 1062504-1063123) |
| ΔSHI | ΔpyrF ΔPF0891-PF0894 | COM1 | PF0891 to PF0894 (nt 863754-867807) |
| ΔSHII | ΔpyrF ΔPF1329-PF1332 | COM1 | PF1329 to PF1332 (nt 1250021-1255193) |
| ΔSHIΔSHII | ΔpyrF ΔPF0891-PF0894 ΔPF1329-PF1332 | ΔSHII | PF0891 to PF0894 (nt 863754-867807) |

[a]Locus tags of deleted genes are listed, followed by nucleotides (nt) of the deleted region in parentheses (*P. furiosus* DSM 3638 genome; GenBank accession no. AE009950.1).

A solid medium was prepared by mixing an equal volume of liquid medium at a 2× concentration with 1% (wt/vol) Phytagel (Sigma) previously autoclaved to solubilize, and both solutions were maintained at 95° C. just prior to mixing. The medium was poured into glass petri dishes immediately after mixing. For solid media with added sulfur, 2 mM polysulfide was added immediately after mixing the 2× medium and solidifying agent (from a 1 M stock polysulfide solution made by reacting yellow elemental sulfur and sodium sulfide anaerobically in a 4:1-mol ratio). After inoculation, plates were inverted and placed into modified paint tanks (or "anaerobic jars"), which were degassed with three cycles of vacuum and argon and incubated at 90° C. for 48 to 64 hours.

Vector Construction and DNA Manipulation.

The $P_{gdh}$-hmg cassette (Matsumi et al., 2007 J. Bacteriol. 189:2683-2691) was cloned into a modified pSET vector (pJHW006, with a modified multiple cloning site and different replication origin, obtained from J. Huddleston) to generate pGLW027. A fragment containing 1-kb flanking regions to the portion of pyrF (PF1114) which did not overlap with adjacent genes was constructed by overlap PCR and cloned into pGLW027 to make the pyrF knockout vector, pGLW028 (see FIG. 1 for vector diagrams). The Pgdh-pyrF cassette was constructed by overlap PCR. A 283-bp portion of the intergenic region upstream of gdh (PF1602) was joined with the pyrF gene with the addition of a 12-bp sequence containing the T1 terminator from the histone gene hpyA1 (PF1722) (Spitalny and Thomm, 2008 Mol. Microbiol. 67:958-970). The cassette was cloned into pJHWOO6 to make pGLW015. The SHI and SHII operon knockout vectors pGLW021 and pKSW001 contained adjacent ~1-kb flanking regions of the SHI operon (PF0891 to PF0894) and the SHII operon (PF1329 to PF1332), respectively, constructed by overlap PCR and cloned into pGLW015 (see FIG. 1 for vector diagrams). The PCR product of the wild-type pyrF genome region used to transform the COM1 background strain was amplified from wild-type genomic DNA with primers amplifying from approximately 1 kb up and downstream from pyrF. The primers used in this study are listed in Table 2.

Transformation and 5-FOA Selection.

For the attempted conjugation experiments, two 50-ml cultures of *E. coli* ET12567 harboring the pUZ8002 helper plasmid with and without the transforming plasmid pGLW028 were grown to an optical density of 0.4 to 0.8 (660 nm). Cells were harvested and washed twice in LB medium. Two 50-ml cultures of wild-type *P. furiosus* were grown in YECP complex medium to a density of approximately $2×10^8$ cells/ml (as determined by counting in a Petroff-Hausser counting chamber). The cells were harvested aerobically by centrifugation, washed twice in 1× base salts, and suspended in 3 ml 1× base salts. This suspension was divided and used to suspend each *E. coli* pellet. The mixtures of *P. furiosus* and *E. coli* cells were incubated at 37° C. for 1 hour aerobically with gentle shaking and then spread onto plates of YECP complex medium containing 22 μM simvastatin (Sigma). Plates were incubated aerobically at 37° C. for 1 hour and then transferred to anaerobic jars and incubated for 48 to 64 hours at 90° C. anaerobically. For natural transformation, aliquots of *P. furiosus* culture typically grown to mid-log phase (~$2×10^8$ cells/ml) in defined liquid medium were mixed with DNA at a concentration of 2 to 10 ng DNA per μl of culture, spread in 30-μl aliquots onto defined solid medium lacking uracil (for COM1 transformations) or containing 16 μM simvastatin (for COM1 and wildtype transformation comparison), and plates were placed inverted in anaerobic jars and incubated at 90° C. for ~64 hours. Serial dilutions of culture were made in order to calculate plating efficiencies. The transformation frequencies reported herein take into account the number of cells plated as determined by culture cell counts (this does not take into account the plating efficiency), and, where indicated, the total amount of DNA added (i.e., the number of transformants per microgram of DNA per $10^8$ cells). Colonies were picked into 4 to 6 ml of liquid medium in Hungate tubes—either complex medium (YECP) with simvastatin or defined medium without uracil—and incubated anaerobically overnight at 90° C. For 5-FOA selection, 30 μl of culture was plated directly onto complex medium plates containing 8 mM 5-FOA and 20 μM uracil with 2 mM polysulfide added just prior to plate pouring. Colonies resistant to 5-FOA were cultured similarly in nonselective complex medium for genomic DNA isolation and screening. After PCR confirmation of a deletion, the resulting strains were passaged twice on solid medium for colony purification.

Genomic DNA Isolation.

For genomic DNA isolation, cells from 1 ml of overnight *P. furiosus* culture were harvested and suspended in 100 μl buffer A (25% sucrose, 50 mM Tris-HCl, 40 mM EDTA, pH 7.4) followed by addition of 250 μl 6 M guanidinium HCl—20 mM Tris, pH 8.5, with incubation at 70° C. for 5 min. Genomic DNA was extracted with phenol-chloroform-isoamyl alcohol (25:24:1; buffered at pH 8), ethanol precipitated, and suspended in 50 μl 10 mM Tris buffer, pH 8.0.

Screening, Purification, and Sequence Verification of Mutants.

Transformant colonies were inoculated into liquid medium for genomic DNA extraction and subsequent PCR screening of the target region. Primers were designed to amplify up and downstream from the homologous regions used to construct the deletion (Table 2). For PCRs, the extension time used was sufficient to allow for amplification of the wild-type allele, if it was still present. After initial screening, transformants containing the expected deletion were further purified by two additional passages under selection on solid medium and screened a second time by PCR to check for segregation of the deleted allele. The deletions were then verified in the purified isolates by sequence analysis. A PCR product was generated from genomic DNA by using primers outside the homologous regions used to construct the deletion, and internal primers were used to sequence the PCR product.

TABLE 2

Primers used in the study

| Primer sequence (5'-3')ᵃ | SEQ ID NO: | Purpose |
|---|---|---|
| pyrF knockout vector and deletion confirmation | | |
| *agagagaggcatgc*cacctacctcctatattgttccatg | 1 | primer for pyrF~1-kb upstream flanking region, with SphI site plus 8 extra bases |
| *ttgagctcc*attcagccacctccaatatttcc | 2 | primer for pyrF~1-kb upstream flanking region, with overlap to 5' end of 1-kb downstream flanking region |
| *aggtggctga*atggagctcaagataaagcacc | 3 | primer for pyrF~1-kb downstream flanking region, with overlap 3' end of 1-kb upstream flanking region |
| *agagagagggcgcgcc*gtcaagaggatgattaggtagagc | 4 | primer for pyrF~1-kb downstream flanking region, with AscI site plus 8 extra bases |
| ctcaactgtgatgtttgtcttgc | 5 | confirmation/sequencing primer for pyrF deletion |
| cgttggcaaacaacttcctg | 6 | confirmation/sequencing primer for pyrF deletion |
| gaaataactccaagaccacttcc | 7 | confirmation primer for plasmid insertion at pyrF genome region |
| gaaagctggagcagattacatc | 8 | confirmation primer for plasmid insertion at pyrF genome region |
| Vector primers | | |
| ccaaggaaagtctacacgaacc | 9 | primer upstream from MCS on pJHW008 derivative vectors |
| ctgagacaacttgttacagcttc | 10 | primer downstream from MCS on pJHW008 derivative vectors |
| hmg genome region | | |
| cattccatctccaatgaactttgc | 11 | confirmation/sequencing primer for plasmid insertion at hmg |
| tgctcaacaaggttagagaagc | 12 | confirmation/sequencing primer for plasmid insertion at hmg |
| gaacaaatggaacgtcttcacc | 13 | confirmation/sequencing primer for plasmid insertion at hmg |
| gacgtgttggaggatctcaag | 14 | confirmation/sequencing primer for plasmid insertion at hmg |
| P$_{gdh}$pyrF cassette | | |
| gattgaaaatggagtgagctgag | 15 | primes from 5' end of gdh promoter region |
| gttcatccctccaaattaggtg | 16 | primes from 3' end of the gdh promoter region |
| *aatcacctaatttggagggatgaac*atgattgtactagcgttggacg | 17 | primes from 5' end of pyrF, with overlap to 3' end of the gdh promoter |
| *ctaaaaagatttt*atcttgagctccattctttcacc | 18 | primes from 3' end of pyrF, with putative termination sequence T1 from hpyA1 |
| SHI operon knockout vector and deletion confirmation | | |
| *agagagagggcgcgcc*tgagtatgaagctagggagaac | 19 | primer for SHI operon upstream ~1-kb flanking region, with AscI site plus 8 extra bp |

TABLE 2-continued

Primers used in the study

| Primer sequence (5'-3')ᵃ | SEQ ID NO: | Purpose |
|---|---|---|
| *caacaaaaatagataaaaaggatta*aaacaaaccacctcccaatgag | 20 | primer for SHI operon upstream ~1-kb flanking region, with overlap to 5' end of SHI downstream 1-kb flanking region |
| ttaatccttttatctattttgttgag | 21 | primer for SHI operon downstream ~1-kb flanking region |
| *agagagaggcggccgc*taggatttcttgtagctctagtac | 22 | primer for SHI operon downstream ~1-kb flanking region, with NotI site plus 8 extra bases |
| cagtgaatggctttggaacc | 23 | confirmation/sequencing primer for SHI operon deletion |
| gaaagggagtatttagggacac | 24 | confirmation/sequencing primer for SHI operon deletion |
| agaagagggacttcaaggcg | 25 | sequencing primer for SHI operon deletion |
| SHII operon knockout vector and deletion confirmation | | |
| *taaggcgcgcc*atttagaccatcctcctttt | 26 | primer for SHII operon upstream ~1-kb flanking region, with AscI site plus 8 extra bp |
| *acgaagtgcac*aacttttctcacctcctttt | 27 | primer for SHII operon upstream ~1-kb flanking region, with overlap to 5' end of SHI downstream ~1-kb flanking region |
| *agaaaagttgt*gcacttcgtcaagctttaa | 28 | primer for SHII operon downstream ~1-kb flanking region with overlap to 3' end of SHI upstream ~1-kb flanking region |
| *tccttagagcggccgc*ggtagatgctttaa | 29 | primer for SHII operon downstream 1-kb flanking region, with NotI site and 8 extra bases |
| cattatgcacatcaccctacaaga | 30 | sequencing primer for SHII operon deletion |
| agaaatccaagggaagtccttgaa | 31 | sequencing primer for SHII operon deletion |
| ctccctcacagccttactaggatt | 32 | confirmation/sequencing primer for SHII operon deletion |
| aagcagttacggcaatccacgata | 33 | confirmation/sequencing primer for SHII operon deletion |
| RT-qPCR | | |
| cgttgttgttgtgctagatcc | 34 | forward primer for qPCR of PF0971 (por) |
| gatggcttcctctatgctctc | 35 | reverse primer for qPCR of PF0971 (por) |
| tcaaaaccagaatacagggagg | 36 | forward primer for qPCR of PF0891 (shlβ) |
| ccttctctctcctcaccttg | 37 | reverse primer for qPCR of PF0891 (shlβ) |
| cagtttgtccagctgacgat | 38 | forward primer for qPCR of PF0892 (shlγ) |
| caggctttagtctatggacaac | 39 | reverse primer for qPCR of PF0892 (shlγ) |
| ggaagcgtttcaactgagga | 40 | forward primer for qPCR of PF0893 (shlδ) |
| cttccagagctcttctaatggc | 41 | reverse primer for qPCR of PF0893 (shlδ) |
| tgagcagtacagcgaagttg | 42 | forward primer for qPCR of PF0894 (shlα) |
| ccgtataggaggtcagcattg | 43 | reverse primer for qPCR of PF0894 (shlα) |
| cataaggccaagggatgctatg | 44 | forward primer for qPCR of PF1329 (shlIβ) |
| ctccttctttcgtagtatgggtc | 45 | reverse primer for qPCR of PF1329 (shlIβ) |

TABLE 2-continued

Primers used in the study

| Primer sequence (5'-3')[a] | SEQ ID NO: | Purpose |
|---|---|---|
| ccaatacagctttgcatcagaag | 46 | forward primer for qPCR of PF1330 (shIIγ) |
| taacggagccattccaagtc | 47 | reverse primer for qPCR of PF1330 (shIIγ) |
| ctggaactgtatcgacacagag | 48 | forward primer for qPCR of PF1331 (shIIδ) |
| ctcttctgtaagcctctttcgag | 49 | reverse primer for qPCR of PF1331 (shIIδ) |
| acggtgaggttaaggatgctag | 50 | forward primer for qPCR of PF1332 (shIIα) |
| caaggaggtagaggtggagtg | 51 | reverse primer for qPCR of PF1332 (shIIα) |
| gaaatactcgagcttggagagg | 52 | forward primer for qPCR of PF1113 |
| caacggtaacctcaataggttcc | 53 | reverse primer for qPCR of PF1113 |
| gatctaaagctggcagacatc | 54 | forward primer for qPCR of PF1114 (pyrF) |
| ccaggatggctcatctcaac | 55 | reverse primer for qPCR of PF1114 (pyrF) |
| gttgcggagttcgataagacc | 56 | forward primer for qPCR of PF1115 |
| cctcatccacaactactctcttg | 57 | reverse primer for qPCR of PF1115 |
| ttgaagatggctaaggagttgg | 58 | forward primer for qPCR of PF1116 |
| cggttctccaatcacaacatc | 59 | reverse primer for qPCR of PF1116 |

[a]Primer tails are indicated in italics

RNA Extraction and RT-qPCR Analyses.

Total RNA was extracted from cell extracts of *P. furious* with acid-phenol (Schut et al., 2001 J. Bacteriol. 183:7027-7036) and stored at −80° C. until needed. RNA was treated with Turbo DNase (Ambion) for 30 min at 37° C. and further purified using the Absolutely RNA clean up kit (Agilent Technologies). cDNA was then prepared using the Affinity-Script quantitative PCR (qPCR) cDNA synthesis kit (Agilent Technologies). All quantitative reverse transcription-PCR (RT-qPCR) experiments were carried out with an Mx3000P instrument (Stratagene) with the Brilliant SYBR green qPCR master mix (Agilent Technologies). The gene encoding the pyruvate ferredoxin oxidoreductase gamma subunit (PF0971) was used as an internal control for RNA quality. Table 2 lists the primers used in RT-qPCR experiments.

Results

Construction and Characterization of a *P. furiosus* ΔpyrF Strain.

Figure 2:
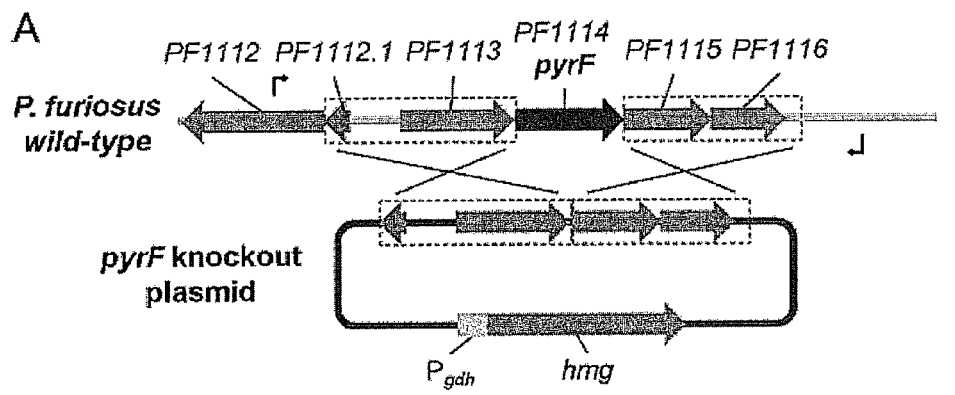
FIG. 2 shows a strategy for obtaining a pyrF deletion and PCR analysis of the pyrF deletion in the COM1 strain.
Figure 2:
Figure 2:
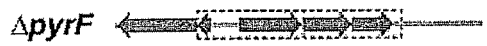
Figure 2:
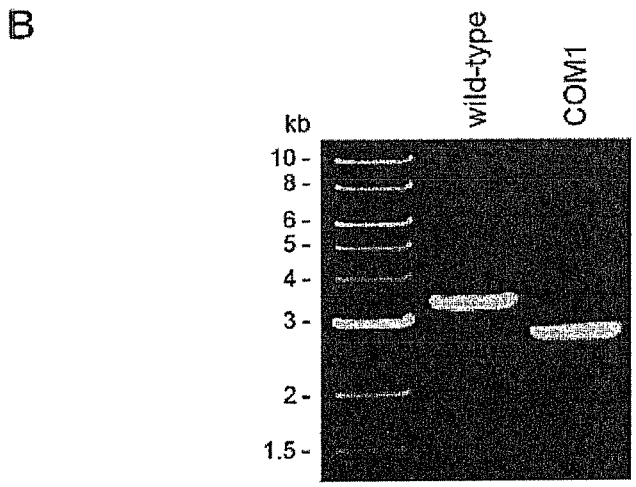

To generate a deletion of pyrF (PF1114) in the *P. furiosus* chromosome, a deletion of the gene was constructed on a plasmid containing the *P. furiosus* HMG-CoA reductase gene (hmg; PF1848) under the control of the *P. furiosus* glutamate dehydrogenase (gdh; PF1602) promoter for selection with simvastatin. We found that the sensitivity of *P. furiosus* to simvastatin on solid medium varies depending on medium type (defined versus complex), density of plated cells, and length of incubation time, with the MIC ranging from approximately 10 μM to over 24 μM. We had limited success in obtaining a clean background for selection with simvastatin, presumably due to a high rate of spontaneous resistance to simvastatin from mutations causing native gene amplification, as noted elsewhere (Allers and Mevarech, 2005 Nat. Rev. Genet. 6:58-73; Santangelo et al., 2010 Appl. Environ. Microbiol. 76:1044-1052). The strategy for construction of a pyrF deletion strain is depicted in FIG. 2A.

We tried a number of methods to introduce plasmid DNA into *P. furiosus*, including the heat shock method used successfully in *T. kodakarensis* (Sato et al., 2005 Appl. Environ. Microbiol. 71:3889-3899; Sato et al., 2003 J. Bacteriol. 185: 210-220), but did not obtain transformants by simvastatin selection. However, an attempt at conjugation of *P. furiosus* (DSM 3638) with *E. coli* yielded two transformants (from $10^9$ *P. furiosus* cells), which were verified by PCR analysis to contain the $P_{gdh}$-hmg cassette. Subsequent experiments showed that *E. coli* was not required for transformation and that *P. furiosus* is naturally competent for DNA uptake. The initial selection of these transformants likely resulted from uptake of DNA released from lysed *E. coli* cells. In other experiments, transformants were also obtained with the non-conjugative DH5α strain of *E. coli*, confirming that DNA was being taken up by *P. furiosus* through a mechanism other than conjugation.

Figure 3:
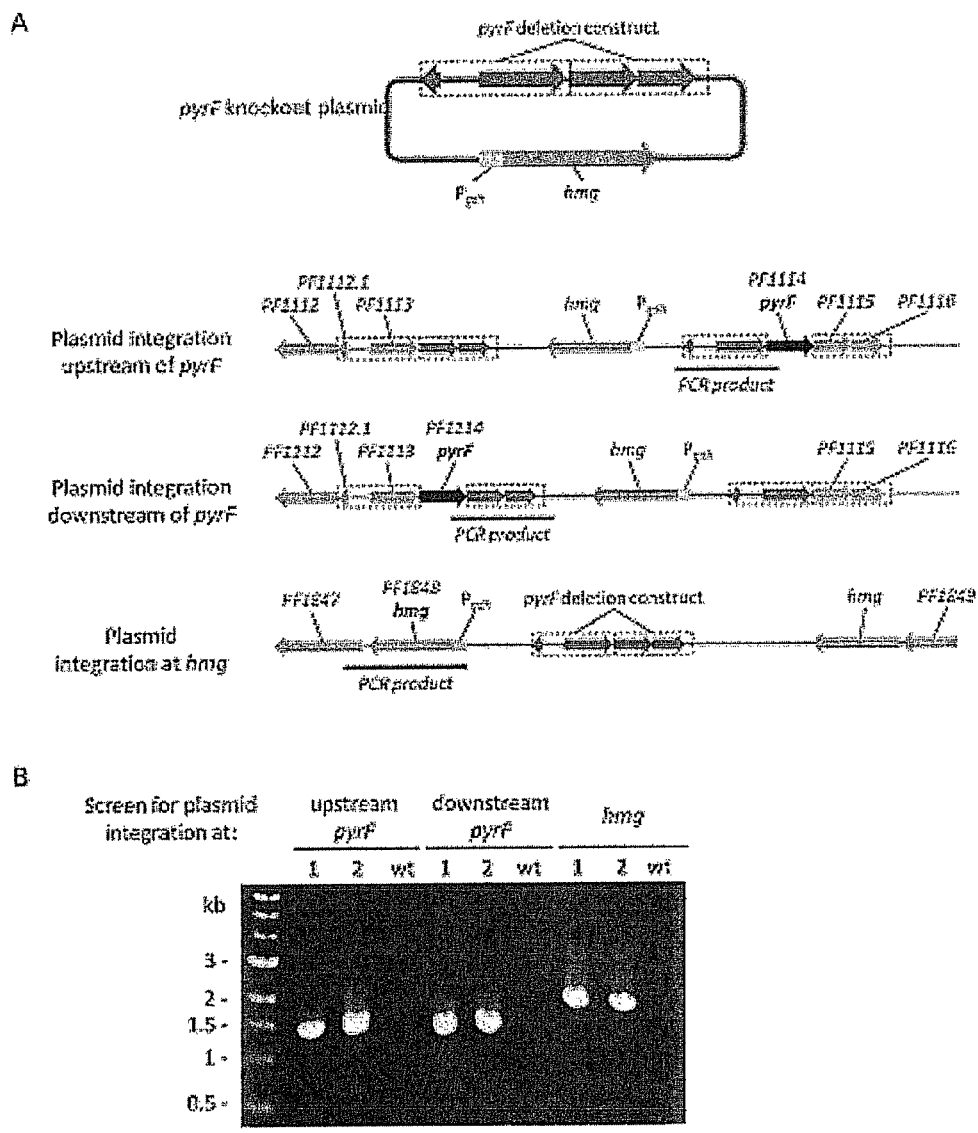
FIG. 3 shows simvastatin resistant isolates 1 and 2 contain plasmid integration at three locations.
Figure 4:
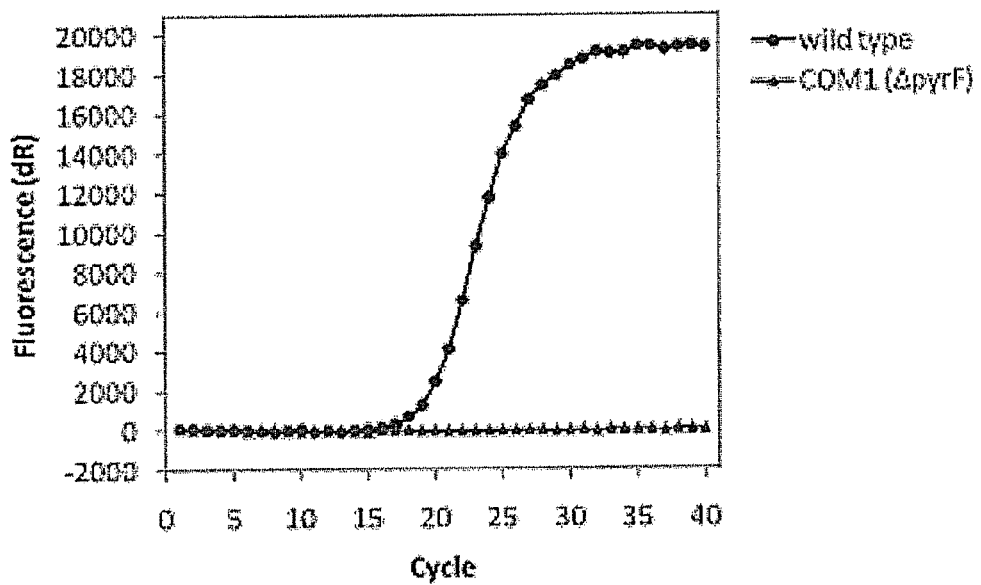
FIG. 4 shows amplification plots from quantitative reverse transcription PCR (RT-qPCR) with primers specific to the pyrF gene, amplified from cDNA generated from RNA extracted from cultures of wild type and COM1.

The two simvastatin-resistant transformants contained plasmids integrated into the *P. furiosus* chromosome at three different locations, as determined by PCR analyses: at both the upstream and downstream flanking regions of the pyrF gene and at the hmg locus, which has 1.2 kb of homology with the plasmid (FIG. 3). The isolates were subcultured once on simvastatin-containing plates for colony purification and then cultured in medium without simvastatin but containing uracil to allow a second crossover event to eliminate the plasmid. The MIC of 5-FOA on YECP complex medium was determined to be 8 mM. Hundreds of colonies were observed on complex medium containing 5-FOA, and of 28 screened by PCR, all contained a deletion of pyrF. Further purification of the isolates by an additional passage on solid medium resulted in loss of the plasmid at the hmg locus. PCR and sequence analysis of the pyrF locus for the isolate designated COM1 verified the deletion and that the plasmid was lost from the hmg locus, generating a wild-type gene. No transcript from the pyrF locus was detected by RT-qPCR (FIG. 4). The COM1 strain was used for all further genetic manipulation.

Figure 5:
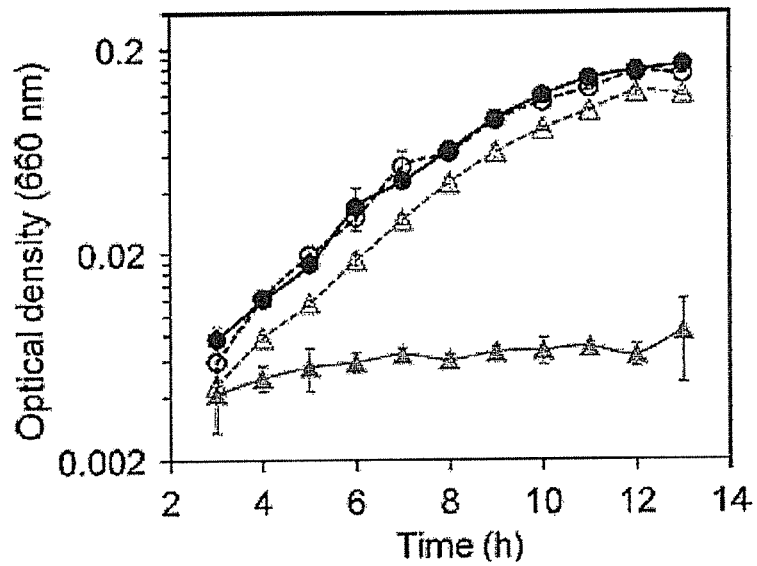
FIG. 5 shows COM1 is a uracil auxotroph. Growth curves of the COM1 strain (triangles) compared to the wild type (circles) in the presence (open symbols) and absence (closed symbols) of uracil. Culture growth was monitored by optical density at 660 nm. The slight increase in optical density for the COM1 strain cultured without uracil reflects a slight darkening of the medium due to incubation at 98° C. The lack of growth in the COM1 strain was verified by assaying protein concentrations for each time point. Each point represents an average of samples from two independent cultures, with error bars showing standard deviation.

A comparison of the growth rates of the *P. furiosus* wild-type and *P. furiosus* COM1 strains in defined medium in the presence and absence of uracil is shown in FIG. 5. The COM1 strain did not grow in the absence of uracil but did grow in medium supplemented with uracil and had a growth rate comparable to that of the wild type. As pyrF is potentially part of a four-gene operon (FIG. 2A), RT-qPCR was used to confirm that expression of the surrounding genes (PF1113, PF1115, and PF1116) was not affected significantly as a result of deletion of pyrF.

The *P. furiosus* COM1 Strain is Naturally Competent for Uptake of Both Circular DNA and Linear DNA.

Figure 6:
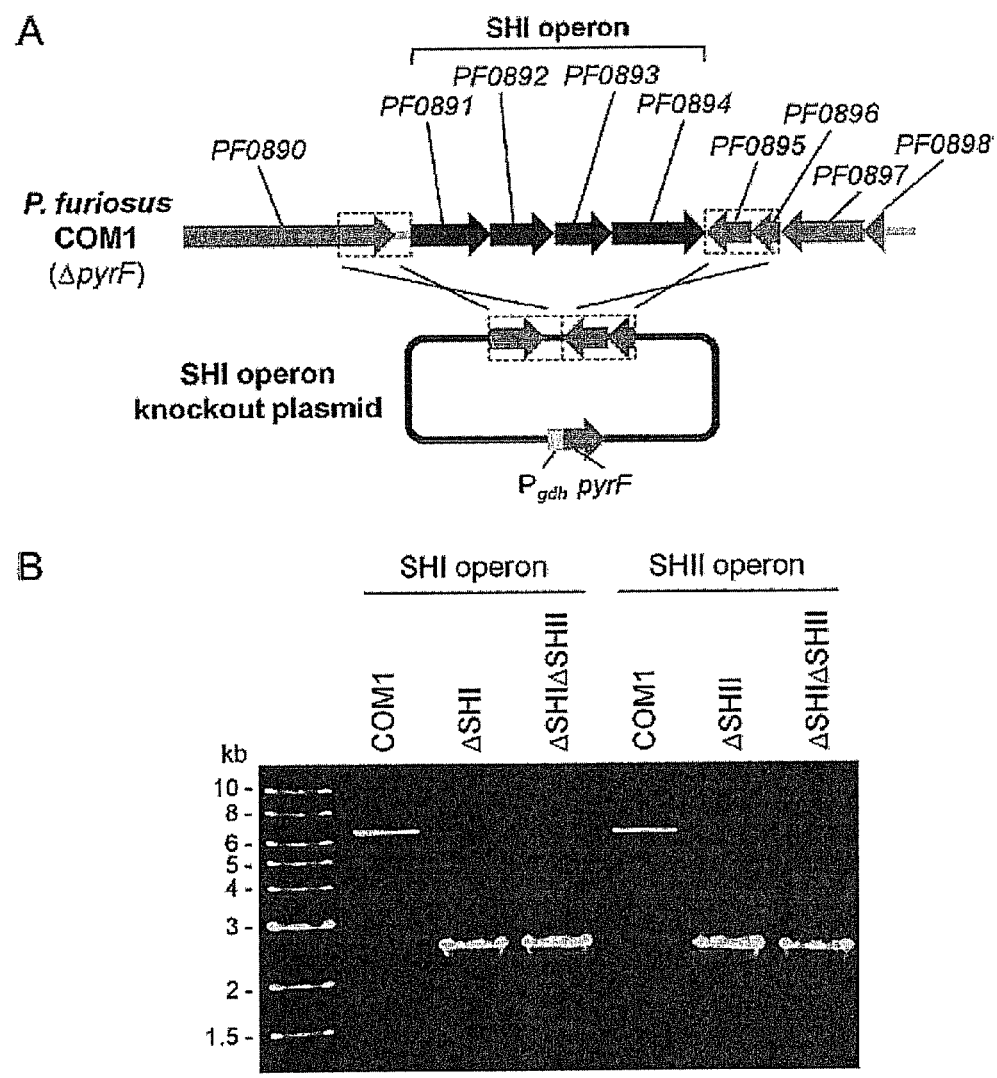
FIG. 6 shows a strategy for obtaining an SHI operon deletion and PCR analyses of the cytoplasmic hydrogenase operon deletions.

The strategy for using the COM1 strain as a background for genetic manipulation rests on the ability to complement the deletion with the wild-type allele, allowing uracil prototrophic selection, as depicted in FIG. 6A. A cassette was constructed for expression of the wild-type pyrF gene under the transcriptional control of the gdh promoter with a short terminator sequence (T1) from the hpyA1 gene (Spitalny and Thomm, 2008 Mol. Microbiol. 67:958-970) at the 3' end of the pyrF gene. Using a plasmid containing this cassette along with 1-kb flanking regions to a genomic target (pGLW021), we obtained on the order of $10^4$ transformants per µg DNA per $10^8$ cells, suggesting that *P. furiosus* is not only naturally competent but that the COM1 strain is highly efficient for DNA uptake. Hundreds of transformants were obtained by simply mixing plasmid DNA containing a wild-type copy of the pyrF gene with a small volume of culture (2 ng DNA per µl culture) under aerobic conditions and plating this mixture onto defined medium without uracil for selection of transformants under anaerobic growth conditions at 90 to 98° C. No colonies were observed in the absence of added DNA, even when plating over 100-fold more cells than were used for transformation. There was also no significant change in the number of observed transformants as a result of varying the carbon source in the defined medium (cellobiose, maltose, or malto-oligosacharides). Early, mid- or late-log-phase cells were capable of undergoing transformation, including aliquots of cells from cultures that had been stored at room temperature (anaerobically) for up to 2 weeks. Since plating was carried out aerobically for convenience, we observed variable plating efficiencies (up to 80%), with the average being approximately 10%.

Figure 7:
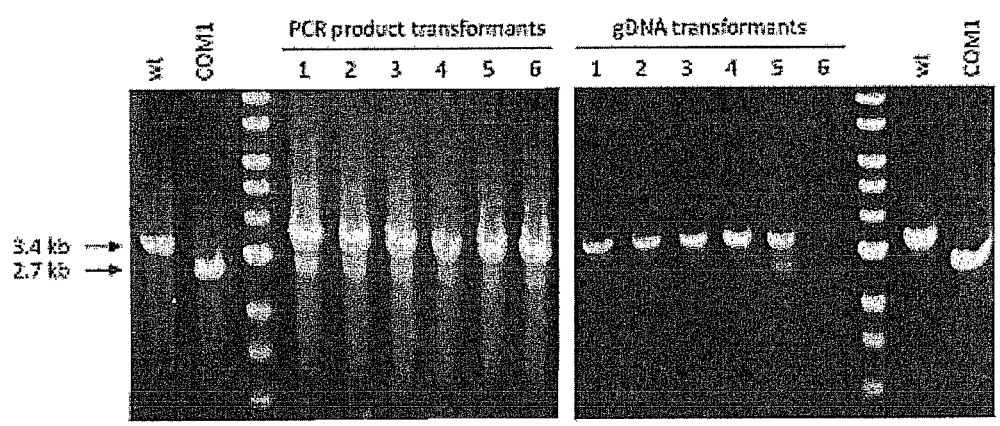
FIG. 7 shows a PCR screen of transformants obtained using either a PCR product of the wild type pyrF region (left panel) or intact genomic DNA (gDNA) containing the wild type pyrF allele (right panel). Genomic DNA from the wild type (wt) and COM1 strains were included as controls. PCR was performed with primers targeting the region of the pyrF locus. All transformants have the pyrF locus restored to wild type (3.4 kb), and some still contain mixtures with the pyrF deletion (2.7 kb).

To test transformation with linear DNA, PCR products containing the wild-type pyrF gene were generated with 1-kb flanking regions to pyrF and used to transform the COM1 strain. Transformants were obtained at frequencies in the range of $10^5$ per $10^8$ cells, and even the addition of intact wild-type genomic DNA repaired the pyrF locus (FIG. 7). The COM1 strain was also transformed by spotting DNA onto a lawn of cells on plates. We noted that transformant colonies that were screened (directly after subculturing the colonies once in liquid medium) often contained a mixture of the wild-type and mutant alleles (FIGS. 7 and 8), and this can be attributed to the existence of multiple chromosomal copies in *P. furiosus* (Matsunaga et al., 2001 Proc. Natl. Acad. Sci. U.S.A. 98:11152-11157). It was therefore necessary to allow genome segregation of deletion mutants with subsequent colony purification. The combination of natural competence and recombination in the COM1 strain results in efficient marker replacement using linear as well as circular DNA.

Given the high frequencies of natural transformation of the COM1 strain, we sought to compare it to the wild type. The pyrF deletion plasmid containing the $P_{gdh}$-hmg cassette was used to transform both the COM1 and wild-type strains, selecting for simvastatin resistance. For experiments in which we observed no transformants for the wild type (in $10^8$ cells), we observed on the order of $10^5$ transformants per $10^8$ cells for the COM1 strain. This dramatic difference in transformation frequencies between the two strains may reflect changes in DNA uptake, homologous recombination, or both; however, the underlying mechanism(s) involved is as yet unknown.

Construction of Markerless Deletion Mutants of the *P. furiosus* Cytoplasmic Hydrogenases.

*P. furiosus* contains two cytoplasmic (soluble) hydrogenases (SHI and SHII) each encoded by four genes predicted to be in an operon, PF0891 to PF0894 (coding for the SHI beta, gamma, delta, and alpha subunits, respectively) and PF1329 to PF1332 (coding for the SHII beta, gamma, delta, and alpha subunits, respectively) (Ma et al., 1993 Proc. Natl. Acad. Sci. U.S.A. 90:5341-5344; Ma et al., 2000 J. Bacteriol. 182:1864-1871). Deletions of each were constructed on plasmids containing the $P_{gdh}$-pyrF cassette. The deletion strategy is depicted in FIG. 6A. Plasmid DNA containing a deletion of one of the operons was transformed into the COM1 strain. After selection for uracil prototrophy, the resulting transformants were screened by PCR to confirm integration of the plasmid at the targeted genome regions. Transformants were cultured in defined medium without uracil and then spread onto YEP-S0 complex medium plates containing 5-FOA and uracil to select double-crossover events removing the integrated plasmid containing the wild-type pyrF gene. Previous microarray analyses showed that expression of both hydrogenases was significantly downregulated in the presence of elemental sulfur (Adams et al., 2001 J. Bacteriol. 183:716-724; Schut et al., 2007 J. Bacteriol. 189:4431-4441), so sulfur in the form of polysulfide was added to the 5-FOA selection plates to reduce any possible detrimental effects of the deletions. We initially passaged the cells in nonselective liquid medium with added uracil prior to selection on plates containing 5-FOA to relieve selective pressure for the pyrF marker, but found that this step was not necessary. Recombination appears to be sufficiently efficient in *P. furiosus* to allow loss of the selected marker on 5-FOA by plating directly from cultures grown in medium lacking uracil.

Figure 8:
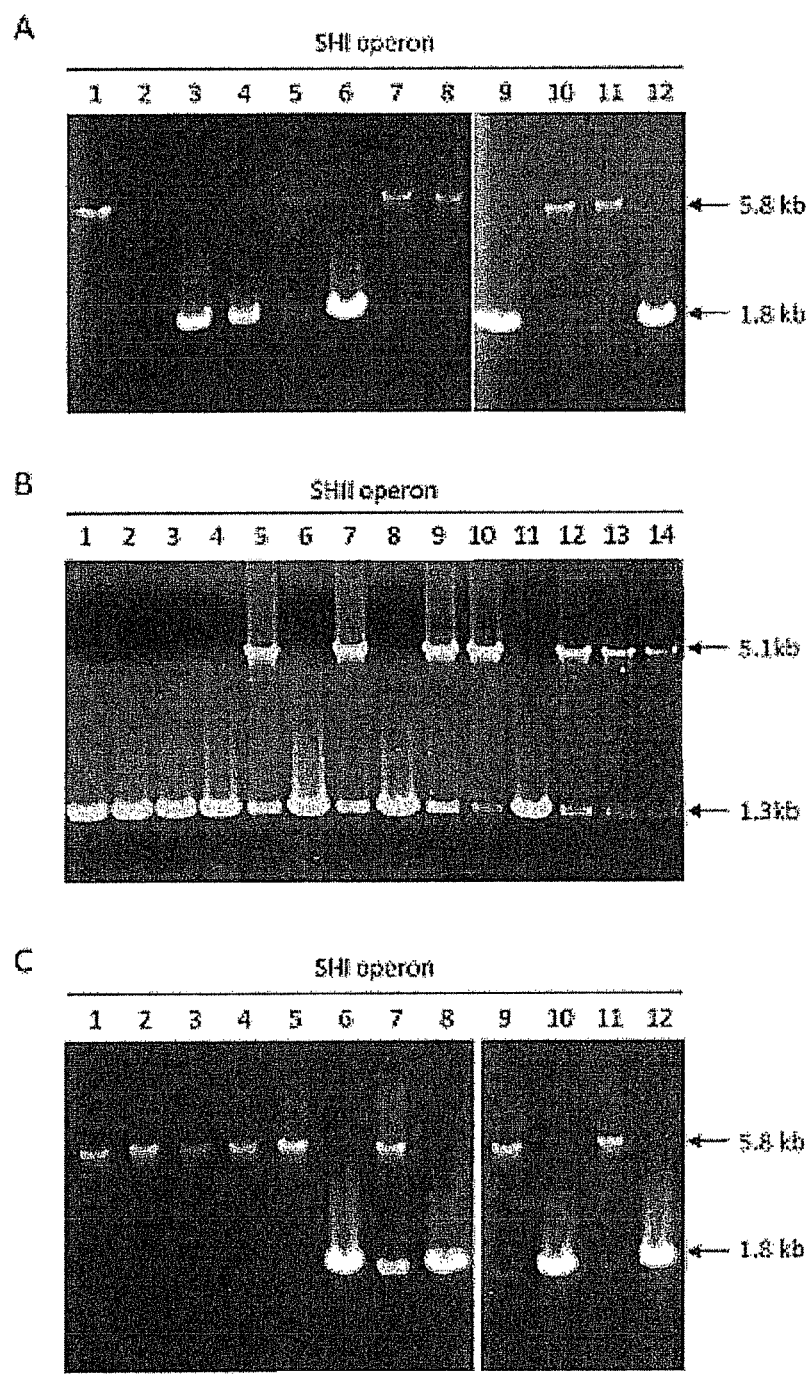
FIG. 8 shows a PCR screen for SHI and SHII operon deletions. PCR products of SHI or SHII operon genome region in isolates screened to find deletions of the SHI operon in the COM1 strain (A), the SHII operon in the COM1 strain (B), the SHI operon in the ΔSHII strain (C). PCR was performed with primer sets in which at least one primer in the set was outside the homologous regions on the transforming plasmid DNA.

PCR amplification of the SHI and SHII operon genome regions was used to screen 5-FOA-resistant isolates. Of 12 isolates screened for deletion of the SHI operon, 5 contained clean deletions and 4 contained products indicating a mixture of the wild type and the deletion mutant (FIG. 8). Of 14 isolates screened for deletion of the SHII operon, seven contained clean deletions and seven were mixtures of the wild type and the deletion mutant (FIG. 8). Selected isolates containing clean deletions were further purified on solid medium, and the deletion was confirmed by PCR analyses (FIG. 6B). The ΔpyrF ΔPF0891-PF0894 and ΔpyrF ΔPF1329-PF1332 strains (designated ΔSHI and ΔSHII, respectively) were verified by sequencing PCR products amplified from outside the homologous regions used to generate the deletions. The absence of the operon transcripts was confirmed by RT-qPCR with primer pairs targeting each gene within the operons.

The hydrogenase mutants were cultured in YEM complex medium in the absence of S0 to examine the growth phenotype. Surprisingly, no differences were observed in the growth of either the ΔSHI or ΔSHII mutant compared to the COM1 parent strain (FIG. 9).

Construction of a ΔSHI ΔSHII Mutant.

An important feature of this strategy for genetic manipulation allows for the iterative selection and counterselection of marker replacements to make multiple deletions in the same strain. To generate a mutant lacking both cytoplasmic hydrogenases, the ΔSHII strain was transformed with the SHI operon deletion plasmid. Transformants were selected for uracil prototrophy and counterselected for loss of the pyrF allele on YEP-S⁰ complex medium containing 5-FOA and uracil. Of 12 isolates screened by PCR, 4 contained a clean deletion of the SHI operon, while 3 contained mixtures of the wild type and the deletion mutant (FIG. 7). The mutants were further purified on solid medium and analyzed by PCR (FIG. 6B). The ΔSHI ΔSHII strain (ΔpyrF ΔPF0891-PF0894 ΔPF1329-PF1332) was verified by sequencing of PCR products generated from the corresponding genome region, and RT-qPCR using primer pairs targeting each gene within each operon confirmed the absence of transcripts from both operons.

Figure 9:
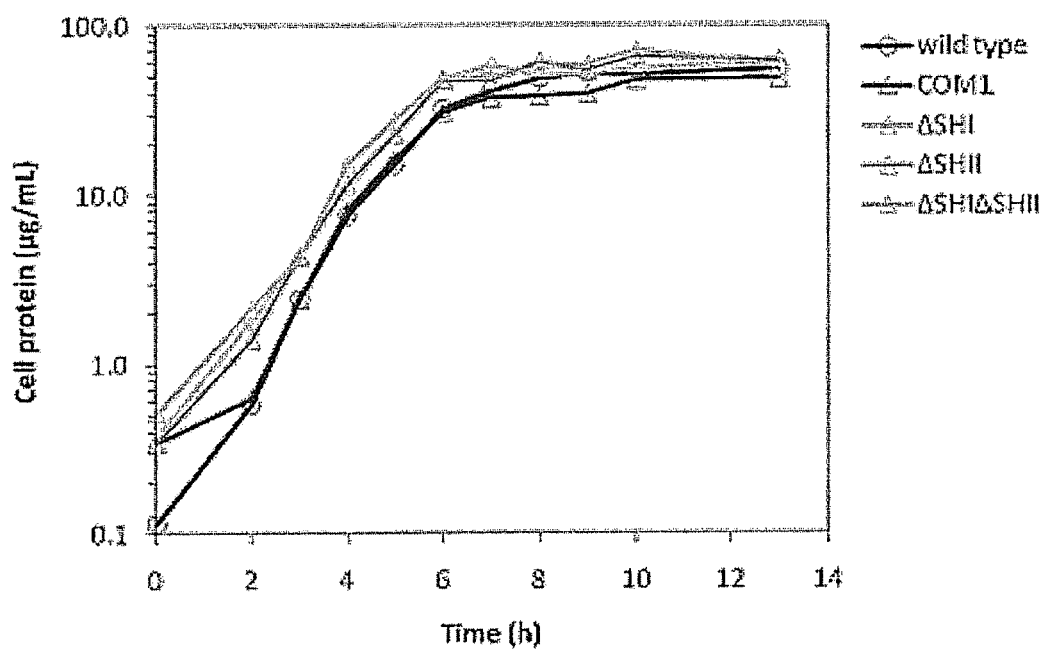
FIG. 9 shows growth of ΔSHI, ΔSHII, and ΔSHIΔSHII mutants compared to COM1 and wild type strains on YEM complex medium. Uracil was added to the medium at a concentration of 20 μM.

The ΔSHI ΔSHII mutant was cultured in YEM medium (without S⁰), and this mutant also displayed no differences in growth compared to COM1 under the conditions tested (FIG. 9).

Discussion

Here we report the construction of a deletion of the pyrF locus in the *P. furiosus* chromosome and the discovery that this strain, designated COM1, is remarkably efficient and naturally competent for uptake of both circular DNA and linear DNA. The combination of DNA uptake and recombination is sufficiently efficient to allow the generation of marker replacement by direct selection using linear DNA. The ability to use PCR products to generate deletions with selection is a major step forward in terms of ease of manipulation and an important genetic tool for the study of *P. furiosus*. The ability to use this methodology to generate single and multiple mutations in the same strain will facilitate the analysis of the physiology and metabolism of this important hyperthermophilic archaeon, as well as allowing its metabolic engineering.

High frequencies of transformation were observed with the *P. furiosus* COM1 strain by adding DNA directly to a small volume of cell culture and spreading this mixture on selective plates. The previously reported method for transformation of *T. kodakarensis* relies on a modified CaCl2 "heat shock" procedure reported for M voltae PS (Bertani and Baresi, 1987 J. Bacteriol. 169:2730-2738), involving an incubation on ice, followed by a short "heat shock" at 85° C., followed by a second incubation on ice. The transformation frequency observed for *P. furiosus* COM1 with uracil prototrophic selection is significantly higher than that reported for *T. kodakarensis* (selection of tryptophan prototrophy in a ΔpyrF ΔtrpF::pyrF mutant). For linear DNA fragments containing ~1 kb of homologous regions, on the order of $10^5$ transformants per μg DNA per $10^8$ cells were obtained, compared with fewer than 100 transformants per μg DNA per $10^8$ cells of *T. kodakarensis* when using linear DNA having the same length of homologous regions (Sato et al., 2005 Appl. Environ. Microbiol. 71:3889-3899). These numbers correspond to transformation frequencies (per μg DNA) of $10^{-3}$ for *P. furiosus* (ΔpyrF) and $10^{-7}$ for *T. kodakarensis* (ΔpyrF ΔtrpF::pyrF). The frequency of natural transformants observed for *P. furiosus* COM1 (up to $10^{-3}$) approaches those reported for the highly naturally competent thermophilic bacterium *Thermus thermophilus* ($10^{-2}$) (Koyama et al., 1986 J. Bacteriol. 166: 338-340) and fall within the range of frequencies observed for other naturally competent bacteria, including *Acinetobacter baylyi* ($7\times10^{-3}$), *Bacillus subtilis* ($3.5\times10^{-2}$), and *Haemophilus influenzae* ($7\times10^{-3}$) (Lorenz and Wackernagel, 1994 Microbiol. Rev. 58:563-602).

While we cannot separate the contribution of DNA uptake from that of homologous recombination since we are not using a replicating shuttle vector, the fact that we often observed more than one plasmid integration event in the same transformant suggests that recombination is efficient. This is also supported by previous work showing that *P. furiosus* has the ability to repair its chromosome after complete fragmentation by gamma irradiation (DiRuggiero et al., 1997 J. Bacteriol. 179:4643-4645). Efficient recombination is also suggested by the fact that loss of the pyrF gene can be selected for directly on plates containing 5-FOA with no intervening growth in nonselective medium. The factors responsible for the increased transformation frequencies with uptake of both circular DNA and linear DNA in the COM1 strain are not clear, but our data suggest that while wild-type *P. furiosus* has a mechanism for natural competence, there are changes in COM1 that markedly increase this ability. There are no obvious homologs of known DNA translocation machinery in the *P. furiosus* genome, such as those found in *B. subtilis*, *Streptococcus pneumoniae*, or *T. thermophilus* (Averhoff, 2009 FEMS Microbiol. Rev. 33:611-626; Clayerys et al., 2009 FEMS Microbiol. Rev. 33:643-656); although apparent homologs to some of the internal DNA processing enzymes often associated with natural competence such as DprA (PF1313), Ssb (PF2020), and RecA (PF1926) appear to be present. The increased natural competence of COM1 is likely due to some mutation(s) present in the original wild-type cell from which the COM1 strain was generated, and the nature of such a change is currently under investigation.

One limitation of the strategy used herein for targeted deletion of the hydrogenase operons is the lack of a direct selection for deletion of the target gene. This is a problem for deletions with severe phenotypes as removal of the integrated plasmid containing the deletion can occur without loss of the target gene. For deletion of genes or operons that might result in a growth defect, a marker replacement strategy can be used wherein the Pgdh-pyrF cassette is placed between target gene flanking regions on a plasmid or linear PCR product. Uracil prototrophic selection can then be used directly for simultaneous transformation and gene deletion.

As an example application of the COM1 strain to make chromosomal manipulations in *P. furiosus*, we deleted the operons encoding either or both cytoplasmic hydrogenases. Surprisingly, no growth phenotype was observed for any of the mutants, and this raises questions about their proposed roles in the primary metabolism in *P. furiosus* (e.g., see Jenney and Adams, 2008 Ann. N.Y. Acad. Sci. 1125:252-266). Studying the pathways of hydrogen production in *P. furiosus* is of great interest because of the increasing concern for production of alternative energy sources, such as hydrogen, to replace fossil fuels. Hyperthermophiles such as *P. furiosus* could potentially have an important role in biological hydrogen production systems (Jenney and Adams, 2008 Ann. N.Y. Acad. Sci. 1125:252-266; Sun et al., 2010 PLoS One 5:e10526), and although the cytoplasmic hydrogenases have been characterized in vitro (Ma et al., 1993 Proc. Natl. Acad. Sci. U.S.A. 90:5341-5344; Ma et al., 2000 J. Bacteriol. 182: 1864-1871), as demonstrated herein, their in vivo functions have yet to be established. The ability to investigate their functions in vivo through genetic manipulation, together with the roles of related enzymes, will provide insight into the mechanisms of hydrogen uptake and production in *P. furiosus* as well as in related hyperthermophiles.

Example II

A Rapid, High Efficiency Method for Selected Marker Replacement in Hyperthermophiles: use for Construction of a Tryptophan Auxotroph for Nutritional Selection in *Pyrococcus furiosus*

We recently reported the isolation of a strain of *Pyrococcus furiosus*, COM1, that is naturally and efficiently competent for DNA uptake. A deletion of the pyrF gene was constructed in the genome, and the combined transformation and recombination frequencies of this strain allowed marker replacement by direct selection using linear DNA. In testing marker replacement by direct selection using linear DNA it was discovered that marker replacement was possible with as few as 20 nucleotides of flanking homology. This feature was used to design a strategy for selection of constructed deletions using PCR products and subsequent excision, or "pop-out", of the selected marker. This method allows the construction of a markerless deletion of virtually any gene that is not essential for viability, no matter how severe the mutant phenotype, and the ease and speed of this method will facilitate the construction of multiply marked strains. In this example, a markerless deletion of the trpAB locus in the COM1 ΔpyrF genetic background was constructed, generating a strain that is a tight tryptophan auxotroph and providing a genetic background with two auxotrophic makers for further strain construction. The utility of the ΔtrpAB strain was demonstrated using protoprophic selection of plasmids containing the wild type trpAB allele. This method will be useful for the development of even more sophisticated genetic tools for the study and metabolic engineering of this important group of organisms.

Results and Discussion

Fewer than 20 Base Pairs of Homologous DNA Allow Selection of Marker Replacements in P. furiosus.

Figure 10:
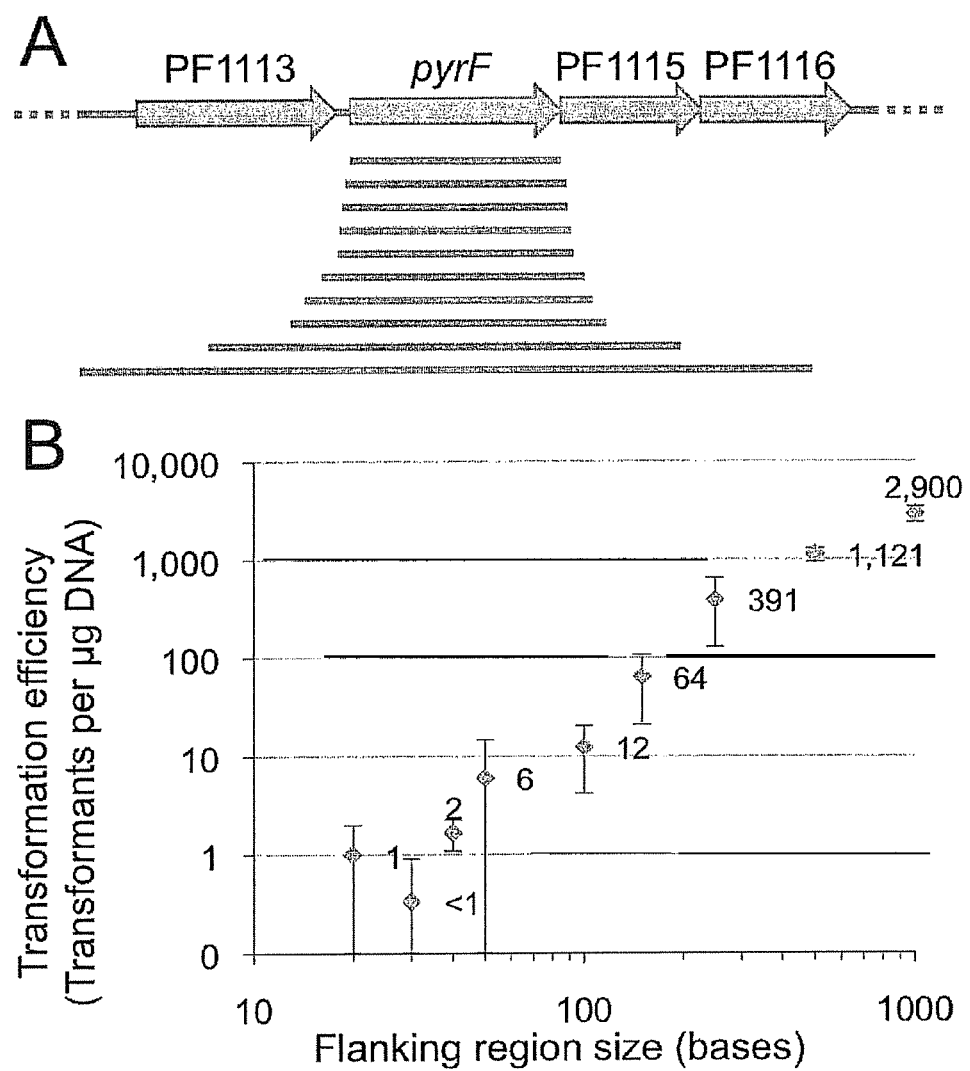
FIG. 10A shows the wild type pyrF region and PCR amplified fragments (indicated as lines below the chromosomal region) with varying lengths of flanking sequence used to transform the COM1 ΔpyrF strain selecting uracil prototrophy.
FIG. 10B shows transformation efficiencies using PCR products. 1 μg of DNA was used to transform ~$10^7$ cells.

The P. furiosus COM1 strain is naturally competent for DNA uptake and the combined frequencies of transformation and recombination in the COM1 ΔpyrF strain allows selection of marker replacements using linear DNA. This selection relies on replacement of the gene of interest with a wild type copy of the pyrF locus (FIG. 10A). To investigate the minimum homology required for recombination, PCR products containing varying lengths of homologous DNA flanking the wild type pyrF gene ranging in length from 0-1000 bp were used to restore the ΔpyrF to wild type (FIG. 10). The PCR fragments were introduced by natural transformation selecting uracil prototrophy and the frequency of transformation was measured as the number of uracil prototrophic transformants per µg of DNA. The two cross-over events required to repair the pyrF deletion were selected simultaneously by directly selecting transformants for uracil prototrophy. The transformation frequency increased exponentially with an increase in flanking region length, from detectable for flanking regions as short as 20 nucleotides to approximately $10^3$ transformants per µg DNA with 1 kb flanking regions (FIG. 10B).

Sequence Homology within the PCR Products Used for Selection of Marker Replacement Allows Pop-Out of the Selected Marker.

Figure 11:
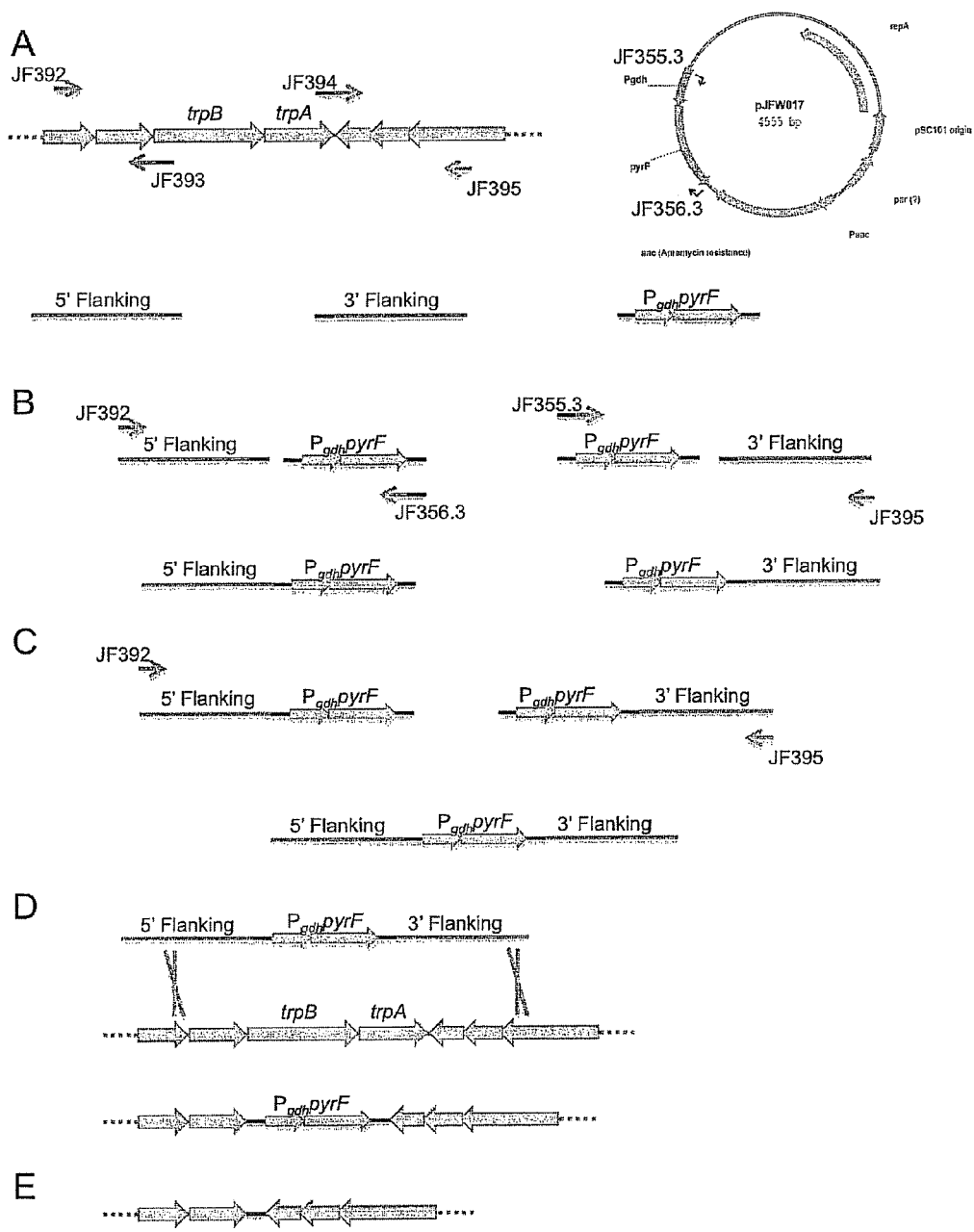
FIG. 11 shows pop-out marker replacement strategy. Six primers are used to construct a pop-out PCR product that is used to direct marker replacement and subsequent excision of the selected marker.

While selection of marker replacements using the wild type copy of pyrF is possible, the resulting strains are uracil prototrophs and are not useful for further mutant construction using pyrF as a selectable marker. To overcome this we designed a strategy based on the pop-out recombination system in T. kodakaraensis (Sato et al., 2005 Appl. Environ. Microbiol. 71:3889-3899) to allow for the subsequent removal of the pyrF gene after selection of the marker replacement. An example of this strategy targeting trypAB is diagramed in FIG. 11. The PCR product containing the deletion cassette is designed to contain the wild type pyrF gene under the control of the GDH promoter ($P_{gdh}$-pyrF) flanked by an additional 40 bp sequence with minimal homology to the P. furiosus chromosome. Generating the pop-out marker replacement cassette involves one PCR amplification and two successive rounds of splicing by overlap extension (SOE) PCR. Because only 40 bp of homologous sequence is needed to pop-out the $P_{gdh}$pyrF marker, primers no longer than 60 bp are needed to construct the deletion cassette using SOE PCR, eliminating the need for PAGE purification of the primers (Table 3). Six primers are then used to amplify three fragments joined by SOE PCR.

TABLE 3

Primer used in this study

| Primer | Sequence (5' to 3') | SEQ ID NO: |
|---|---|---|
| pyrF500bpF | AAAACAGATATCCGAAATACTCGA | 60 |
| pyrF500bpR | GGTTATCTCCCAATCTTATCCCT | 61 |
| pyrF250bpF | ACGAGGCAATAAAGTTCGACGCAA | 62 |
| pyrF250bpR | TAAGATCTTCCTTATCAGAGAGCT | 63 |
| pyrF150bpF | GAGATTGTCAAGAGACTCTATGAT | 64 |
| pyrF150bpR | TCTGTGGTCTTATCGAACTCCGCA | 65 |
| pyrF100bpF | TACTTGGGCAGATAAAATTGGAAG | 66 |
| pyrF100bpR | AGCATCTTGCTTGCAATTTCCTCT | 67 |
| pyrF50bpF | AGTCGTCTTAAAGGGAGACCAACT | 68 |
| pyrF50bpR | ATCTCTTTAACATCCTTCTTGCTT | 69 |
| pyrF40bpF | AGGGAGACCAACTCCCCAGGGAAATATT | 70 |
| pyrF40bpR | TTGATTATCTCTTTAACATCCTTCTTGCTT | 71 |
| pyrF30bpF | ACTCCCCAGGGAAATATTGGAGGT | 72 |
| pyrF30bpR | CTTTAACATCCTTCTTGCTTAGGG | 73 |
| pyrF20bpF | GAAATATGGAGGTGGCTGAATGATTGTAC | 74 |

TABLE 3-continued

Primer used in this study

| Primer | Sequence (5' to 3') | SEQ ID NO: |
|---|---|---|
| pyrF20bpR | CTTCTTGCTTAGGGGGTGCTTTATCTTGAG | 75 |
| pyrF10bpF | AGGTGGCTGAATGATTGTACTAGCGTTGGA | 76 |
| pyrF10bpR | AGG GGG TGCTTTATCTTGAGCTCCATTCTT | 77 |
| pyrF0bpF | ATGATTGTACTAGCGTTGGACGTGTATGAG | 78 |
| pyrF0bpR | TTATCTTGAGCTCCATTCTTTCACCTCCTC | 79 |
| GL055 | AGAGAGAGGCATGCCACCTACCTCCTATATTGTTCCATG | 80 |
| GL058 | GAGAGAGGGCGCGCCGTCAAGAGGATGATTAGGTAGAGC | 81 |
| GL158 | TCAAATGCTCATCATTTAGTTTTATG | 82 |
| JF307 | AATGAGCATGCGTTATAAACACATTCTC | 83 |
| JF311 | AAGCTCTAGAAAAGATATTGGAGGTTCC | 84 |
| JF357 | TTAATATGCCCAGGCCTACTCCTTTGCCGTCATCACCCATATGATCGTGAGTC | 85 |
| JF358 | AGGAGTAGGCCTGGGCATATTAACGTGCTGACTGATAGAGGATTAGCTAAGCTTGAACTC | 86 |
| JF355.1 | AGGAGTAGGCCTGGGCATATTAACGTGCTGACTGATTGAAAATGGAGTGAGCTGAG | 87 |
| JF356.1 | TTAATATGCCCAGGCCTACTCCTTTGCCGTGATTTTATCTTGAGCTCCATTCTTTCAC | 88 |
| JF322 | ACTGCCAGCATGCTCGTAG | 89 |
| JF326 | AGATGCTAGCGAAGGGGATGAAGTTG | 90 |
| JF359 | TTCGTGTTATGATGCCCACTAAGCGTCTGCTCGACCTTCAGATTTCAAAACCCTCATAG | 91 |
| JF360 | TTAGTGGGCATCATAACACGAAAGAGAGTGATTAGAGCCTGTCGTAGACC | 92 |
| JF355.2 | ACGCTTAGTGGGCATCATAACACGAAAGAGAGTGATTGAAAATGGAGTGAGCTGAG | 93 |
| JF356.2 | TGTTATGATGCCCACTAAGCGTCTGCTCGGATTTTATCTTGAGCTCCATTCTTTCACC | 94 |
| JF392 | AAGAGAAGTCGGCAATTCAC | 95 |
| JF393 | ACGAAACCGGGTCTCGGCGTAACACGCTCACTTCACCAAACCACATTTTTGGC | 96 |
| JF394 | TGTTACGCCGAGACCCGGTTTCGTCTCTCATTTAGGGATCTAAAATTTTGTAAAAC | 97 |
| JF395 | TAGGGAGTATAAGAGAAGAGC | 98 |
| JF355.3 | TGTTACGCCGAGACCCGGTTTCGTCTCTCATGATTGAAAATGGAGTGAGCTGAG | 99 |
| JF356.3 | AAACCGGGTCTCGGCGTAACACGCTCACTTGATTTTATCTTGAGCTCCATTCTTTCACC | 100 |
| WN008 | CCAAACCACATTTCAGTTCACCTCCGCCTT | 101 |
| WN009 | GTGAACTGAAATGTGGTTTGGTGAGTTTGG | 102 |
| WN010 | CTAAAAAGATTTTAGATCCCTAAAAGTTCCTCTA | 103 |

Figure 12:
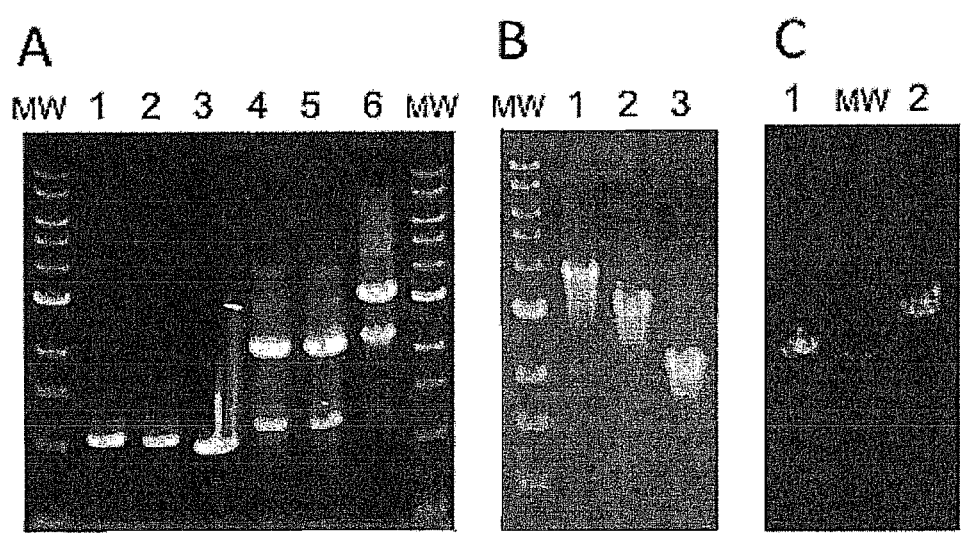
FIG. 12 shows construction of the trpAB pop-out markerless deletion. Panel A. Lanes: 1) 1 kb 5' flanking amplicon, 2) 1 kb 3' flanking amplicon, 3) $P_{gdh}$pyrF marker cassette, 4) overlapped 5' flanking to $P_{gdh}$pyrF marker cassette, 5) overlapped 3' flanking to $P_{gdh}$pyrF marker cassette, 6) trpAB pop-out marker replacement cassette. Panel B. PCR amplification of the genomic regions surrounding the trpAB and radB loci showing the marker replacement, and subsequent pop-out (confirmed by DNA sequencing of the PCR products). Lanes M: 1 Kb DNA ladder, trpAB locus in 1: COM1, 2: JFW01, and 3:JFW02, radB locus in 4: COM1, 5: JFW03, and 6: JFW04. C. PCR amplification of the trpAB region in the mutant and wild type. lane 1 transformant, 2: wild type. A 3.9 kb PCR product is produced from the wild type trpAB locus, while a 3.1 kb band is produced by the targeted marker replacement. MW: 1 kb DNA ladder.

Transformation of the trpAB pop-out construction into the COM1 ΔpyrF strain resulted in hundreds of uracil prototrophic colonies. Eight of these colonies were picked for screening (FIG. 12) and one selected transformant was purified to homogeneity. This intermediate strain, JFW01, is a uracil prototroph, and a tryptophan auxotroph. To allow for the pop-out event at the trpAB locus, JFW01 was grown in media containing uracil, then putative recombinants were selected by 5-FOA resistance. 10 colonies were screened for the pop-out event, of which 4 contained the pop-out as designed in the chromosome. The frequency of the pop-out was $7.4 \times 10^4$.

One of these colonies was designated as JFW02. JFW102 is a tryptophan auxotroph and excision of the $P_{gdh}$-pyrF marker restored 5-FOA resistance and uracil auxotrophy making JFW02 a double auxotroph, suitable for further genetic manipulation.

This strategy has several important advantages over conventional deletion construction. It does not require cloning and only 6 primers are needed to provide specificity for the target gene and the ability to use short primers eliminates the need for PAGE purification. Since both the integration and excision of the $P_{gdh}$-pyrF cassette are selected, this method may be used to target any gene that is not essential for viability no matter how severe the phenotype. While the resulting mutant strains contain a 40 bp 'scar' at the site of the pop-out, the scars are not homologous to each other, so do not provide sites for farther homologous recombination.

A Deletion of the trpAB Locus Results in a Strain that is a Tight Tryptophan Auxotroph but Not Resistant to 5FAA.

Double auxotrophic background strains are often used in molecular genetics to introduce multiple genetic manipulations into a single strain (ref). As with pyrF, tryptophan biosynthesis allows for selection for prototrophy as well as auxotrophy. First demonstrated in *S. cerevisiae*, deleton of the trp1 gene results is a tryptophan auxotroph that is resistant to 5-fluoroanthranilic acid (5-FAA) (Toyn et al., 2000 Yeast 16:553-60). The trp1 homologue in *P. furiosus*, trpF (PF1707), was targeted for pop-out mutagenesis but the resulting strain was a leaky auxotroph not sensitive to 5-FAA.

Deletions of either trpE or trpD has similar phenotypes. Both were leaky tryptophan auxotrophs not sensitive to 5-FAA. We then constructed a deletion of the trpAB locus (shown in FIG. 11) and this deletion resulted in a tight tryptophan auxotroph but not sensitive to 5-FAA.

To test the utility of the trpAB deletion for prototrophic selection the wild type trpAB allele was cloned onto a replicating shuttle vector (Farkas et al., 2011 Appl. Environ. Microbiol. 77:6343-6349 (Example III)) and used to transform the COM1 ΔpyrF ΔtrpAB strain selecting tryptophan prototrophy. JFW02 was readily transformed by pJFW070, selecting either uracil or tryptophan prototrophy. Since both trpAB and pyrF markers are contained on the same plasmid, we were also able to compare transformation efficiency with each selection. Transformation efficiency were $1 \times 10^4$ transformants per μg DNA for uracil prototropic selection and $4.0 \times 10^3$ transformants per μg DNA for tryptophan prototrophic selection. The efficiencies are similar to each other, but lower than that previously determined for pkW018 (Farkas et al., 2011 Appl. Environ. Microbiol. 77:6343-6349 (Example III)) perhaps because of the increased size of the pJFW070 plasmid.

Methods

Strains, Media, and Growth Conditions.

*P. furiosus* DSM 3638 (Fiala and Stetter, 1986 Arch. Microbiol. 145:56-61) wild type and *P. furiosus* COM1 ΔpyrF strains were grown anaerobically in a defined medium with cellobiose as carbon source at 90° C. for 16-18 hours in 100 mL serum bottles containing 50 mL of liquid medium or on medium solidified with phytagel (1% w/v) for ~64 hours. The COM1 ΔpyrF strain was used as a starting strain for further genetic manipulations. For growth of COM1 and other uracil auxotrophic strains, defined media additionally contained 20 μM uracil. Our radA and radB mutant strains, which showed significant growth defects, were grown for 40-42 hours in liquid media, or ~88 hours on plate media. Transformation of *P. furiosus* COM1 ΔpyrF was performed as described in Example 1. Transformation of the JFW02 strain was performed similarly, but also on a media with or without 20 μM uracil and lacking tryptophan. Transformation efficiency was determined by counting prototrophic colonies and the calculating the total amount of transforming DNA added. These frequencies do not take into account the plating efficiency. Pop-out recombination was allowed by growing a 1% inoculum of purified marker replacement strains in defined cellobiose media containing 20 uM uracil. Recombinants were selected by plating onto defined media containing 20 μM uracil and 3 mM 5-FOA.

TABLE 4

*P. furiosus* strains used and constructed in this study

| Strain | Genotype | Parent strain | Reference |
|---|---|---|---|
| DSM3638 | Wild type | — | (Fiala, 1986) |
| GLW101 | COM1 ΔpyrF | DSM 3638 | (Lipscomb, 2011); Example I |
| JFW01 | COM1 ΔpyrF trpAB::P$_{gdh}$pyrF | GLW101 | this example |
| JFW02 | COM1 ΔpyrF ΔtrpAB | JFW01 | this example |

PCR Amplification and Transformation of Wild Type pyrF Gene.

PCR amplifications of the wild type pyrF gene with flanking regions ranging in length from 0 to 1000 bp were performed using the following primer sets: GL055-GL058; pyrF500bpF-10pyrF500 bpR; pyrF250bpF-pyrF250 bpR; pyrF150bpF-pyrF150 bpR; pyrF100bpF-pyrF100 bpR; pyrF50bpF-pyrF50 bpR; pyrF40bpF-pyrF40 bpR; pyrF30bpF-pyrF30 bpR; pyrF20bpF-pyrF20 bpR; pyrF10bpF-pyrF10bpR; pyrF0bpF-pyrF0 bpR; pyrF50bpF-pyrF500 bpR; pyrF40bpF-pyrF500 bpR; pyrF30bpF-pyrF500 bpR; pyrF20bpF-pyrF500 bpR; pyrF10bpF-pyrF500 bpR; and pyrF0bpF-pyrF500 bpR (Table 3). These products were purified using a DNA Clean & Concentrator™-25 column (Zymo Research), and transformed into the *P. furiosus* COM1 ΔpyrF strain. The experiment was performed with three biological replicates for each PCR product.

trpab Pop-Out Marker Replacement Strategy.

Sequence Manipulation Suite was used to generate a random 40 bp sequence (5'-aagtgagcgtgttacgccgagacccg-gtttcgtctctcat-3'; SEQ ID NO:104) that was altered slightly at the 3' end to prevent hairpin or self-annealing structures that could be problematic in PCR. This sequence was used for pop-out recombination and was introduced into our pop-out PCR product through 5' primer tails. Two primer sets (JF392-JF393, JF394-JF395, Table 3) were used to amplify trpAB 1 kb flanking regions. The P$_{gdh}$pyrF marker cassette was amplified from pJFW017 (Farkas et al., 2011 Appl. Environ. Microbiol. 77:6343-6349 (Example III)) plasmid DNA using primers JF355.3 and JF356.3. The specific annealing regions of these primers were designed specifically with melting temperatures at 55±4° C. The overlap tails were 30-35 bases in length, and designed so that the overlapping regions between PCR products would be 20-25 bases in length, melting at 62±2° C. PCR was performed using Pfu Turbo polymerase in a 50 μL reaction volume according to manufacturer's specifications (Stratagene). Thermal cycling included 30 cycles with annealing at 58° C., and a 70 second extension at 72° C. These products were purified using a DNA Clean & Concentrator™-25 column (Zymo Research). These three fragments were put together through two rounds of Splicing by Overlap Extension (SOE) PCR (Horton et al., 1990 Biotechniques 8:528-535). The trpAB upstream flanking region was joined to the P$_{gdh}$-pyrF marker cassette, and in a separate reaction, the P$_{gdh}$-pyrF marker cassette was also joined to the trpAB 3' flanking region. Overlap PCR was performed using ~50 ng of each template DNA in a 50 μL at reaction as before. Prior to thermal cycling, template was denatured without primers, allowed to anneal at 58° C., and extended for 10 minutes at 72° C. Subsequently, 30 cycles of amplification were performed as before, with the same end primers used to generate the template products, and the extension time increased to 120 seconds. These two products were purified and used as template for another SOE PCR. In the second overlap PCR, the first annealing step was removed, and the two fragments were allowed to anneal and extend at 72° C. for 10 minutes. Again, 30 cycles of amplification were performed as before, with JF392 and JF395, and extension time increased to 180 seconds. The 3 kb PCR product was then transformed into the *P. furiosus* COM1 ΔpyrF strain as previously described, and plated onto defined medium without uracil. After ~60 hours of growth at 90° C., the plates were removed from the incubator. Eight putative transformants (uracil prototrophs) were picked into liquid defined medium without uracil and grown overnight at 90° C. Putative transformants were screened for the marker replacement by PCR with JF392 and JF395, using conditions described previously to generate the pop-out PCR product (FIG. 12). One selected transformant was purified to homogeneity by one round of plating onto defined media without uracil, and picking into liquid defined media lacking uracil. Purity of the strain was determined by PCR. Following purification of the intermediate marker replacement strain (JFW01), Selected transformants were plated onto media containing 5-FOA and incubated for ~60 hours . . . pop-out of the $P_{gdh}$pyrF marker cassette was performed as described earlier. This strain (JFW02) was purified to homogeneity as described before and assayed for purity by plating onto PCR and by plating onto defined media lacking uracil.

Construction of pJFW070.

The $P_{pep}$trpAB marker cassette was constructed by SOE PCR. A 126 bp portion of the intergenic region upstream of PEP synthase (PF0043) was amplified from wild-type gDNA using primers GL158 and WN008. The trpAB genes (PF1705, PF1706) were amplified using primers WN009 and WN010. These fragments were joined together resulting in a construct containing the PEP regulatory region, trpAB genes, and a 12 bp terminator from the hpyA1 gene (PF1722).

The $P_{pep}$trpAB marker cassette was treated with T4 polynucleotide kinase and ligated into pJFW018 plasmid (Farkas et al., 2011 Appl. Environ. Microbiol. 77:6343-6349 (Example III)), which was digested with EcoRV and treated with shrimp alkaline phosphatase. *E. coli* strain DH5α cells were transformed by electroporation in a 2-mm-gap cuvette at 2.5 V. Plasmid DNA was isolated from liquid cultures by using QIAprep Spin Miniprep columns (Qiagen Inc.).

Conclusions

Taking advantage of the efficiency of natural competence and recombination in *P. furiosus*, we developed a method for the rapid generation of multiply marked strains of *P. furiosus* and used that method to generate genetic backgrounds for nutritional selection of transformants. We demonstrate the construction of PCR products, generated without cloning, that allow selection for marker replacement and counterselection to pop-out the selectable marker leaving behind a deletion marked only by a 40 bp "scar". The deletion construction is a linear PCR fragment containing the wild type pyrF gene, for prototrophic selection in a ΔpyrF strain, flanked by a 40 bp identical sequence on each side of the marker, flanked by 500 bp of flanking region homologous to upstream and downstream regions of the gene to be deleted. The highly recombinogenic nature of *P. furious* (Lipscomb et al., 2011 Appl. Environ. Microbiol. 77:2232-8 (Example I)) makes the replacement and subsequent pop-out efficient enough to generate hyndreds of recombinants per microgram of DNA even with the most limited homology. Interesting, *P. furious* appears to be much more recombinagenic than the closely related *T. kodakaraensis*, which appears to need greater than >100 bp of homologous flanking region on each side for homologous recombination (Sato et al., 2005 Appl. Environ. Microbiol. 71:3889-3899). In contrast, the hyperthermophilic archeaon *S. acidocaldarius*, like *P. furiosus*, is very recombinogenic and needs very small homologous flanking regions for homologous recombination of linear DNA fragments (Kurosawa and Grogan, 2005 FEMS Microbiol. Lett. 253:141-9).

This method will facilitate the generation of multiply marked strains for the elucidation of gene function and metabolic engineering of any archaeal species that has efficient homologous recombination. It provides a selection for marker replacements with subsequent pop-out of the selected marker generating a deletion strain that may be used iteratively for mutant construction. The ability to select deletions will be critical for the construction of mutations with severe phenotypes In addition to making deletion mutants, the pop-out strategy has been adapted to generating Strep-tag proteins in a single step in vivo and will have other uses that make strain construction rapid.

While the pop-out constructs leave a 40 bp 'pop-out scar' sequence, which remains in the genome after the removal of the $P_{gdh}$-pyrF marker cassette, if a truly markerless deletion is required, this strategy could be modified so that only one 40 bp pop-out sequence is included in the construct, which would recombine with the native sequence on the other side of the $P_{gdh}$-pyrF marker cassette to generate a scarless deletion of the target gene. Conversely, the 40 bp scar sequence provides flexibility for modifying genomic targets by introducing specific sequences such as signal peptides or affinity tags for protein purification.

Homologous recombination has been observed in all biological kingdoms and provides perhaps the most important mechanism for generating genomic diversity. This is accomplished by generating new combinations of existing alleles within a given organism as well as promoting genetic exchange between different organisms that share limited regions of DNA sequence identity. The capacity of DNA for recombination is not solely the property of the DNA molecule itself but rather the cell's complex enzymatic machinery.

Example III

Attempts to Construct a Stable Shuttle Vector for *P. furiosus*

Plasmids based on the high copy pGT5 plasmid from *P. abyssi* have been reported (Lucas et al., 2002 Appl. Environ. Microbiol. 68:5528-5536; Waege et al., 2010 Appl. Environ. Microbiol. 76:3308-3313). These plasmids have a significantly reduced copy number in *P. furiosus* (Waege et al., 2010 Appl. Environ. Microbiol. 76:3308-3313) and cannot be used for selection of transformants in closely related *Thermococcus kodakarensis* (Santangelo et al., 2008 Appl. Environ. Microbiol. 74:3099-3104). Our own constructs based on pGT5 were very unstable, rapidly lost without selection, and showed major internal deletions.

The pGT5 plasmid sequence encodes two open reading frames which cover 85% of the plasmid genome (Erauso et al., 1996 J. Bacteriol. 178:3232-3237). The larger of the ORFs encodes a Rep75 protein involved in rolling-circle replication (Erauso et al., 1996 J. Bacteriol. 178:3232-3237; Marsin and Forterre, 1998 Mol. Microbiol. 27:1183-1192). The smaller ORF does not have a clear function, and does not seem to be necessary for replication (Lucas et al., 2002 Appl. Environ. Microbiol. 68:5528-5536). A predicted replication origin is located 5' of the Rep75 protein (Erauso et al., 1996 J. Bacteriol. 178:3232-3237), and Erauso et al were successful in constructing a *P. abyssi* shuttle vector by opening the pGT5 plasmid 3' of the Rep75 protein and cloning (Erauso et al., 1996 J. Bacteriol. 178:3232-3237; Marsin and Forterre, 1998

Mol. Microbiol. 27:1183-1192) the plasmid into an *E. coli* plasmid. We, therefore, chose to amplify a linear fragment containing pGT5 with a break in this region. A linear pGT5 fragment was produced by PCR amplification from total *P. abyssi* DNA, using primers JF254 and JF270, and this fragment was cloned into pJFW017 to produce pJFW019.

The pJFW019 plasmid was used to transform *P. furiosus* COM1 ΔpyrF cells selecting uracil prototrophy. PCR screening of transformants (amplification of the aac gene on the plasmid) showed that transformants did, in fact, contain at least this portion of the plasmid but often DNA from these transformants used to back-transform *E. coli* did not yield transformants. Plasmid DNA isolated from *E. coli* back-transformants often showed significant internal deletions. These findings are consistent with the fact that plasmids based on this replicon were rapidly lost without selection perhaps because of rearrangements that lead to deterioration of the pJFW019 plasmid in vivo.

Example IV

Defining Components of the Chromosomal Origin of Replication of the Hyperthermophilic Archaeon *Pyrococcus furiosus* Needed for Construction of a Stable Replicating Shuttle Vector In this Example, a series of replicating shuttle vectors were constructed that include a low-copy-number cloning vector for *Escherichia coli* and functional components of the origin of replication (oriC) of the chromosome of the hyperthermophilic archaeon *Pyrococcus furiosus*. In the process of identifying the minimum replication origin sequence required for autonomous plasmid replication in *P. furiosus*, it was discovered that several features of the origin predicted by bioinformatic analysis and in vitro binding studies were not essential for stable autonomous plasmid replication. A minimum region required to promote plasmid DNA replication was identified, and plasmids based on this sequence readily transformed *P. furiosus*. The plasmids replicated autonomously and existed in a single copy. In contrast to shuttle vectors based on a plasmid from the closely related hyperthermophile *Pyrococcus abyssi* for use in *P. furiosus*, plasmids based on the *P. furiosus* chromosomal origin were structurally unchanged after transformation and were stable without selection for more than 100 generations. This data is also published in Farkas et al., 2011 Appl. Environ. Microbiol. 77(18):6343-6349.

Materials and Methods

Strains, media, and growth conditions. *E. coli* strain DH5α was used for plasmid DNA constructions and preparations. Standard techniques for *E. coli* were performed as described previously (Sambrook and Russell, *The condensed protocols from molecular cloning: a laboratory manual*. Cold Spring Harbor Laboratory Press, Cold Spring Harbor: New York, N.Y.; 2006). Apramycin was used for selection at 50 mg/ml. Wild-type strain *P. furiosus* DSM 3638 (Fiala and Stetter, 1986 Arch. Microbiol. 145:56-61) and the *P. furiosus* COM1 ΔpyrF strain (Lipscomb et al., 2011 Appl. Environ. Microbiol. 77:2232-2238 (Example I)) were grown anaerobically in a defined medium with cellobiose as the carbon source (Lipscomb et al., 2011 Appl. Environ. Microbiol. 77:2232-2238 (Example I)) at 90° C. for 16 to 20 hours in 100-ml serum bottles containing 50 ml of liquid medium or on medium solidified with Phytagel (1%, wt/vol; Sigma) for 60 hours. The *P. furiosus* COM1 ΔpyrF strain was used as a host for all DNA transformation experiments. *P. abyssi* strain GE5 (Erauso et al., 1992 C. R. Acad. Sci. 314:387-393; Erauso et al., 1993 Arch. Microbiol. 160:338-349) was grown in a liquid base salts medium (Adams et al., 2001 J. Bacteriol. 183:716-724) containing 0.5% (wt/vol) casein hydrolysate and 0.2% (wt/vol) elemental sulfur for 40 to 48 hours at 90° C. under anaerobic conditions. Total genomic DNA was isolated as described previously (Lipscomb et al., 2011 Appl. Environ. Microbiol. 77:2232-2238 (Example I)), except that DNA was precipitated with isopropanol and resuspended with 50 μl TE buffer (10 mM Tris, 1 mM EDTA) containing RNase A (100 ng/ml).

Construction of Vectors and Transformation of *P. furiosus*.

To construct pJFW027 and pJFW018, PCR products containing the indicated regions of the chromosome (FIG. 13) were ligated into a linear DNA fragment containing the entire pJFW017 plasmid (FIG. 14), also generated by PCR using primers JF266 and JF267. To generate plasmids pJFW031 to pJFW044, primers with restriction sites added to the 5' ends were used to allow the digestion and subsequent directional cloning of origin-containing fragments into pJFW017. The 5' end of each fragment contained a BamHI site, and the 3' end contained a ClaI site. The PCR amplification of pJFW017 was done by use of primers JF266.2 and JF267.2 with the same restriction sites. Primers used in these constructions are listed in Table 5, and DNA sequences of the primers are shown in Table 6. *E. coli* strain DH5α cells were transformed by electroporation in a 2-mm-gap cuvette at 2.5 V. Plasmid DNA was isolated from liquid cultures by using QIAprep Spin Miniprep columns (Qiagen Inc.). For DNA transformations, the *P. furiosus* COM1 ΔpyrF strain was grown for 16 to 20 hours in defined liquid medium containing 20 μM uracil. Plasmid DNA (100 to 200 ng) was added to 100 μl of culture and plated onto the defined medium without uracil. Prototrophic colonies were inoculated into liquid medium for DNA isolation. The presence of plasmid sequences in *P. furiosus* was confirmed by PCR amplification of the aac gene, present only on the plasmid, from *P. furiosus* total genomic DNA by using primers JF263 and JF264 (Table 5).

TABLE 5

Plasmid transformation efficiencies[a]

| Plasmid | oriC insert position | 5' primer | 3' primer | Transformation efficiency (no. of transformants/ μg of plasmid DNA) |
|---|---|---|---|---|
| pJFW017 | None | | | $8.2 \times 10^2$ |
| pJFW018 | 15382-16226 | JF268 | JF269 | $9.1 \times 10^5$ |
| pJFW027 | 15382-17576 | JF268 | JF282 | $5.8 \times 10^5$ |
| pJFW031 | 15382-16228 | JF268.2 | JF269.2 | $6.6 \times 10^5$ |
| pJFW032 | 15382-16187 | JF306.2 | JF269.2 | $8.0 \times 10^4$ |
| pJFW033 | 15382-16034 | JF305.2 | JF269.2 | $6.5 \times 10^5$ |
| pJFW034 | 15382-15890 | JF304.2 | JF269.2 | $5.7 \times 10^2$ |
| pJFW035 | 15382-15786 | JF303.2 | JF269.2 | $1.4 \times 10^3$ |
| pJFW037 | 15382-15705 | JF301.1 | JF269.2 | $1.4 \times 10^2$ |
| pJFW038 | 15492-16034 | JF305.2 | JF339 | $4.7 \times 10^1$ |
| pJFW039 | 15561-16034 | JF305.2 | JF345 | $<4.7 \times 10^1$ |
| pJFW042 | 15746-16034 | JF305.2 | JF348 | $<4.7 \times 10^1$ |
| pJFW043 | 15813-16034 | JF305.2 | JF349 | $<4.7 \times 10^1$ |

[a]Genomic locations are based on the numbering convention of the *Pyrococcus furiosus* (accession number NC_003413.1) genome sequence deposited in GenBank. The detection threshold was $4.7 \times 10^2$ transformants per μg of plasmid DNA.

TABLE 6

Primers used in this study

| Primer name | Sequence (5' to 3') | SEQ ID NO: |
|---|---|---|
| JF254 | AGAGAGGATTCACGGTACCATCTTTT | 107 |
| JF255 | ACGTTTCCATCTTTTTATAACTCTCGTG | 108 |
| JF263 | AggtaccGGTTCATGTGCAGCTCCATC | 109 |
| JF264 | CTCCAACGTCATCTCGTTCTC | 110 |
| JF266 | TCACCAGCTCCGCAAG | 111 |
| JF266.2 | TCTCTCTatcgatTCACCAGCTCCGC | 112 |
| JF267 | AGTACATCACCGACGAGCAAG | 113 |
| JF267.2 | AAAAggatccAGTACATCACCGACGAGCAAG | 114 |
| JF268 | ACTTTGTAGCTGCAAACCACC | 115 |
| JF268.2 | AAAAatcgatACTTTGTAGCTGCAAACCACC | 116 |
| JF269 | TCCATTGGAAATTGTGCTCCTAG | 117 |
| JF269.2 | AAAAggatccTCCATTGGAAATTGTGCTCCTAG | 118 |
| JF270 | AGGGTAGTGGCACCAAGG | 119 |
| JF282 | AGTATTCTCTCAAGAGATAGTAGGCAG | 120 |
| JF301.2 | AAAAggatccGACAAACACTCTCCCATATTA | 121 |
| JF303.2 | AAAAggatccTAAACAGAAGTGAAGTCCCCCAG | 122 |
| JF304.2 | AAAAggatccTTCCTGTGGAGACAAAATGAAC | 123 |
| JF305.2 | AAAAggatccTTTTTATCCTTTGCTTGACAAAAACATG | 124 |
| JF306.2 | AAAAggatccTTTCCAGAGGAAACATAACAC | 125 |
| JF339 | AAAAatcgatTTGAAAGGTAAGCAATTTTCACGAG | 126 |
| JF345 | AAAAatcgatCTAATGAACATTTATTCAGTAATTAGCC | 127 |
| JF348 | AAAAatcgatGGTTCCAGTGGAAATGAAACTC | 128 |
| JF349 | AAAAatcgatTAATCTAATGAACTAAAAGGTGC | 129 |
| JF350 | ATATatcgatCATTTTGTCTCCACAGGAAATCTG | 130 |
| GL21 | GATTGAAAATGGAGTGAGCTGAG | 131 |
| GL23 | GTTCATCCCTCCAAATTAGGTG | 132 |

Restriction sites used for cloning are indicated in lowercase letters.

Assessment of Plasmid Maintenance, Stability, and Copy Number.

To assess plasmid maintenance, *P. furiosus* transformants were serially subcultured every 24 hours for 10 days in selective and nonselective liquid media. After each passage, the culture was diluted 100-fold with base salts, and 30 μl of diluted culture was plated onto selective medium to determine the number of prototrophic colonies, i.e., those maintaining the plasmid. The cell density of the liquid culture was determined by direct cell counting using a Petroff-Hausser counting chamber. To assess the structural stability of the plasmid, total genomic DNA isolated from five independent *P. furiosus* transformants containing pJFW027 was used to back-transform *E. coli* for plasmid isolation and restriction digestion analysis. To determine plasmid copy numbers, total genomic DNA was isolated from *P. furiosus* plasmid transformants and digested twice with 10 U of HpaI for 120 min at 37° C. The restriction fragments were separated by electrophoresis in a 1.0% (wt/vol) agarose gel and transferred onto nylon membranes (Roche, Manheim, Germany). Primers GL021 and GL023 (Lipscomb et al., 2011 Appl. Environ. Microbiol. 77:2232-2238 (Example I)) were used to amplify the glutamate dehydrogenase (gdh) promoter from wild-type *P. furiosus* total genomic DNA to generate a digoxigenin (DIG)-labeled probe by random priming with DIG High Prime DNA Labeling and Detection Starter Kit I (Roche, Manheim, Germany). The membrane was incubated at 42° C. and washed at 65° C. Band intensities were determined by using a Storm 840 PhosporImager (GE Healthcare) equipped with ImageQuant v.5.4 software (Molecular Dynamics).

Results and Discussion

The *P. furiosus* Chromosomal Replication Origin Functions for Stable Autonomous Plasmid Replication.

Figure 16:
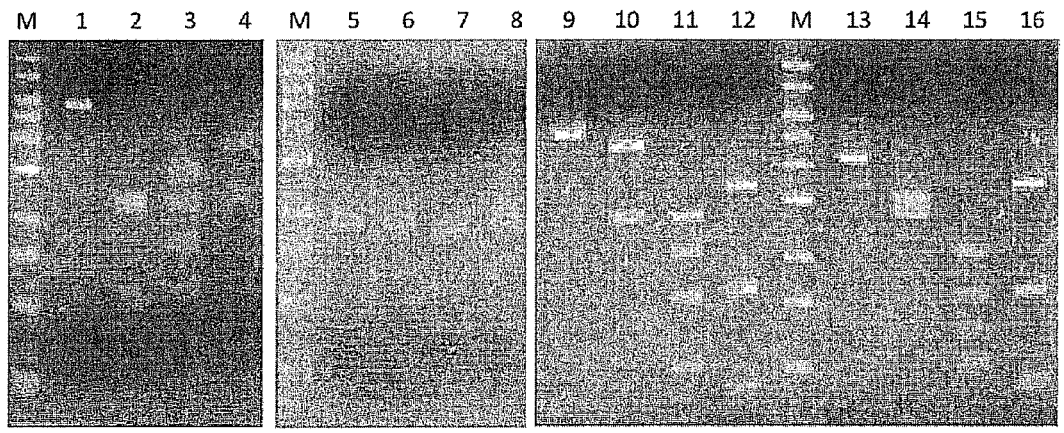
FIG. 16 shows restriction analysis of pJFW019 plasmid DNA before and after transformation of *P. furiosus* and back-transformation to *E. coli*. 1 kb DNA ladder (Lanes M). pJFW019 plasmid DNA isolated from *E. coli* DH5α (Lane 1), and digested with AccI (Lane 2), AvaI (Lane 3), and HindIII (Lane 4). Plasmid DNA isolated from three independent *E. coli* DH5α back-transformants (Lane 5-8, 9-12, and 13-16), undigested and digested with these same enzymes in the same order.

Attempts to construct a stable replicating shuttle vector based on plasmid pGT5 from *P. abyssi* for use in *P. furiosus* were unsuccessful. Plasmids based on pGT5 exist in high copy numbers in *P. abyssi* (Lucas et al., 2002 Appl. Environ. Microbiol. 68:5528-5536; Waege et al., 2010 Appl. Environ. Microbiol. 76:3308-3313) but show a significantly reduced copy number in *P. furiosus* (Waege et al., 2010 Appl. Environ. Microbiol. 76:3308-3313) and cannot be used for the selection of transformants in the closely related *Thermococcus kodakarensis* (Santangelo et al., 2008 Appl. Environ. Microbiol. 74:3099-3104). In an attempt to construct a shuttle vector based on pGT5, the entire plasmid was cloned into pJFW017 that contained a pSC101 origin for replication in *E. coli*, an apramycin resistance gene for selection in *E. coli*, and a wild-type copy of the *P. furiosus* pyrF gene for the selection of transformants in the *P. furiosus* COM ΔpyrF strain. A fragment containing the entire pGT5 plasmid sequence was produced by PCR amplification with primers JE254 and JF270, linearizing the plasmid at a site within pGT5 previously shown not to interfere with replication functions (Erauso et al., 1996 J. Bacteriol. 178:3232-3237; Marsin and Forterre, 1998 Mol. Microbiol. 27:1183-1192), to produce pJFW019 (FIG. 15). This plasmid readily transformed *P. furiosus* but was rapidly lost without selection (Table 7) and showed internal deletions after transformation into *P. furiosus* and subsequent back-transformation into *E. coli* (FIG. 16). Other attempts to use pGT5 for the construction of shuttle vectors in *T. kodakarensis* were similarly unsuccessful (Santangelo et al., 2008 Appl. Environ. Microbiol. 74:3099-3104).

TABLE 7

Maintenance of plasmids in *P. furiosus*[a]

| | No. of cells | | | | | |
|---|---|---|---|---|---|---|
| | pJFW018 | | pJFW027 | | pJFW019 | |
| passage | +ura | −ura | +ura | −ura | +ura | −ura |
| 1 | 187 | 256 | 190 | 194 | 73 | 112 |
| 2 | 132 | 217 | 97 | 203 | 54 | 268 |
| 3 | 112 | 232 | 132 | 143 | 11 | 138 |
| 4 | 146 | 117 | 154 | 165 | 6 | 83 |
| 5 | 87 | 276 | 100 | 113 | 0 | 77 |
| 6 | 138 | 197 | 151 | 201 | 0 | 104 |
| 7 | 144 | 263 | 111 | 122 | 0 | 91 |
| 8 | 118 | 242 | 87 | 131 | 0 | 94 |
| 9 | 93 | 213 | 114 | 218 | 0 | 97 |
| 10 | 107 | 183 | 112 | 169 | 0 | 87 |

[a]Transformants containing each plasmid were serially passaged in liquid medium with uracil (+ura) or without uracil (−ura). Following each passage, a diluted culture was plated onto selective medium to determine the number of prototrophic cells remaining.

Figure 17:
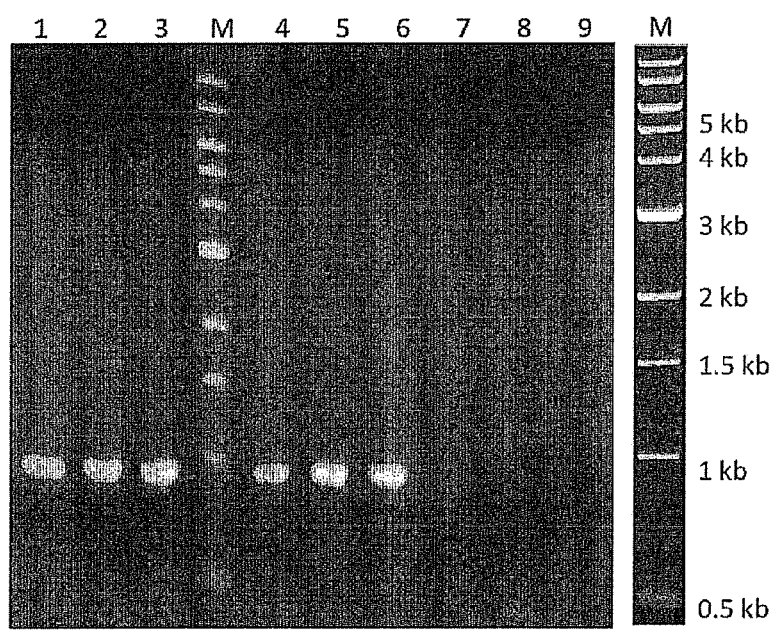
FIG. 17 shows PCR confirmation of plasmid transformation of *P. furiosus*. 1 kb DNA ladder (Lane M, NEB). PCR amplification of aac from pJFW018 (Lane 1), pJFW019 (Lane 2), and pJFW027 (Lane 3) plasmid DNA isolated from *E. coli* DH5α.PCR amplification of aac from genomic DNA from *P. furiosus* transformants of pJFW018 (Lane 4), pJFW019 (Lane 5), and pJFW027 (Lane 6). No product was amplified from *P. furiosus* wild type (Lane 7), COM1 ΔpyrF (Lane 8) or the no template control (Lane 9).

To test whether the predicted *P. furiosus* chromosomal origin of replication could promote stable autonomous plasmid replication, a fragment of the chromosome containing the predicted origin sequence and the gene encoding Cdc6/Orc1 (FIG. 13) was cloned into an *E. coli* plasmid, pJFW017 (FIG. 14), to make pkW027. We used the transformation efficiency as an assay for plasmid replication (Berquist and DasSarma, 2003 J. Bacteriol. 185:5959-5966). As shown in Table 5, transformants of pJFW027 were observed at a frequency of $5.8 \times 10^5$ transformants per µg of plasmid DNA. No transformants were observed in the absence of added plasmid DNA, and while some transformants were obtained in experiments with pJFW017, which does not contain an origin sequence ($8.2 \times 10^2$ transformants per µg of plasmid DNA), this is most likely due to integration by homologous recombination between the gdh promoter region (283 bp), driving the transcription of the pyrF gene on the plasmid, and the gdh locus in the chromosome. In fact, we have observed the integration of nonreplicating plasmid DNA by homologous recombination at the same frequency (Lipscomb et al., 2011 Appl. Environ. Microbiol. 77:2232-2238 (Example I)). The transformation frequency of pJFW027 was a thousandfold greater than that of pJFW017, indicating that the plasmid was replicating autonomously. PCR amplification of the apramycin resistance gene, contained only on the plasmids, was used to confirm the presence of plasmid DNA in the transformants. A 950-bp product containing this sequence was obtained from transformant total genomic DNA but not from the wild-type or the *P. furiosus* COM1 ΔpyrF strain (FIG. 17).

Attempts to isolate a significant quantity of pJFW027 plasmid DNA from *P. furiosus* were unsuccessful. This is perhaps not surprising, since quantities of plasmids based on the chromosomal origin would be expected to be low or 1 copy per chromosome. In lieu of direct plasmid isolation, we chose to rescue the plasmid by back-transformation to *E. coli*. That transformants contained a replicating copy of the plasmid was shown by using total genomic DNA isolated from 5 independent plasmid transformants to back-transform *E. coli* strain DH5α selecting for apramycin resistance. Back-transformants were obtained at frequencies of $10^4$ transformants per µg of DNA, an underestimate of the plasmid transformation, since this frequency is based on the number of transformants per microgram of total genomic DNA, and only covalently closed circular plasmid DNA is capable of transforming *E. coli* strain DH5α at this frequency (Hoekstra et al., 1980 J. Bacteriol. 143:1031-1032). Plasmid DNA isolated from these back-transformants was indistinguishable from the pJFW027 plasmid DNA used to transform *P. furiosus* by using restriction digestion analysis, indicating that there were no gross rearrangements during transformation and replication in *P. furiosus* or subsequent back-transformation to *E. coli*. When the $P_{gdh}$ fragment, specific to plasmid pJF W027, was used as a probe for the Southern hybridization of total genomic DNA from the *P. furiosus* transformants with DNA digested with either EcoRV (data not shown) or HpaI (FIG. 18), which have a single cleavage site within the plasmid, a single band was detected, showing that the plasmid DNA was not integrated into the chromosome and existed as an autonomously replicating molecule.

Figure 19:
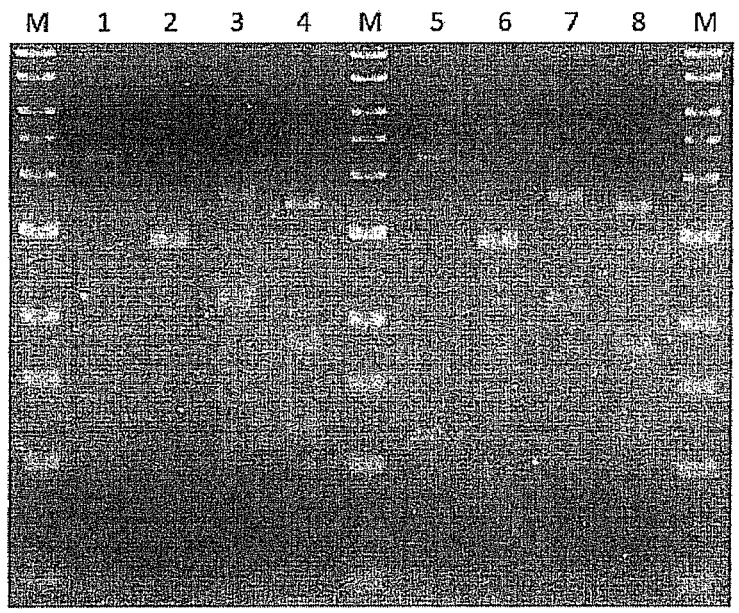
FIG. 19 shows restriction analysis of plasmid DNA before and after transformation of *P. furiosus* and back-transformation to *E. coli*. Lanes M, 1-kb DNA ladder; lanes 1 to 4, pJFW018 plasmid DNA isolated from *E. coli* DH5α (lane 1) and digested with AccI (lane 2), AvaI (lane 3), and HindIII (lane 4); lanes 5 to 8, plasmid DNA isolated from *E. coli* DH5α back-transformed from *P. furiosus* transformants (lane 5) and digested with AccI (lane 6), AvaI (lane 7), and HindIII (lane 8).

To examine plasmid maintenance, transformants of pJFW027 and pJFW018 were serially subcultured in liquid medium with or without selection (i.e., in the absence or presence of uracil) for more than 100 generations and then plated onto minimal medium without uracil to assay plasmid maintenance. No loss of plasmids with oriC was detected even without selection (Table 7). In addition, the restriction pattern of plasmid DNA isolated from *E. coli* after transformation into *P. furiosus* and subsequent transformation back into *E. coli* remained unchanged, indicating that no rearrangements of the plasmid DNA occurred (FIG. 19 [data for 1 of 10 transformants tested are shown]).

The cdc6/orc1 Open Reading Frame is not Required in Cis for Replication Origin Function.

Figure 13:
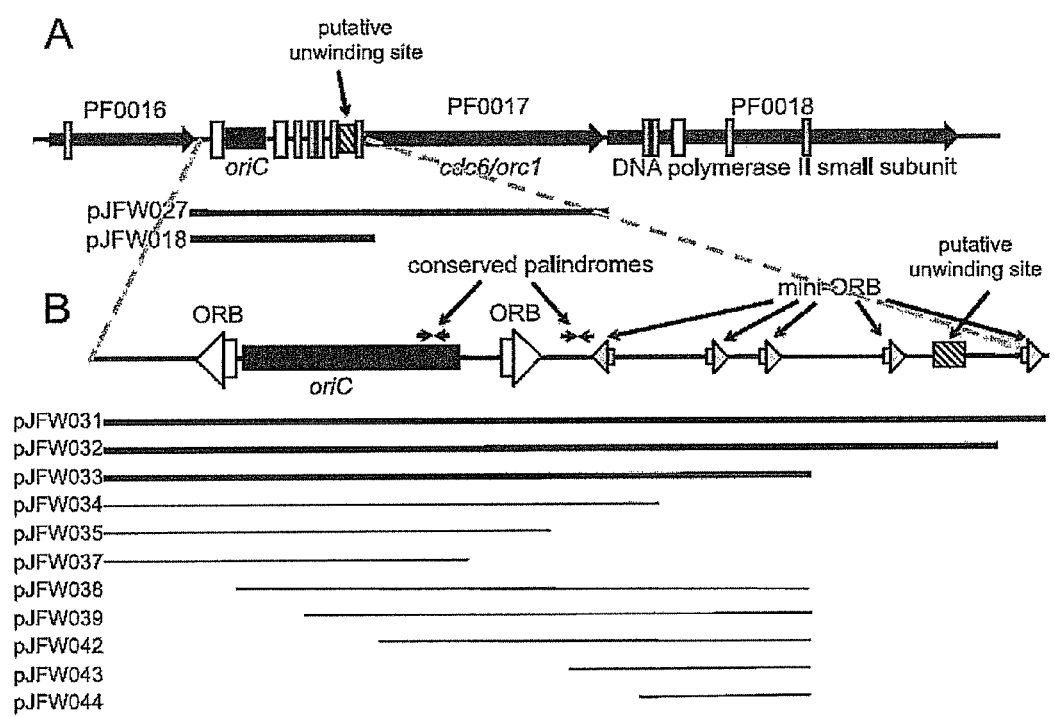
FIG. 13 shows the region of the *P. furiosus* chromosome predicted to contain the origin of replication, oriC (A), with an expanded view of the intergenic space (B). ORBs are indicated in white arrows/bars, mini-ORBS are shown in grey arrows/bars, and the putative unwinding site is shown in hatched bars. The chromosomal regions that were cloned into pJFW017 to produce various plasmids are indicated by black lines below the diagrams. Conserved palindromes are marked by inverted black arrows. Inserts that resulted in plasmids capable of autonomous replication in *P. furiosus* are indicated by thick black lines.

In bacteria, oriC is often, but not always, adjacent to dnaA. In *E. coli*, oriC is between gidA and mioC (which encodes another replication protein), approximately 43 kb from dnaA, and can function for the autonomous replication of plasmids without cis-acting replicating components (Oka et al., 1980 Mol. Gen. Genet. 178:9-20; Sugimoto et al., 1978 Proc. Natl. Acad. Sci. U.S.A. 76:575-579). In the chromosome of Halobacterium NRC-1, oriC requires the adjacent orc7 gene in cis for autonomous plasmid replication (Berquist and DasSarma, 2003 J. Bacteriol. 185:5959-5966). In *Sulfolobus solfataricus*, there are three origins of replication, and for each origin of replication, a cdc6 gene is adjacent but is not required in cis for the origin to function in autonomous plasmid replication (Contursi et al., 2004 Extremophiles 8:385-391). In the sequenced *Pyrococcus* species *P. furiosus*, *P. abyssi*, and *P. horikoshii* as well as the closely related *T. kodakarensis*, there is a single oriC adjacent to a cdc6/orc1 homologue, but nothing is known about the requirement of this protein for oriC function. To test whether cdc6/orc1 was required in cis for autonomous plasmid replication in *P. furiosus*, a fragment containing only oriC was cloned into parent plasmid pJFW017 to generate pJFW18 (FIG. 13). As shown in Table 5, plasmids containing the fragment with only the oriC sequence without the cdc6/orc1 gene transformed *P. furiosus* as efficiently and were maintained as stably as plasmid pJFW27 carrying the cdc6/orc1 gene, suggesting that the cdc6/orc1 gene is not required in cis for stable autonomous plasmid replication.

Only Two of the Predicted ORB Sequences and Part of the Predicted Chromosomal Origin Sequence are Required for Plasmid Replication.

The origin region was predicted previously to contain several ORB and mini-ORB sequences (Matsunaga et al., 2007 Nucleic Acids Res. 35:3214-3222), suggested to be binding sites for the replication initiation protein Cdc6/Orc1, which is presumed to facilitate the nucleation of the replication complex. Our analysis using the BLASTN 2.2.24+ algorithm (Altschul et al., 1997 Nucleic Acids Res. 25:3389-3402) identified three ORB repeats and several mini-ORB repeats by the self-alignment of the sequence of the genomic region containing oriC and neighboring genes. These results are similar but not identical to those described previously by Matsunaga et al. (Matsunaga et al., 2007 Nucleic Acids Res. 35:3214-3222), in that we found a clustering of mini-ORB repeats in and around oriC, but the exact number and position of these mini-ORB repeats were different. Tn addition, we identified two conserved palindromic sequences (Table 8) conserved in all sequenced *Pyrococcus* species. One of them contains compensating changes within the sequence that retain the perfect palindromic structure, suggesting that these are not random sequences within this highly repetitive region of DNA and may potentially be binding sites for other replication proteins or have a structural role in replication. These palindromes are not present in the oriC region of the closely related *Thermococcus* species, however, suggesting that if they have a function, it may be specific to *Pyrococcus*. To test whether these sequences were required for autonomous plasmid replication, plasmids containing various portions of the region around the predicted origin were constructed and tested for the ability to replicate. The smallest insert able to promote autonomous plasmid replication was the 653-bp fragment cloned into pJFW033. As shown in Table 5, only two of the three ORB sequences, and only a part of the sequence predicted to contain the origin, were required for plasmid replication. The predicted unwinding site, for example, is apparently not required for autonomous plasmid replication.

TABLE 8

Conserved palindromic sequences within the *Pyrococcus* oriC region[a]

| Species (GenBank accession no.) | Sequence | SEQ ID NO: | Genomic position |
|---|---|---|---|
| Palindrome 1 | | | |
| P. furiosus (NC_003413.1) | ATATTTAAATAT | 133 | 15641-15674 |
| P. abyssi (NC_000868.1) | TATTTAAATA | 134 | 123223-123232 |
| P. horikoshii (NC_000961.1) | TATTTAAATA | 135 | 111307-111316 |
| Palindrome 2 | | | |
| P. furiosus (NC_003413.1) | ATTAgaTTAAtcTAAT | 136 | 15809-15824 |
| P. abyssi (NC_000868.1) | ATTAagTTAAccTAAT | 137 | 123072-123087 |
| P. horikoshii (NC_000961.1) | ATTAagTTAActTAAT | 138 | 111155-111170 |

[a]Base differences are indicated by lowercase type; underlining indicates a base that deviates from the palindrome consensus. Genomic locations are based on the numbering of the genome sequences deposited in GenBank.

Replicating Shuttle Vectors Based on the Chromosomal Origin Exist in Single Copies.

Figure 18:
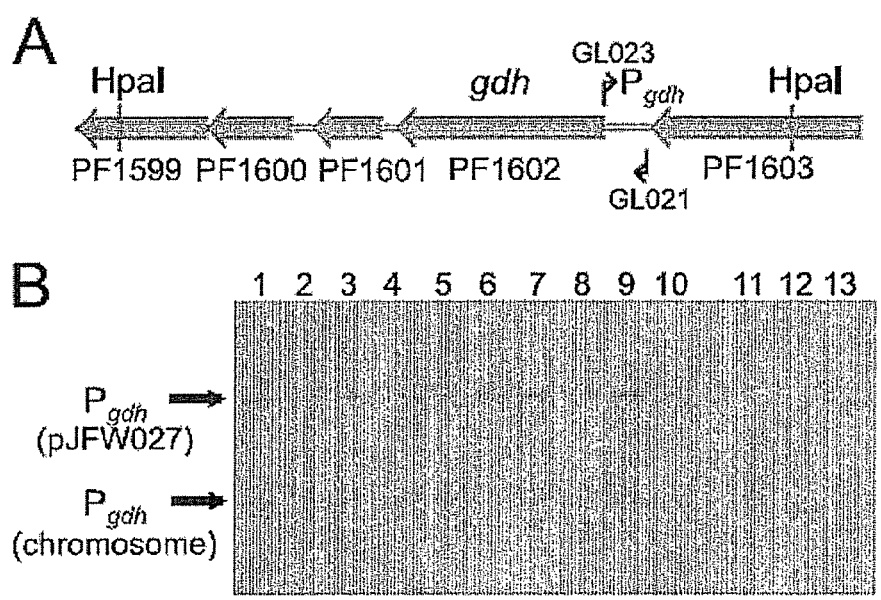
FIG. 18 shows the determination of copy number for pJFW027 in *P. furiosus*.

To determine the approximate copy number of the oriC-based plasmids, a PCR product generated from the Pgdh promoter was used as a probe in Southern hybridization experiments with total genomic DNA from *P. furiosus* wild-type cells and pJFW027 transformants. Since $P_{gdh}$ is present in one copy both on pJFW027 and in the *P. furiosus* chromosome, a densitometry analysis of the amount of DIG-labeled probe hybridized to each one allowed an estimation of the number of plasmid copies per chromosome (FIG. 18). The relative intensities of the plasmid-derived hybridization signal to the chromosomally derived hybridization signal of $P_{gdh}$ for the EcoRV and HpaI digests ranged from 1.4 to 1.8 for 10 transformants tested, indicating that the oriC-based plasmids exist in a single copy per chromosome.

Conclusions

The functional analysis of the replication origin of the *P. furiosus* chromosome reported here showed that only two of the three ORB sequences, those flanking an AT-rich sequence most conserved in arrangement and sequence among the Archaea (Robinson et al., 2004 Cell 116:25-38), and no more than three of the mini-ORB sites are required for autonomous plasmid replication. In particular, the DNA-unwinding site, predicted by P1 endonuclease assays (Matsunaga et al., 2010 Extremophiles 14:21-31), is not required for autonomous plasmid replication, nor are any of the predicted ORB or mini-ORB sequences within the DNA polymerase small-subunit open reading frame. We emphasize that we have not ruled out the possibility that these sequences are important for chromosomal replication and that they may serve to promote additional Cdc6/Orc1 binding for chromosomal replication initiation. The open reading frame encoding the Cdc6/Orc1 protein present adjacent to the predicted origin sequence is not required in cis for autonomous plasmid replication. Vectors based on *P. furiosus* oriC were stably maintained for more than 100 generations without selection and showed no evidence of rearrangement after replication and transformation between *E. coli* and *P. furiosus*. The smallest oriC fragment identified in this study capable of conferring autonomous replication was 653 bp in length, and vectors based on the origin exist in a single copy per chromosome in the cell. Two conserved short palindromes were identified within the origin region that are conserved among *Pyrococcus* species but not in the closely related species *Thermococcus kodakarensis*, suggesting that if they have a function, it may be specific to *Pyrococcus* species. These vectors may have utility for homologous and heterologous gene expression, as well as providing a tool for the study of natural competence, and in vivo studies of replication and recombination in *P. furiosus*.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated *Pyrococcus furiosus* COM1 deposited with the American Type Culture Collection in accordance with the provisions of the Budapest Treaty with the accession number PTA-11303.

2. The isolated *Pyrococcus furiosus* of claim 1 comprising a heterologous polynucleotide.

3. The isolated *Pyrococcus furiosus* of claim 2 wherein the heterologous polynucleotide is integrated into the *P. furiosus* genomic DNA.

4. The isolated *Pyrococcus furiosus* of claim 2 wherein the heterologous polynucleotide is not integrated into the *P. furiosus* genomic DNA.

5. A method for transforming a *Pyrococcus furiosus* with a polynucleotide comprising:
   contacting the *P. furiosus* of claim 1 with a polynucleotide under conditions suitable for uptake of the polynucleotide by the *P. furiosus*; and
   identifying transformants, wherein at least $10^4$ transformants are obtained per microgram DNA.

6. The method of claim 5 wherein at least $10^5$ transformants are obtained per microgram DNA.

7. The method of claim 5 wherein the polynucleotide is a linear polynucleotide.

8. The method of claim 7 wherein the linear polynucleotide comprises an intervening region flanked by a first homology region and a second homology region, wherein the first homology region and the second homology region each comprise nucleotide sequences that are homologous to nucleotide sequences present in the *P. furiosus* genome.

9. The method of claim 8 wherein the first homology region and the second homology region are at least 20 nucleotides in length.

10. The method of claim 5 wherein the polynucleotide is a circular polynucleotide.

11. The method of claim 10 wherein the circular polynucleotide comprises a homology region, wherein the homology region comprises a nucleotide sequence that is homologous to a nucleotide sequence present in the *P. furiosus* genome.

12. The method of claim 11 wherein the homology region is at least 20 nucleotides in length.

13. The method of claim 12 wherein the circular polynucleotide comprises a first homology region and a second homology region, wherein the first and second homology regions each comprise a different nucleotide sequence, wherein each nucleotide sequence is homologous to a nucleotide sequence present in the *P. furiosus* genome.

14. The method of claim 13 wherein the first homology region and the second homology region are at least 20 nucleotides in length.

15. The method of claim 5 wherein the conditions suitable for uptake of the polynucleotide do not include exposing the *P. furiosus* to a heat shock.

16. The method of claim 5 wherein the conditions suitable for uptake of the polynucleotide do not include exposing the *P. furiosus* to $CaCl_2$, an applied electrical field, a liposome, a phage, or conditions resulting in spheroplast formation.

17. The method of claim 5 wherein a portion of the polynucleotide taken up by a transformant is integrated into the *P. furiosus* genome.

18. The method of claim 17 wherein the integration is by homologous recombination between the polynucleotide and the *P. furiosus* genome.

19. A method for transforming a *Pyrococcus furiosus* with a polynucleotide comprising:
   contacting the *P. furiosus* of claim 1 with a polynucleotide under conditions suitable for uptake of the polynucleotide by the *P. furiosus*, wherein the polynucleotide comprises a homology region, wherein the homology region comprises a nucleotide sequence that is homologous to a nucleotide sequence present in the *P. furiosus* genome, and wherein the homology region is at least 20 nucleotides in length.

\* \* \* \* \*